United States Patent
Apte et al.

(10) Patent No.: US 9,663,831 B2
(45) Date of Patent: May 30, 2017

(54) METHOD AND SYSTEM FOR MICROBIOME ANALYSIS

(71) Applicant: uBiome, Inc., San Francisco, CA (US)

(72) Inventors: Zachary Apte, San Francisco, CA (US); Jessica Richman, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

(21) Appl. No.: 14/593,424

(22) Filed: Jan. 9, 2015

(65) Prior Publication Data

US 2015/0213193 A1    Jul. 30, 2015

Related U.S. Application Data

(60) Provisional application No. 62/024,947, filed on Jul. 15, 2014, provisional application No. 61/953,683, filed on Mar. 14, 2014, provisional application No. 61/931,612, filed on Jan. 25, 2014.

(51) Int. Cl.
| | |
|---|---|
| *G01N 33/58* | (2006.01) |
| *C12Q 1/68* | (2006.01) |
| *G06F 19/22* | (2011.01) |
| *G06G 7/58* | (2006.01) |

(52) U.S. Cl.
CPC ........... *C12Q 1/689* (2013.01); *C12Q 1/6869* (2013.01); *C12Q 1/6888* (2013.01); *G06F 19/22* (2013.01)

(58) Field of Classification Search
CPC .................................................... G06F 19/22
See application file for complete search history.

(56) References Cited

U.S. PATENT DOCUMENTS

| | | | |
|---|---|---|---|
| 5,891,630 | A | 4/1999 | Eggers et al. |
| 8,478,544 | B2 | 7/2013 | Colwell et al. |
| 2002/0146745 | A1 | 10/2002 | Natan et al. |
| 2005/0255552 | A1 | 11/2005 | Flynn et al. |
| 2010/0129816 | A1 | 5/2010 | Savelkoul et al. |
| 2010/0172874 | A1 | 7/2010 | Turnbaugh et al. |
| 2012/0045771 | A1 | 2/2012 | Beier et al. |
| 2012/0149584 | A1 | 6/2012 | Olle et al. |
| 2013/0045874 | A1 | 2/2013 | Ehrlich |
| 2014/0093478 | A1 | 4/2014 | Turnbaugh et al. |
| 2014/0136120 | A1 | 5/2014 | Colwell et al. |
| 2014/0199281 | A1 | 7/2014 | Henn et al. |

FOREIGN PATENT DOCUMENTS

| | | |
|---|---|---|
| WO | 2014144092 A1 | 9/2014 |
| WO | 2015067936 A1 | 5/2015 |

OTHER PUBLICATIONS

Cole et al. The Ribosomal Database Project: improved alignments and new tools for rRNA analysis. Nucl Acids Res Jan. 2009 vol. 37 pp. D141-D145. Especially p. 141 col. 1 para1, D143 col. 1 para3.
Darmanis et al. ProteinSeq: high-performance proteomic analyses by proximity ligation and next generation sequencing. PLos One Sep. 29, 2011 vol. 6 No. 9 pp. e25583 pp. 1-10. Especially abstract, p. 2 col. 1 para 1-6, p. 3 fig 1, p. 4 col. 2 para2, p. 6 fig 3c, p. 7 col. 1 para2, p. 7 col. 2, p. 8 col. 2 para 6-7.
IDT Decoded Newsletter. Improving Immuno-PCR by Optimizing Antibody-Oligo Conjugation. [online] Mar. 11, 2015 [retrieved Aug. 29, 2016]. Available on the internet:<URL: https://www.idtdna.com/pages/decoded/decoded-articles/your-research/decoded/2015/03/11/improving-immuno-pcr-by-optimizing-antibody-oligo-conjugation>. Especially PDF p. 2 para 3, PDF p. 3 para 2, PDF p. 3 fig 1, PDF p. 6 para5, PDF p. 7 para 1.
Mahmood et al. Western Blot: technique, theory, and trouble shooting. N Am J Med Sci Sep. 2012 vol. 4 No. 9 p. 429-434. Especially p. 3.

*Primary Examiner* — Eric S Dejong
(74) *Attorney, Agent, or Firm* — Jeffrey Schox; Ivan Wong

(57) ABSTRACT

A method and system for analyzing a microbiome of an individual, comprising: providing a sampling kit to the individual at a location remote from the sample processing network, the sampling kit including a sample container having a lysing component and a sample preservation component and configured to receive a sample from a collection site of the individual; receiving the sample container with the sample from the collection site of the individual; generating a microbiome sequence dataset based upon sequencing nucleic acid content of a microorganism portion of the sample; identifying a set of microorganisms represented in the microorganism portion based upon performance of a mapping operation on portions of the microbiome sequence dataset; generating an analysis based upon a set of features related to the microorganism portion; and transmitting information derived from the analysis to the individual.

22 Claims, 21 Drawing Sheets

| F idx | i5 | transposase | Linker | N* | Linker | 16Sv4 F |
|---|---|---|---|---|---|---|
| AATGATACGGCGAC | NNNN | TCGTCGGCAGCGTCAGA | | N | GT | GTGCCAGCMG |
| CACCGAGATCTACAC | NNNN | TGTGTATAAGAGACAG | | | | CCGCGGTA*A |

| R idx | i7 | transposase | Linker | N* | Linker | 16Sv4 F |
|---|---|---|---|---|---|---|
| CAAGCAGAAGACGG | NNNN | GTCTCGTGGGCTCGGAG | | N | CC | GGACTACHVG |
| CATACGAGAT | NNNN | ATGTGTATAAGAGACAG | | | | GGTWTCTAA*T |

FIGURE 5B

| i5 | |
|---|---|
| CTCACTC | ACTCATC |
| GTATGTG | TTGCGAG |
| GTCCAAC | AAGCGAC |
| TTGCATC | TGCACGA |
| ACAGGAC | TATGCGG |
| TCTGGTG | TCGTCGA |
| TACGTGT | ACACTTG |
| CTACCAA | TACGGCA |
| GAGGTAG | TCTCGTG |
| GCTTAAC | GCAGATG |
| GCAATTC | TCCGTTG |
| TCCTCAC | TTCGCAG |
| AGTTAGC | GGAATAG |
| TCATGGC | GCAACAA |
| AGCCTAA | ACTGCGA |
| AACACTC | TGAGTAC |
| AGAGCTC | ACACGAA |
| GGCCATA | |
| TAGAACG | |
| GGTTGAA | |
| GATCCTA | |
| TGGTCTC | |
| TCCAGTC | |
| TAGCGTA | |
| GCGATCA | |
| AGCTACA | |

FIGURE 5C

| i7 | | |
|---|---|---|
| TAGGTTG | AGGACAC | AATCCGA |
| GGACAAG | ATACGGA | AGACCAA |
| CGAGTAG | AAGCGTA | CCGCTAT |
| CTGTCTC | CGTTGTA | GGTTACA |
| ACAACTG | CTCCTTC | AGCCTGT |
| AAGAGCT | GATGCTT | GCGACTT |
| TTGTGCT | GATCTCA | CGAACTC |
| CCATGCT | GTCTAGA | GAAGAGT |
| GGAAGGT | ATGAGCA | AGGTCTT |
| GTTCCTA | GGAGTTA | GGATGGT |
| TGCATAT | GTGTGTC | ACCGTTC |
| CAATTCG | GCTACAA | |
| GACGTAC | CGTAGAC | |
| AACTGCA | GTAATGC | |
| CCACAGT | ATGGAAC | |
| CTTAACC | GGTATTC | |
| AGTGTGA | CAAGTGA | |
| ACCTCTA | CTTGTGT | |
| ATGTCGC | CTGTAGT | |
| GCATGTA | CCTGAGA | |
| CATCATC | GCACGAT | |
| GCACACA | ACGTGGA | |
| GTAGCGA | CATGGAT | |
| CTAGCTT | CTGCCAA | |
| GGTCCTA | GAGACGA | |
| CCAACGA | CGTAAGT | |

Please list your height (e.g., 5 ft 11, 70in., 180cm., 1.8m, etc.)

Please list your weight (e.g., 160lbs, 88kg, etc.)

Which of the following best describes your diet?

If you selected other above, please briefly describe your diet:

How many alcoholic beverages have you consumed in the last 48 hours?

How many cigarettes have you smoked in the last 48 hours?

How many caffeinated beverages have you consumed in the last 48 hours?

How many diet sodas or juices (beverages over 0.5L or 16oz count as two) have you consumed in the last 48 hours?

FIGURE 13

METHOD AND SYSTEM FOR MICROBIOME ANALYSIS

CROSS-REFERENCE TO RELATED APPLICATIONS

This application claims the benefit of U.S. Provisional Application Ser. No. 62/024,947 filed 15 Jul. 2014, U.S. Provisional Application Ser. No. 61/953,683 filed 14 Mar. 2014, and U.S. Provisional Application Ser. No. 61/931,612 filed 25 Jan. 2014, which are each incorporated in its entirety herein by this reference.

TECHNICAL FIELD

This invention relates generally to the field of microbiology and more specifically to a new and useful method and system for performing microbiome analysis in the field of microbiology.

BACKGROUND

A microbiome is an ecological community of commensal, symbiotic, and pathogenic microorganisms (e.g., bacteria, fungi, archaea, viruses) that are associated with an organism. The human microbiome comprises over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting an individual's health, efforts related to the characterization of the microbiome and generation of insights from the characterization should be pursued. Current methods and systems that attempt to analyze the microbiomes of humans, at individual and population-wide levels have, however, been largely unsuccessful, leaving many questions unanswered.

As such, there is a need in the field of microbiology for a new and useful method and system for performing microbiome analysis. This invention creates such a new and useful method and system.

Figure 6:
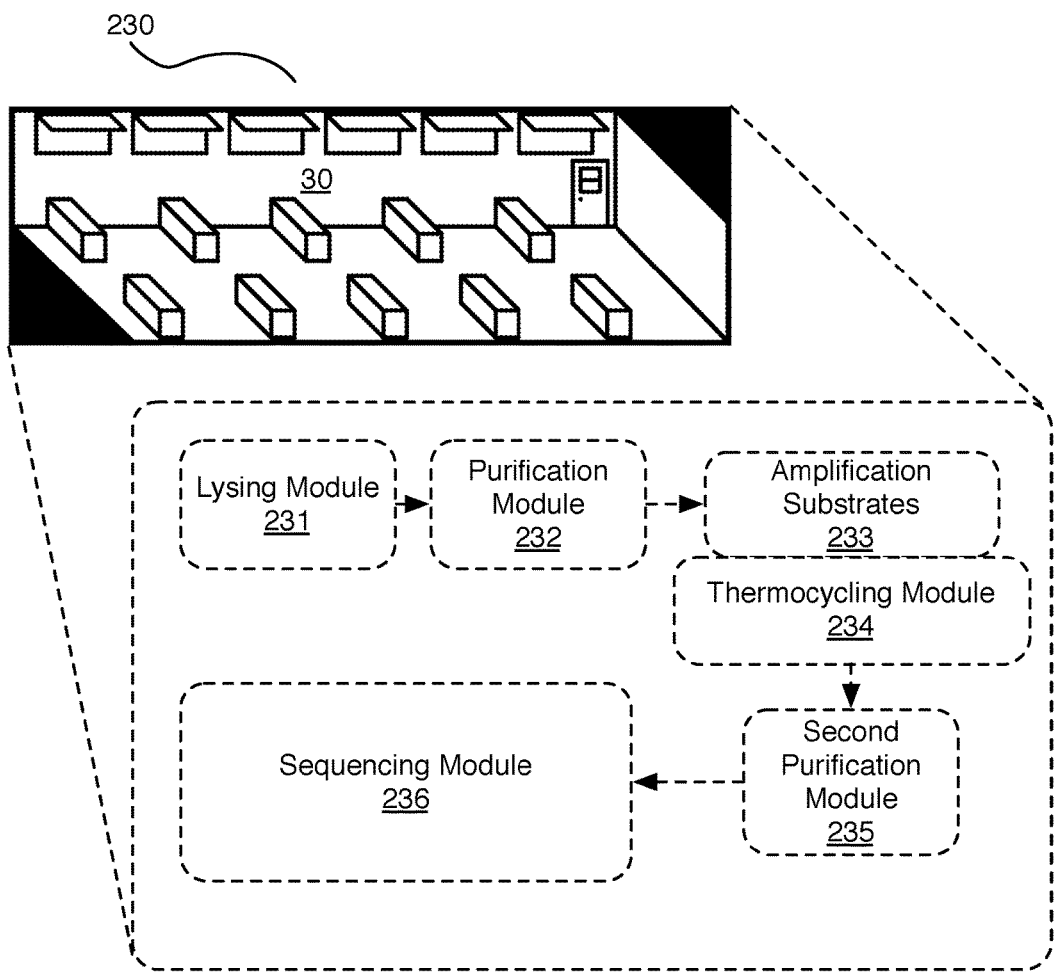
Figure 7A:
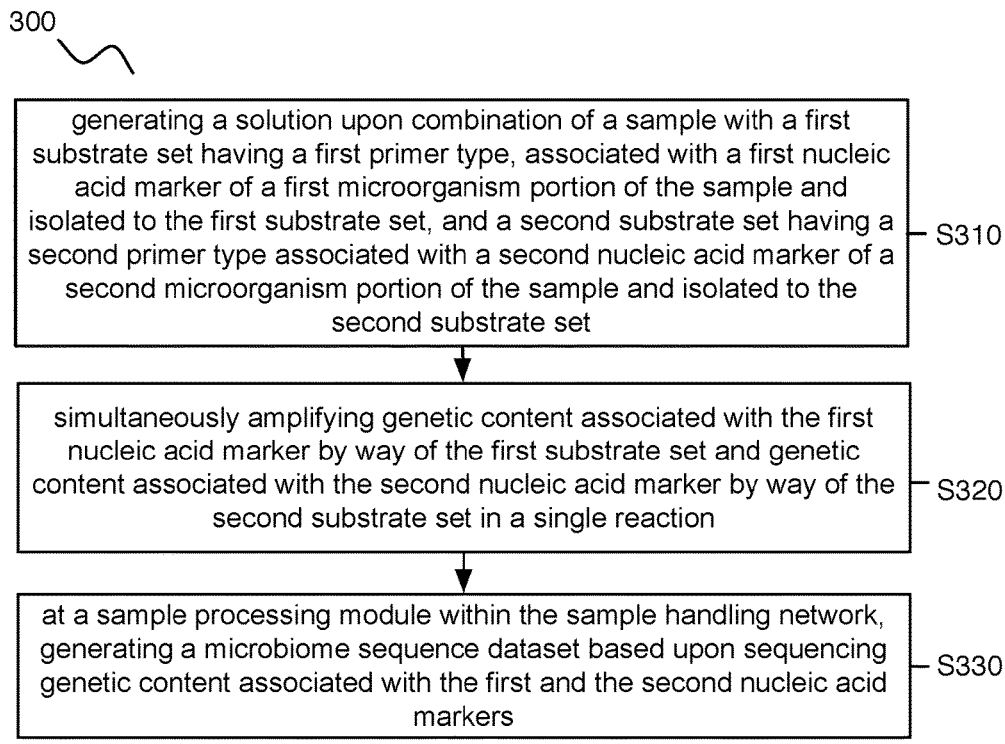
Figure 7B:
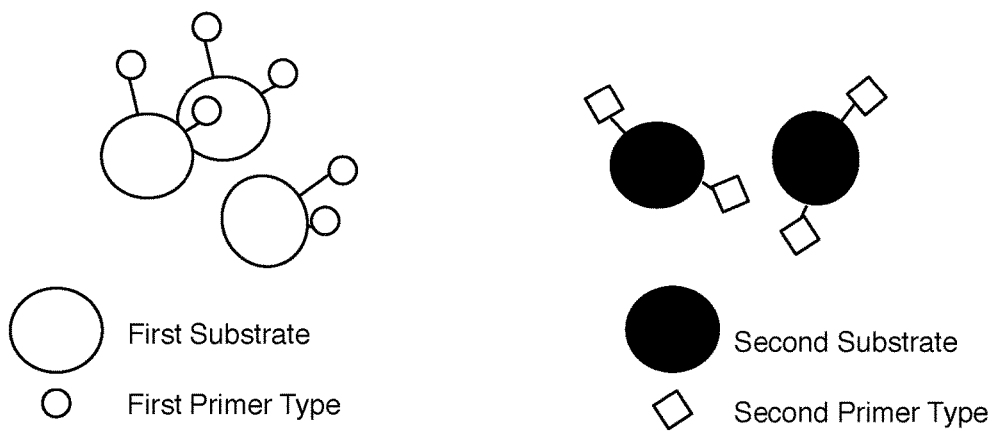
Figure 8:
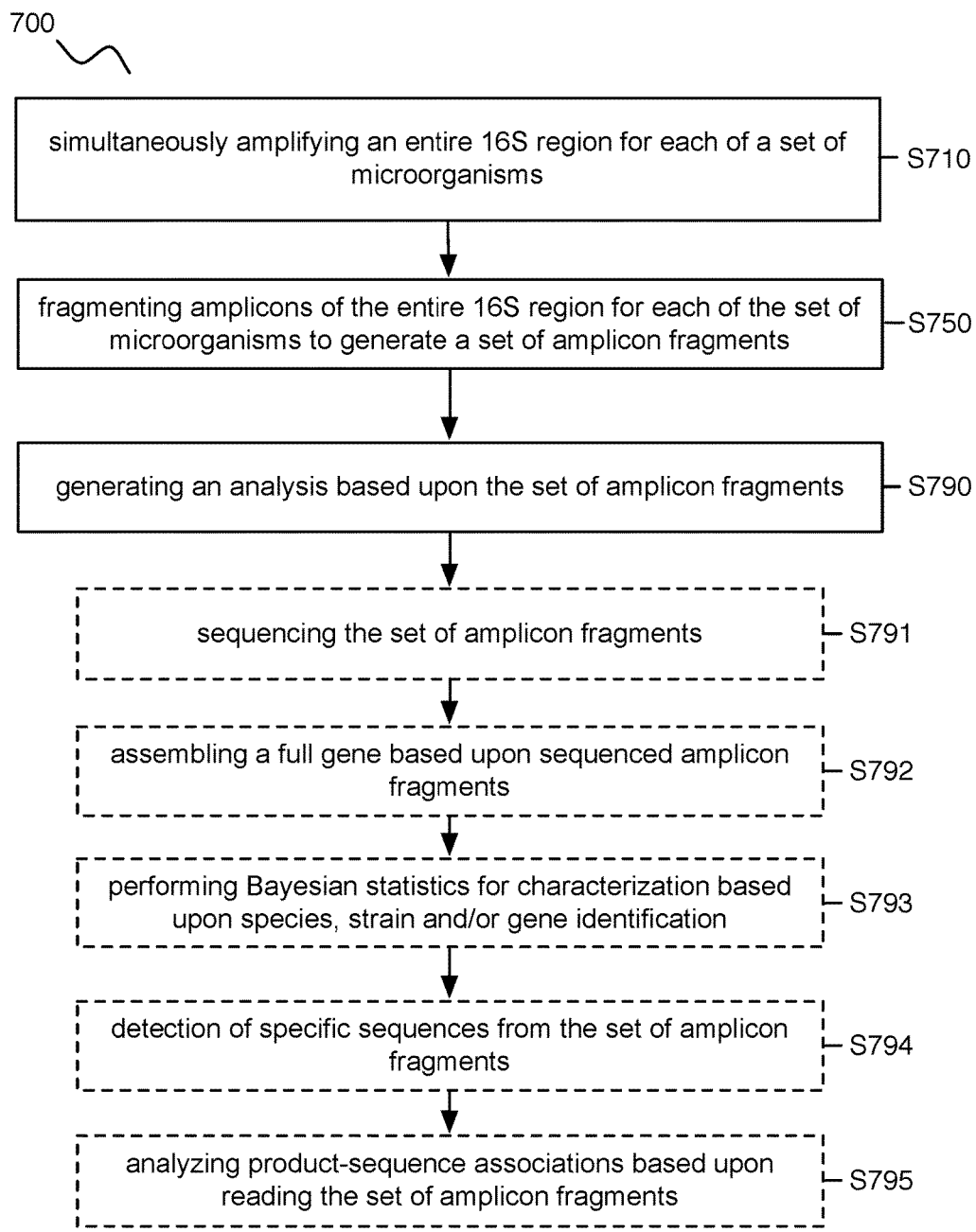
Figure 9A:
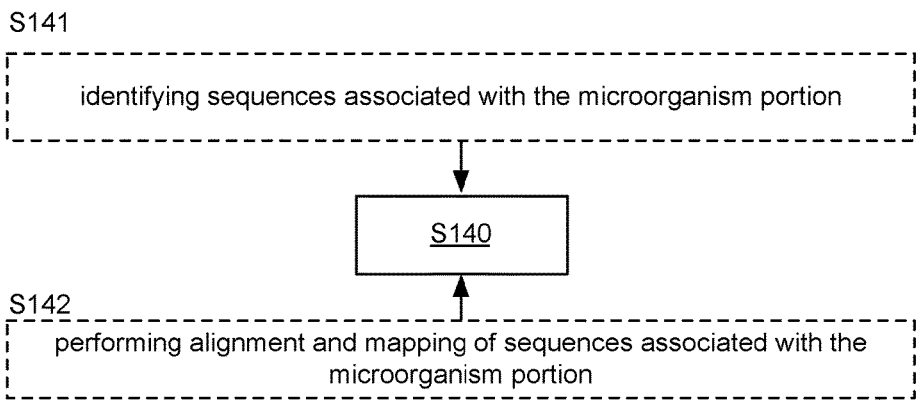
Figure 9B:
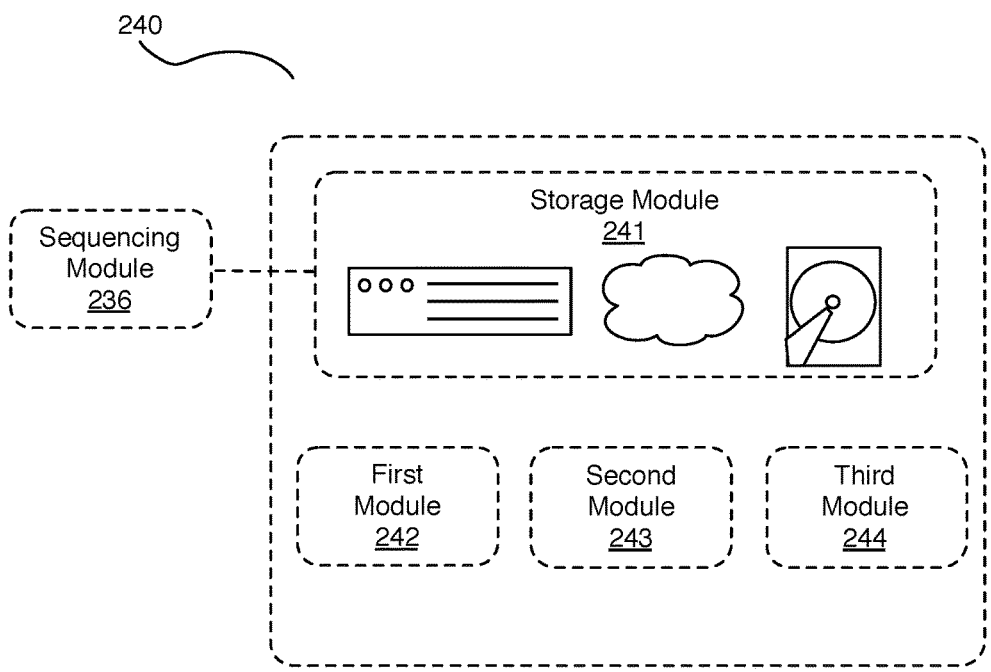
Figure 10:
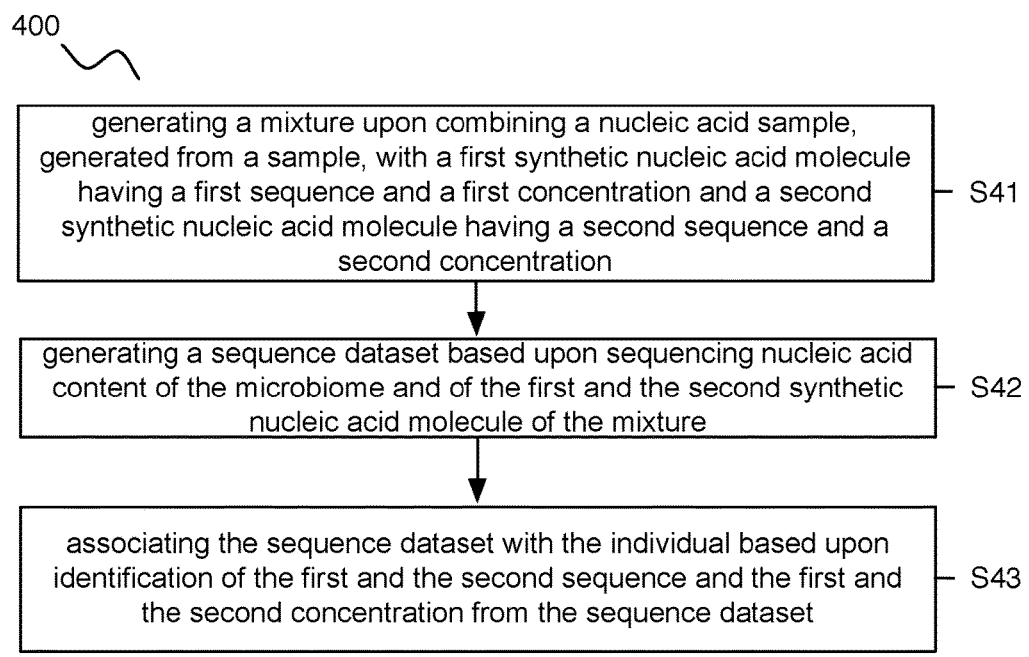
Figure 11A:
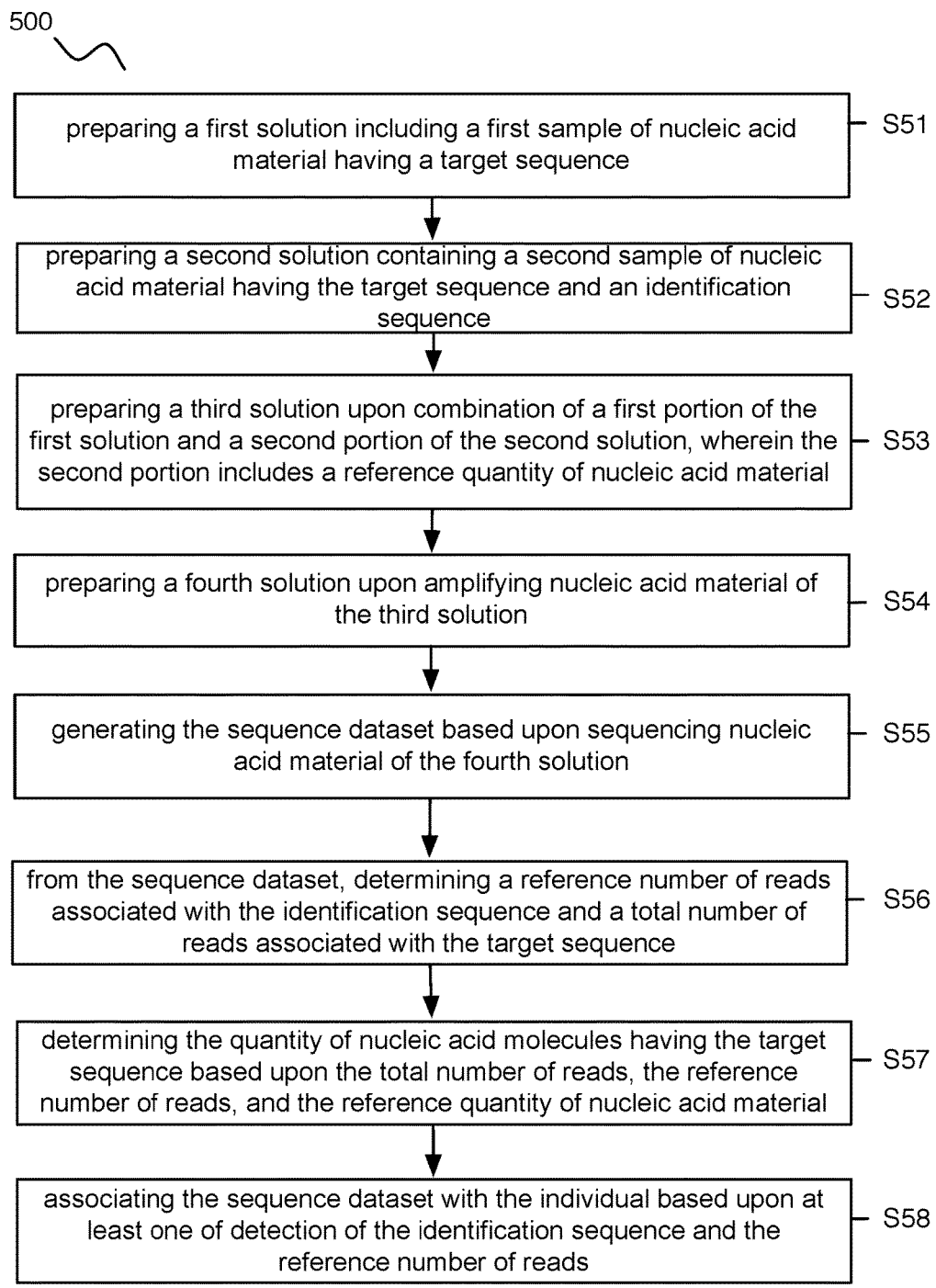
Figure 11B:
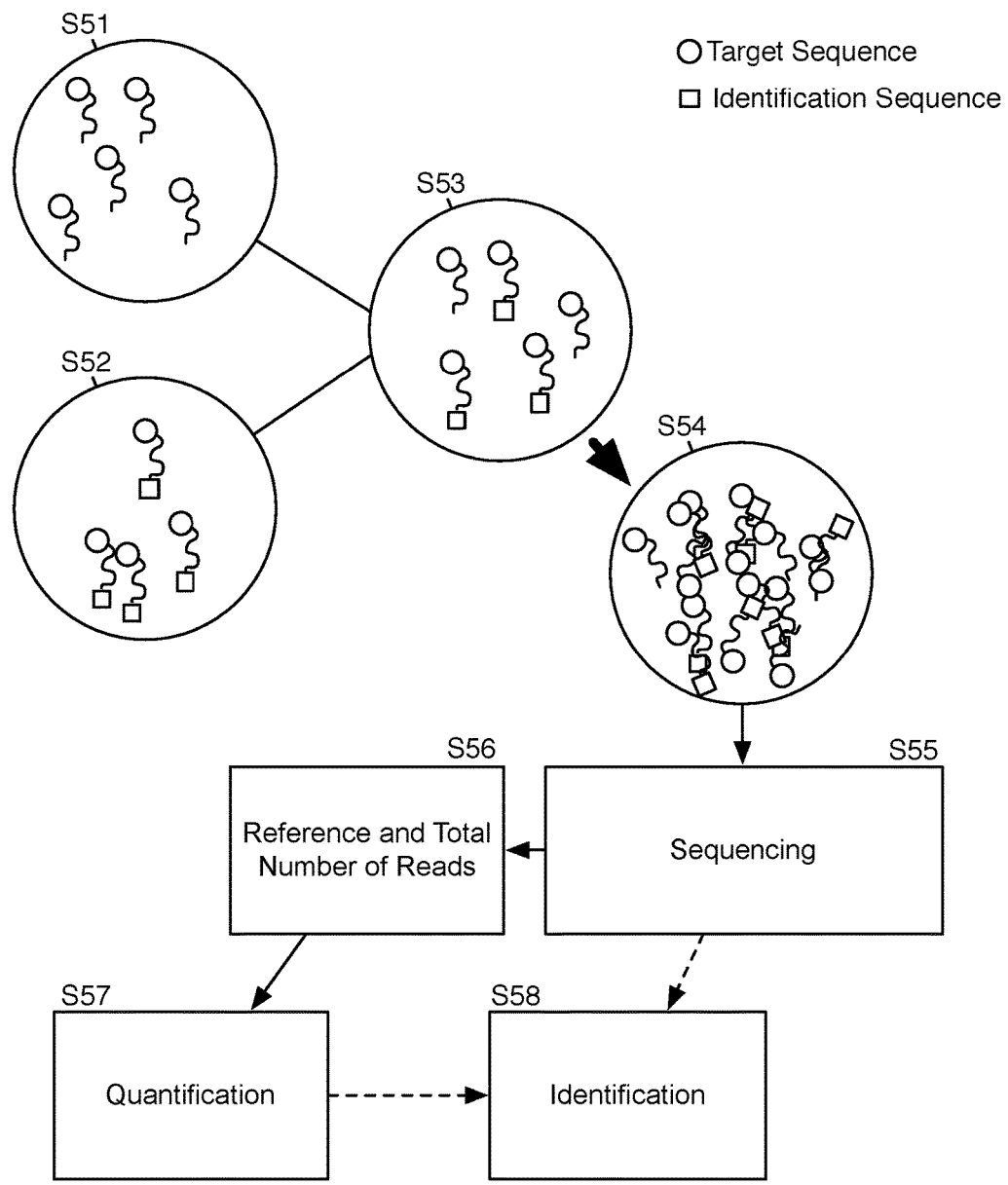
Figure 12:
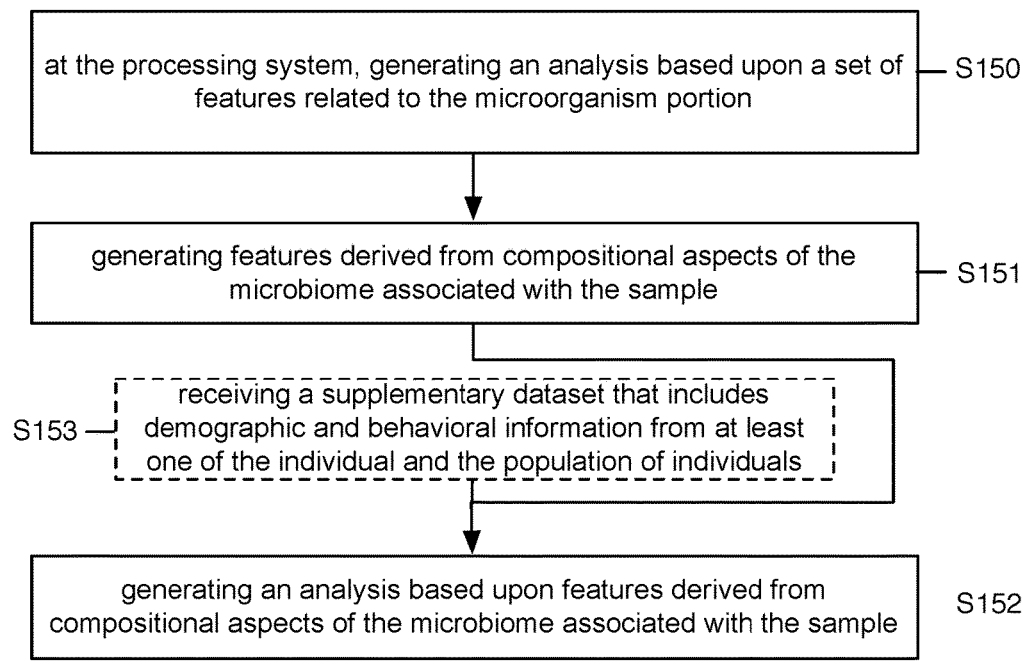
Figure 14:
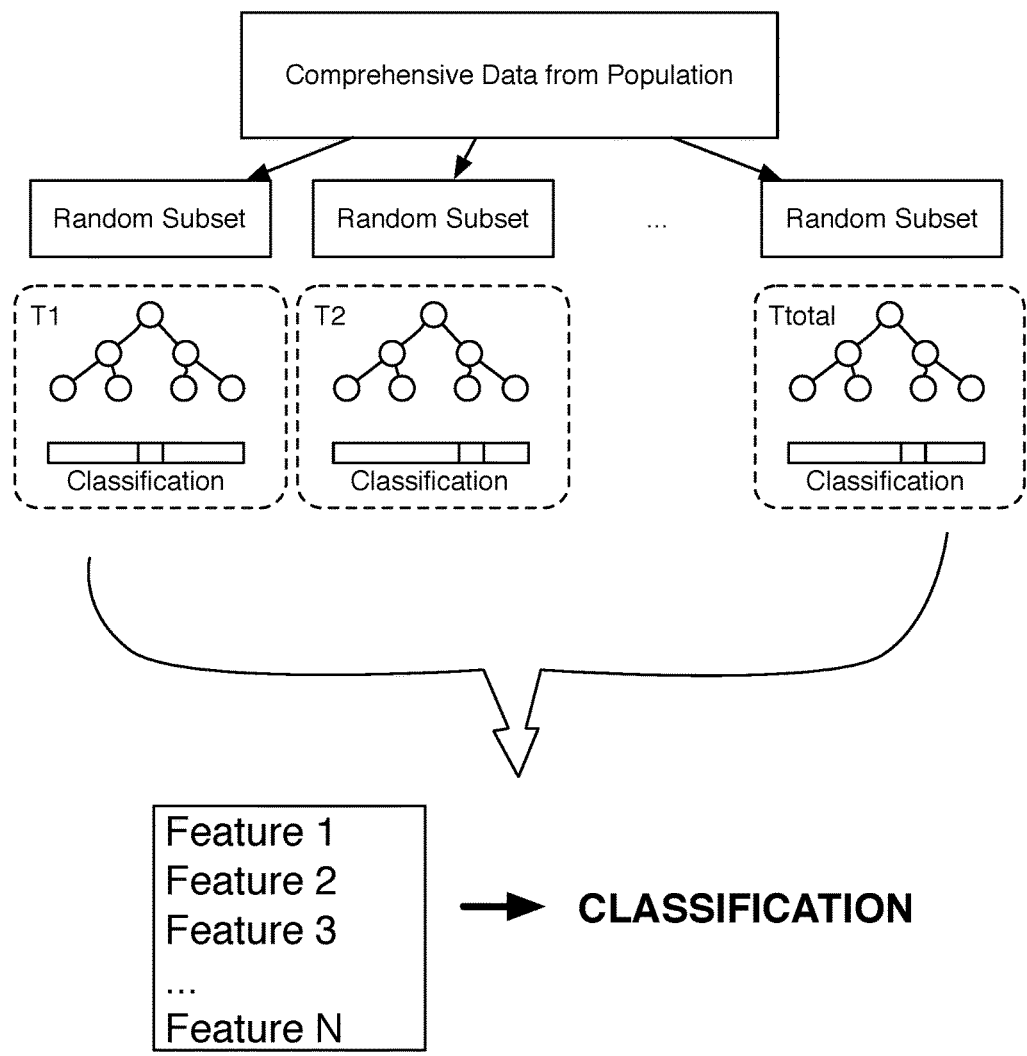
Figure 15A:
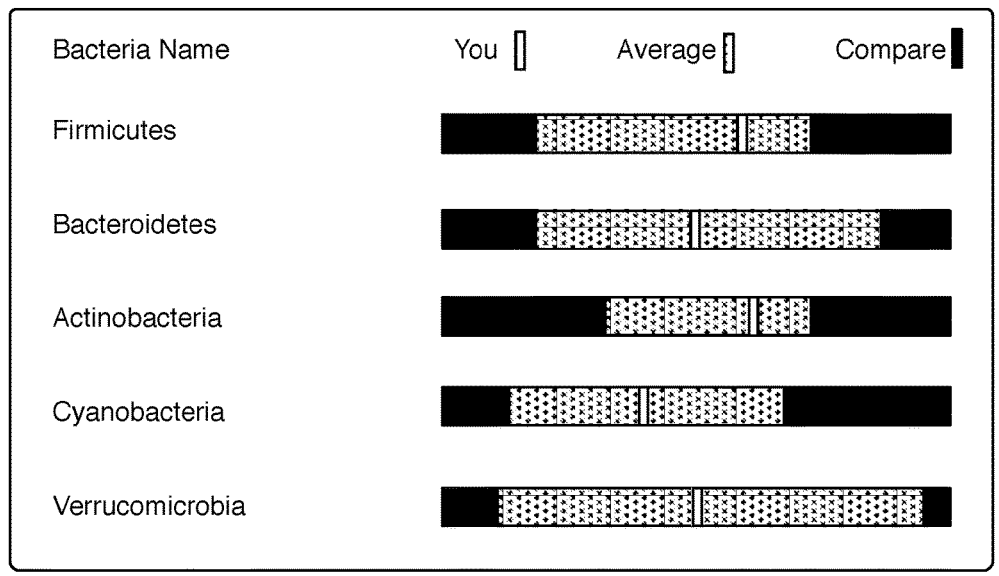
Figure 15B:
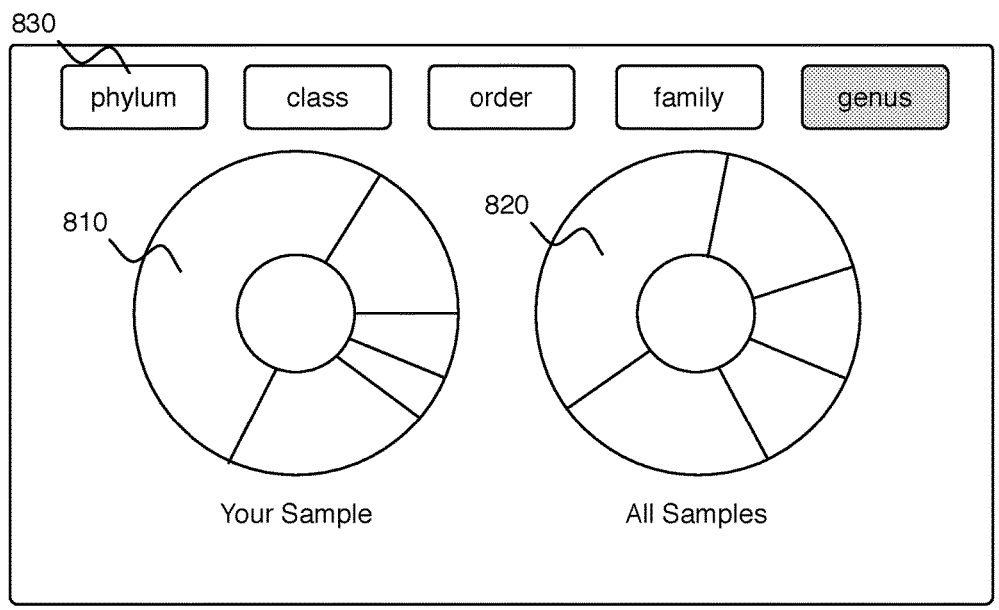
Figure 15C:
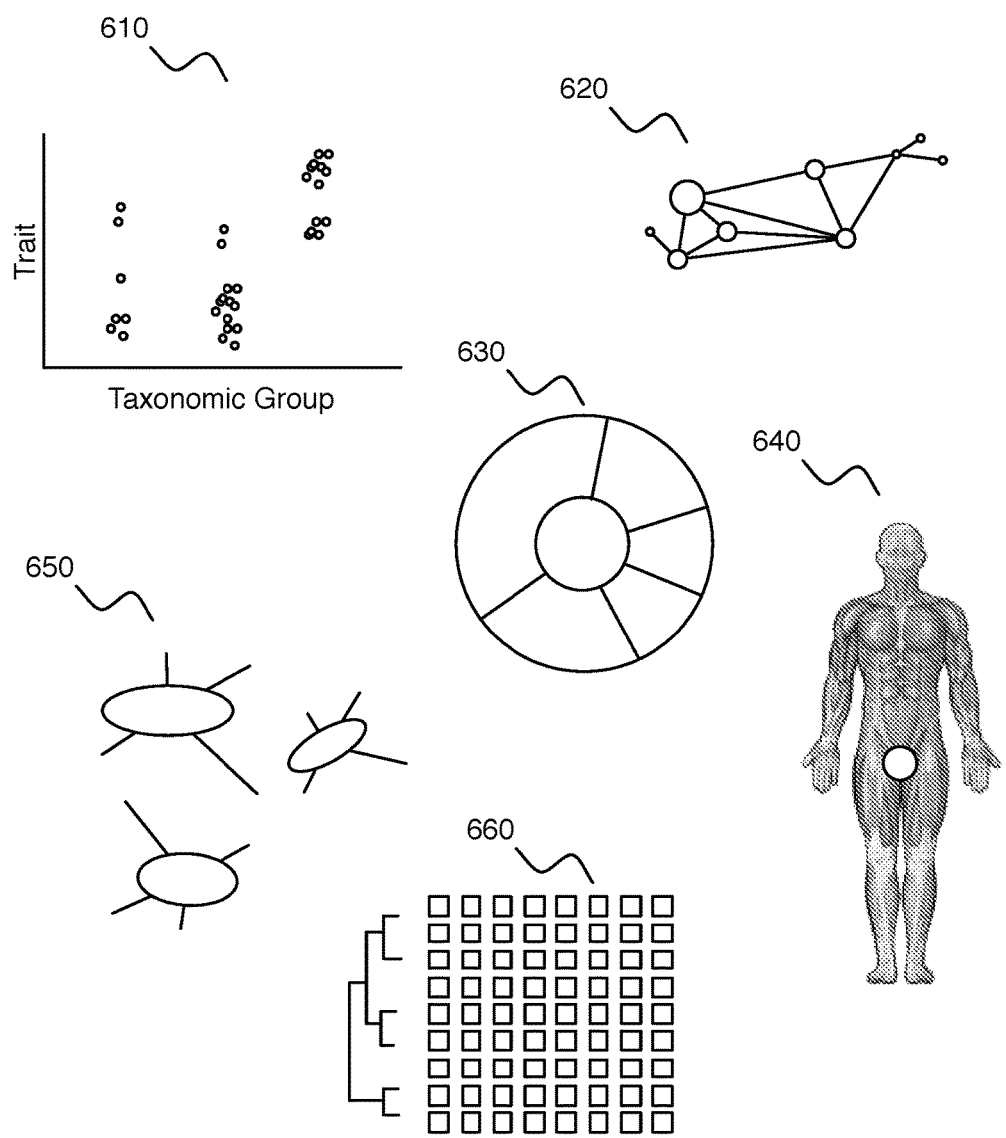
Figure 15D:
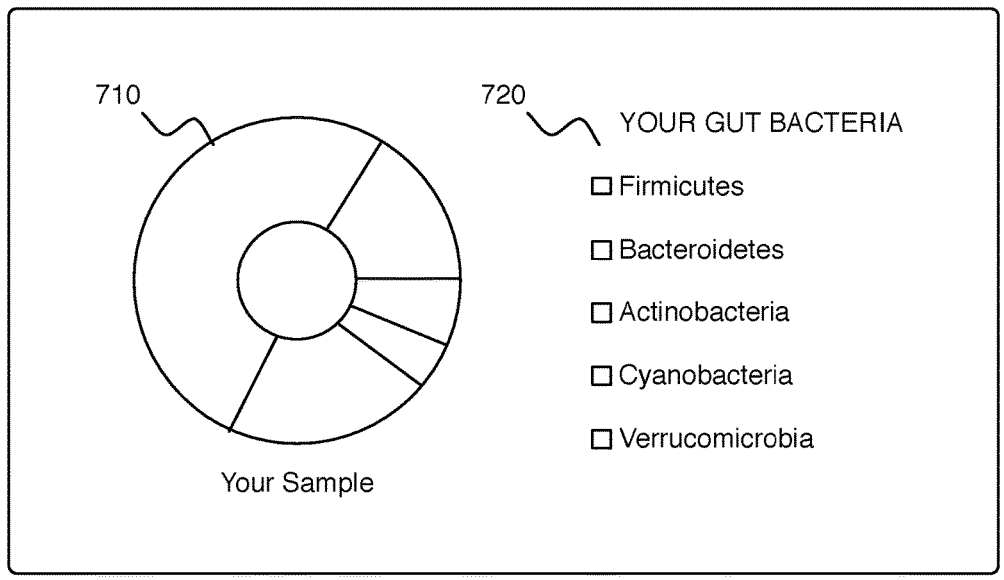
Figure 15E:
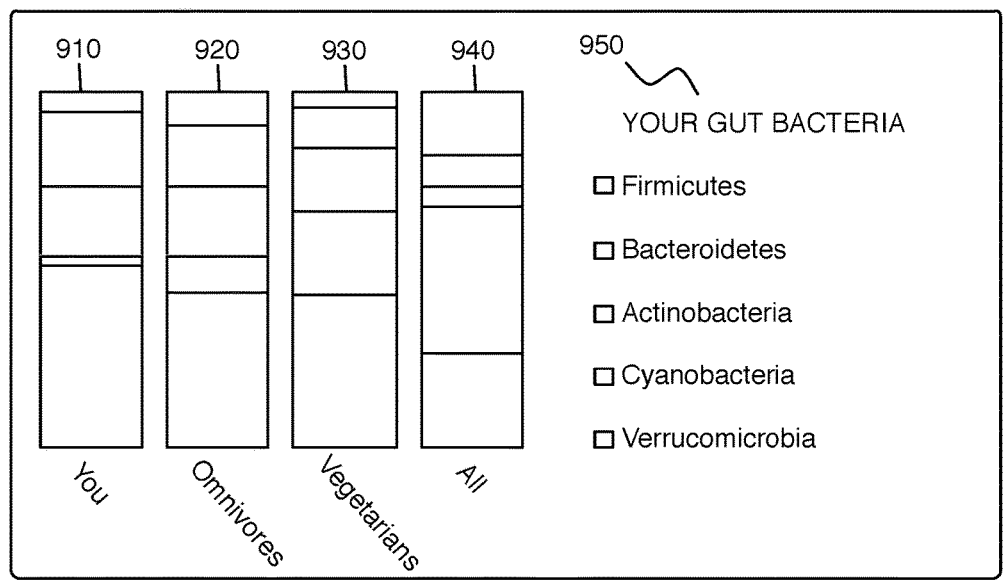
Figure 15F:
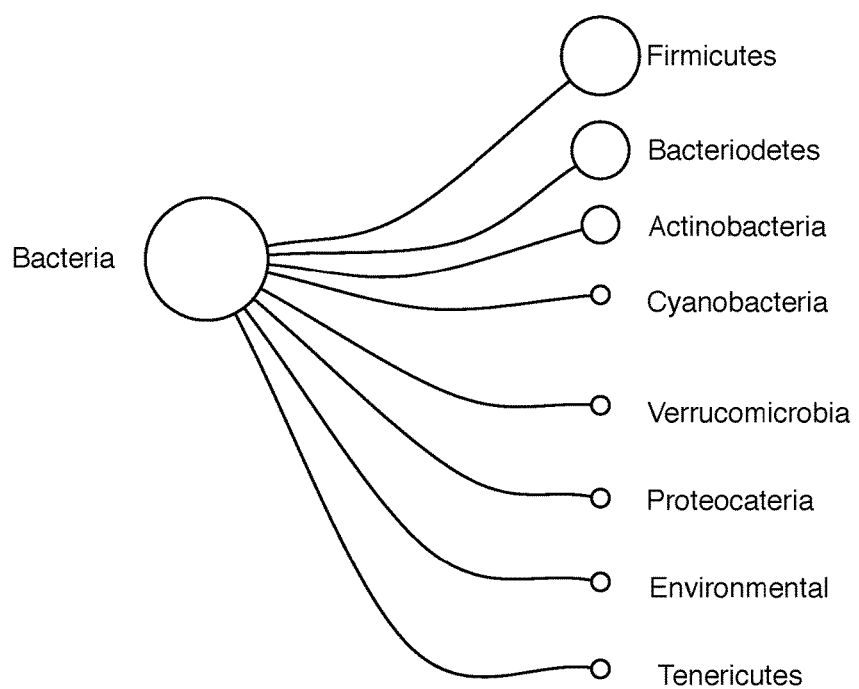
Figure 16:
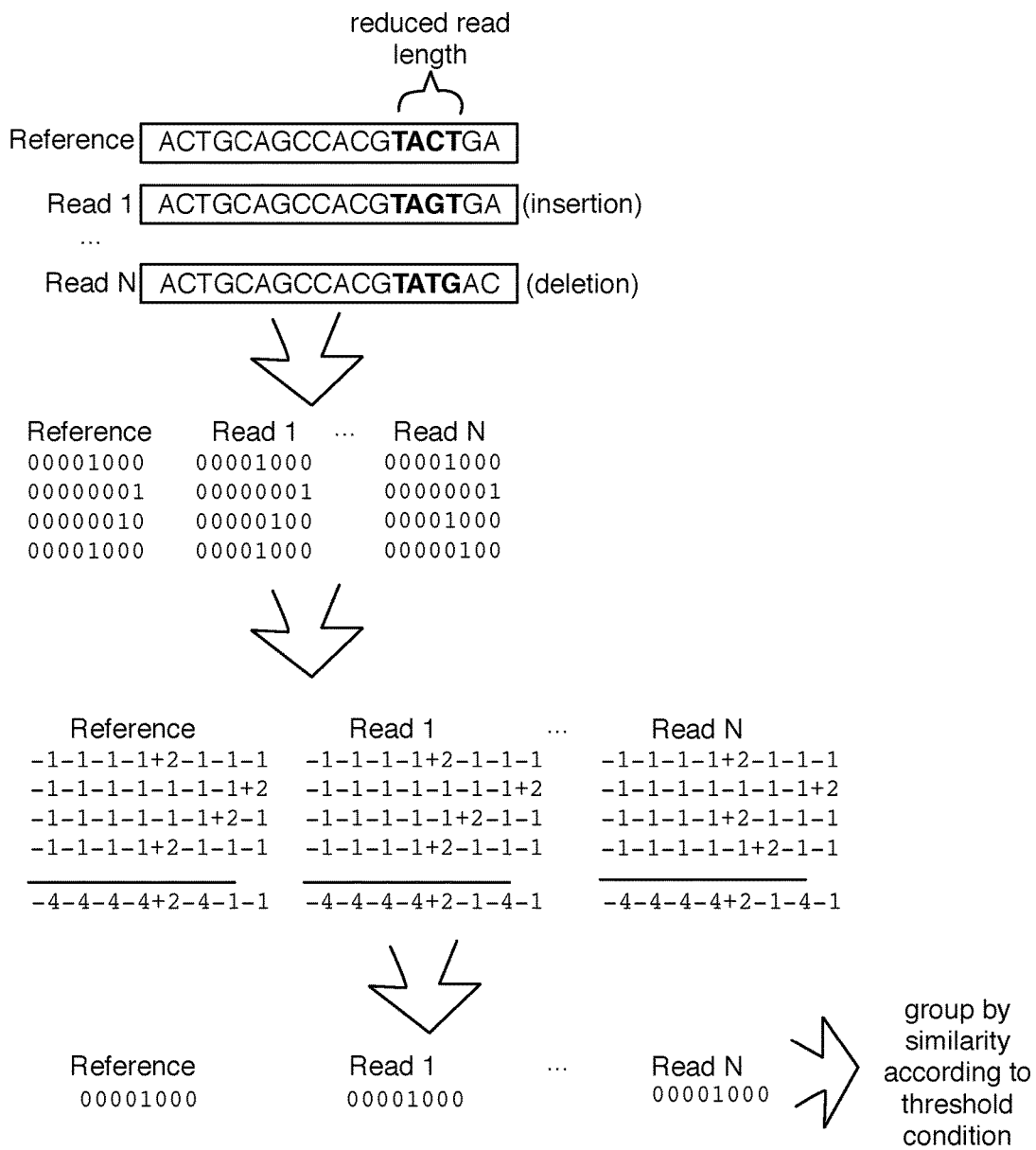

TABLES 1-4 depict specific examples of primers and barcode sequences used in an embodiment of a method for performing microbiome analysis;

FIG. 6 is a schematic of a variation of a portion of a system for performing microbiome analysis;

FIG. 7A is a flowchart of a variation of a portion of a method for performing multiplex analysis in a method for performing microbiome analysis;

FIG. 7B is a schematic of elements used in a method for performing multiplex analysis;

FIG. 8 is a flowchart of a variation of a portion of a method for performing microbiome analysis;

FIG. 9A is a flowchart of a variation of a portion of a method for performing microbiome analysis;

FIG. 9B is a schematic of a variation of a portion of a system for performing microbiome analysis;

FIG. 10 is a flowchart of a variation of a portion of a method for uniquely identifying samples in a method for performing microbiome analysis;

FIGS. 11A and 11B depict aspects of a variation of a portion of a method for uniquely identifying samples and quantifying nucleic acid content in a method for performing microbiome analysis;

FIG. 12 is a flowchart of a variation of a portion of a method for performing microbiome analysis;

FIG. 13 is an example of a survey, provided by way of a social networking system, in a variation of a method for performing microbiome analysis;

FIG. 14 is a schematic of a portion of a method for performing microbiome analysis;

FIGS. 15A-15F depict examples of visualization tools and user interfaces for providing microbiome-derived insights to individuals in an embodiment of a method and system for performing microbiome analysis; and FIG. 16 depicts an example of a hashing operation in an embodiment of a method and system for performing microbiome analysis.

DESCRIPTION OF THE EMBODIMENTS

The following description of the embodiments of the invention is not intended to limit the invention to these embodiments, but rather to enable any person skilled in the art to make and use this invention.

1. Method and System

Figure 1A:
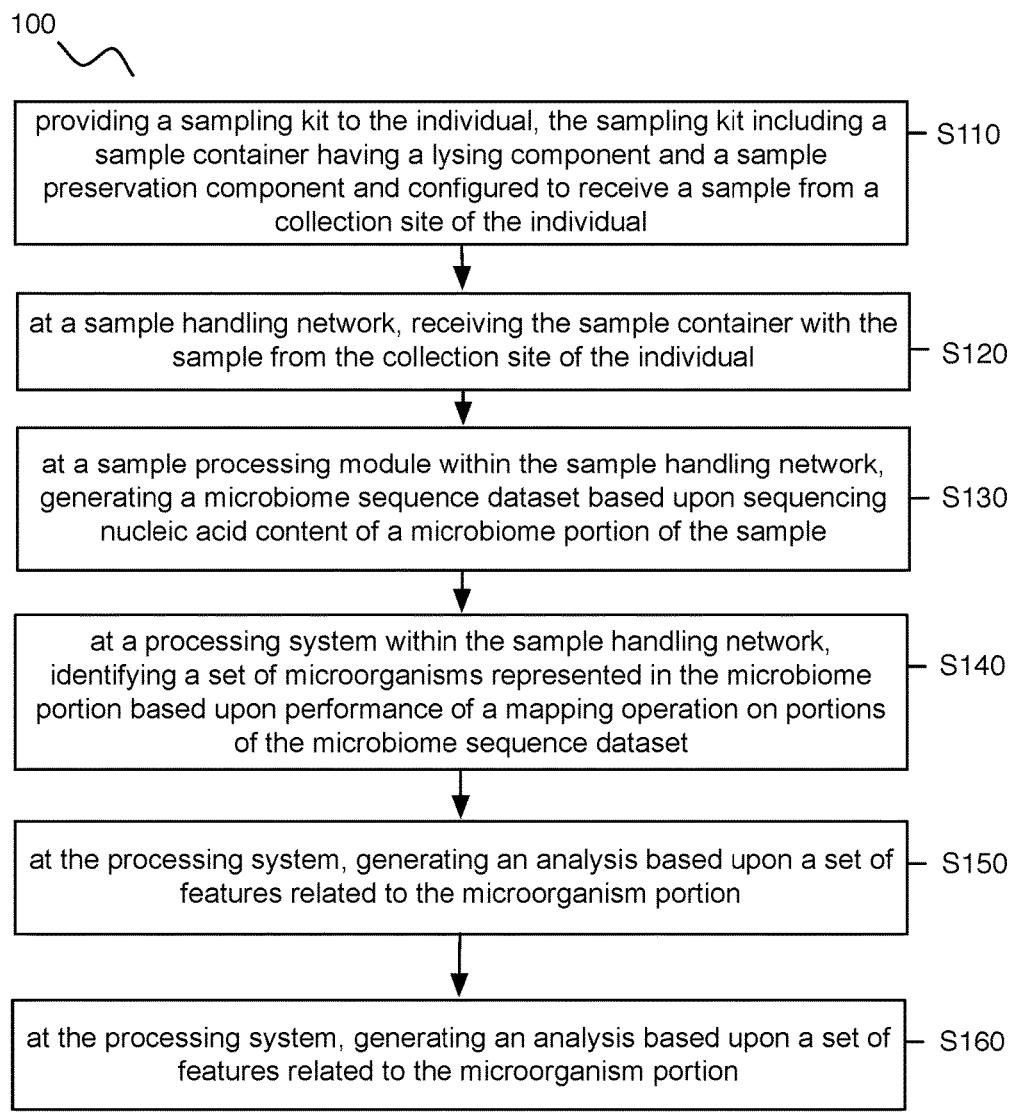
FIG. 1A is a flowchart of an embodiment of a method for performing microbiome analysis.

As shown in FIG. 1A, a method 100 for analyzing a microbiome of an individual comprises: providing a sampling kit to the individual, the sampling kit including a sample container having a process reagent component and configured to receive a sample from a collection site of the individual S110; at a sample handling network, receiving the sample container with the sample from the collection site of the individual S120; at a sample processing module within the sample handling network, generating a microbiome sequence dataset based upon sequencing nucleic acid content of a microbiome portion of the sample S130; at a processing system within the sample handling network, identifying a set of microorganisms represented in the microbiome portion based upon performance of a mapping operation on portions of the microbiome sequence dataset S140; at the processing system, generating an analysis based upon a set of features related to the microorganism portion S150; and from the processing system, transmitting information derived from the analysis to the individual S160.

Figure 1B:
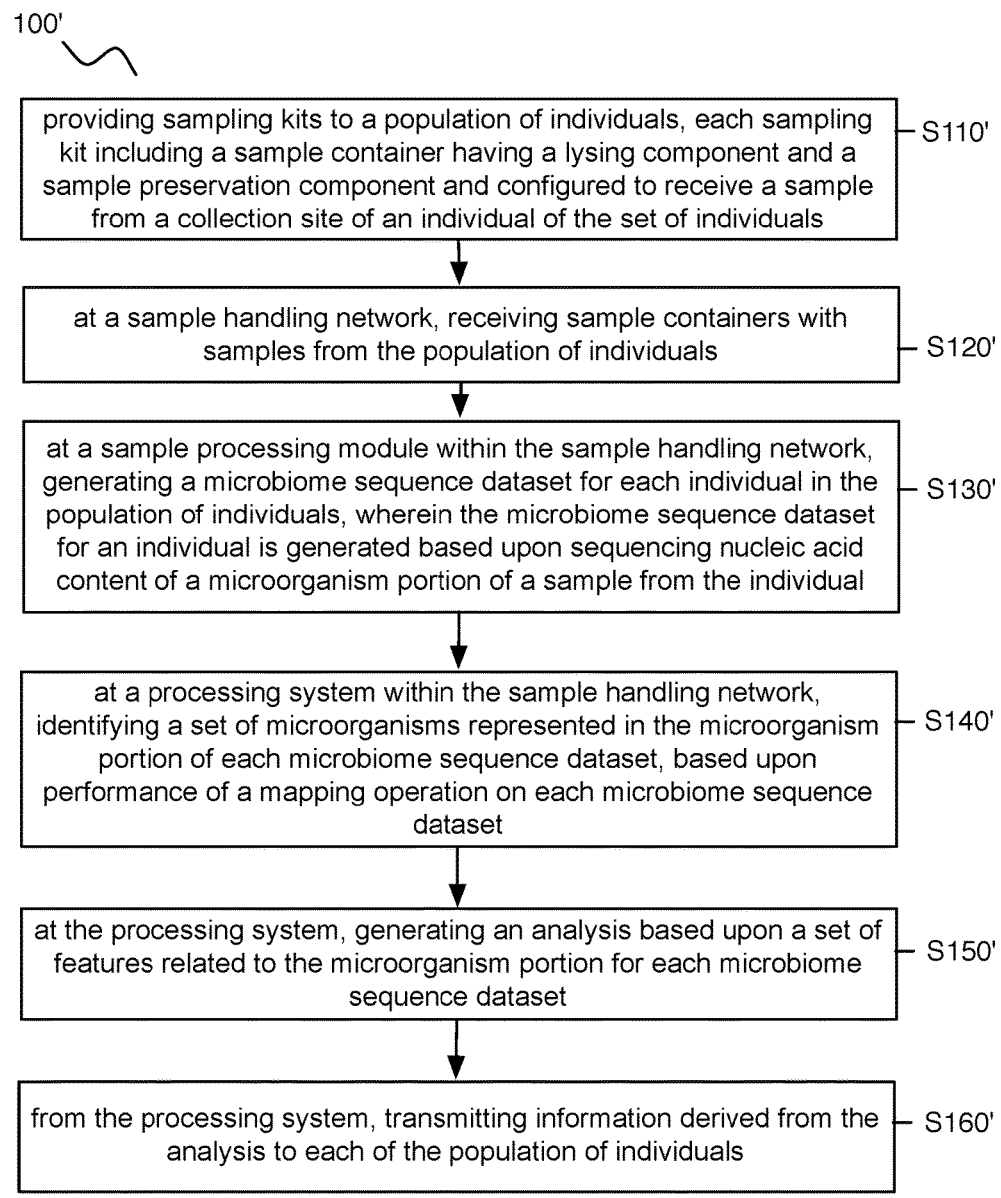
FIG. 1B is a flowchart of an embodiment of a method for performing microbiome analysis for a population of individuals.

The method 100 is preferably configured to be expanded to a population of individuals, as shown in FIG. 1B, such that an expanded method 100' can include: providing sampling kits to a population of individuals, each sampling kit including a sample container having a lysing component and a sample preservation component and configured to receive a sample from a collection site of an individual of the set of individuals S110'; at a sample handling network, receiving sample containers with samples from the population of individuals S120'; at a sample processing module within the sample handling network, generating a microbiome sequence dataset for each individual in the population of individuals, wherein the microbiome sequence dataset for an individual is generated based upon sequencing nucleic acid content of a microorganism portion of a sample from the individual S130'; at a processing system within the sample handling network, identifying a set of microorganisms represented in the microorganism portion of each microbiome sequence dataset, based upon performance of a mapping operation on each microbiome sequence dataset S140'; at the processing system, generating an analysis based upon a set of features related to the microorganism portion for each microbiome sequence dataset S150'; and from the processing system, transmitting information derived from the analysis to each of the population of individuals S160'.

The method 100 functions to generate and provide insights derived from compositional aspects of the microbiomes of one or more individuals, and to provide means for efficient sample reception and processing from the individual(s). In variations, blocks of the method 100 can be configured to guide the sample provision and/or reception process for individuals who are at locations remote from a sample handling network, can be configured to enable unique identification of individual samples collected from a population of individuals, mitigate or prevent sample contamination (e.g., cross contamination, etc.), and/or can be configured to more efficiently process samples in a multiplex manner. Insights derived from outputs of the method 100 can also be used to classify individuals based upon microbiome-based analyses conducted at an individual and/or a population level.

Figure 2:
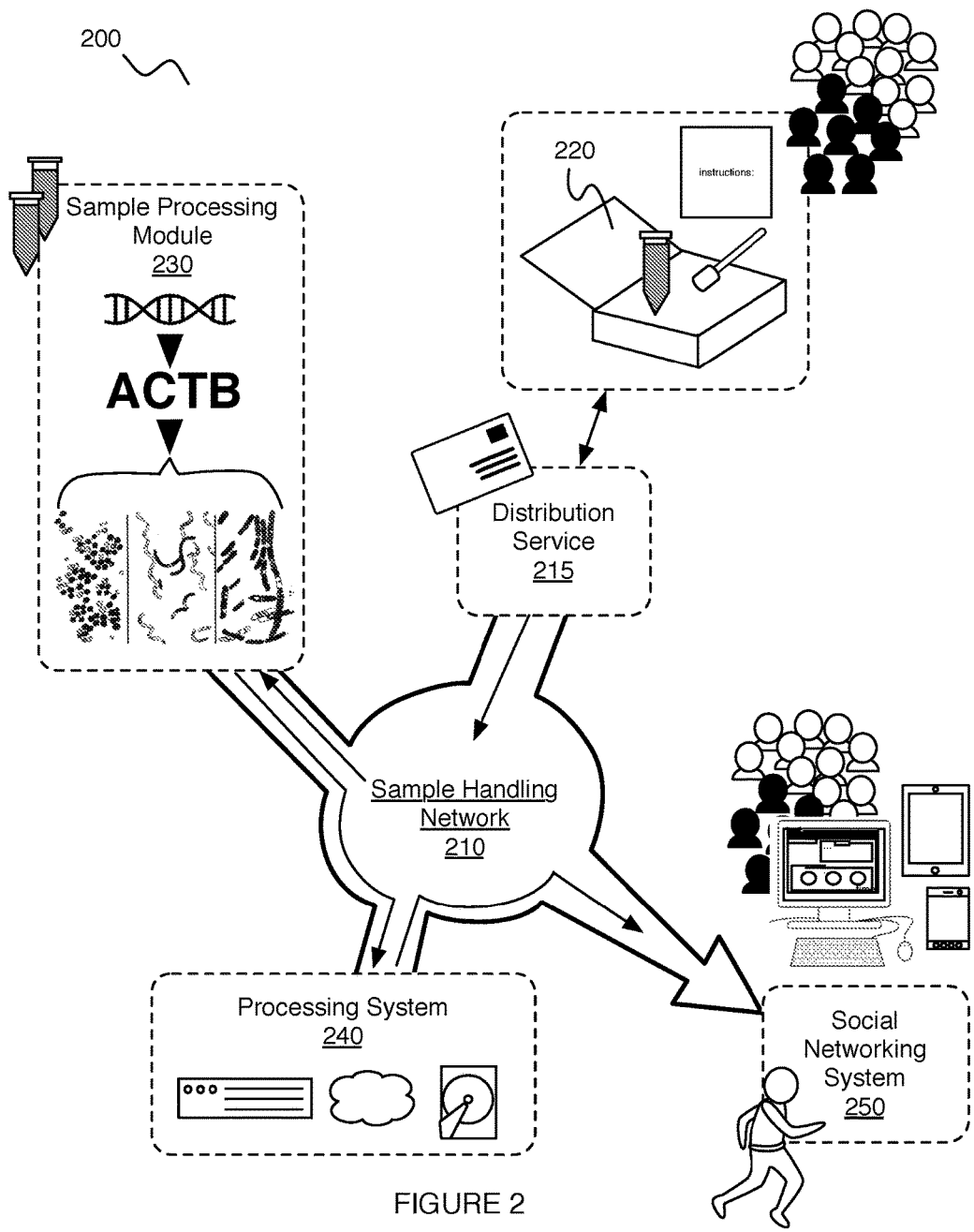
FIG. 2 is a schematic of an embodiment of a system for performing microbiome analysis.

In one application, the method 100 is implemented at least in part at a system 200, as shown in FIG. 2, including a sample handling network 210 that facilitates provision of sampling kits 220 to individuals using a distribution service 215, receives biological samples from the individuals by way of the sample reception kit, processes the biological samples at a sample processing module 230 within the sample handling network, performs microbiome-based analyses on sequenced nucleic acid content of the biological samples at a processing system 240 within the sample handling network, and transmits information derived from the microbiome-based analyses to individuals in cooperation with a social networking system 250. The method 100 can, however, alternatively be implemented using any other suitable system(s) configured to receive and process microbiome-related data of users, in aggregation with other information, in order to generate and share insights derived from microbiome-based analyses conducted at individual and/or population-wide levels.

1.1 Sample Provision

Block S110 recites: providing a sampling kit to the individual, the sampling kit including a sample container having a process reagent component and configured to receive a sample from a collection site of the individual. Block S110 functions to provide a mechanism by which an individual, who is at a location remote from a sample handling network, can provide samples in a dependable manner. In Block S110, providing the sampling kit is preferably performed using a parcel delivery service (e.g., postal service, shipping service, mailing service, etc.) accessible to the sample handling network, such that the sample handling network can provide the sampling kit(s) to one or more individuals over the parcel delivery service. Additionally or alternatively, the sampling kit can additionally or alternatively be provided directly through an entity associated with the sample handling network, wherein the entity is also trained to facilitate sample reception from an individual. In examples, the entity can be any one or more of: a clinical technician, a laboratory technician, a healthcare professional (e.g., doctor, nurse, etc.), and any other suitable entity that can facilitate provision of the sampling kit to an individual or facilitate reception of a sample from the individual by way of the sampling kit. However, provision of the sampling kit(s) to the individual(s) in Block S110 can additionally or alternatively be performed in any other suitable manner.

The sampling kit(s) provided in Block S110 are preferably configured to facilitate reception of samples from individuals in a non-invasive manner. In variations, non-invasive manners of sample reception from an individual can use any one or more of: a permeable substrate (e.g., a swab configured to wipe a region of an individual's body, toilet paper, a sponge, etc.), a non-permeable substrate (e.g., a slide, tape, etc.) a container (e.g., vial, tube, bag, etc.) configured to receive a sample from a region of an individual's body, and any other suitable sample-reception element. In a specific example, samples can be collected from one or more of an individual's nose, skin, genitals, mouth, and gut in a non-invasive manner (e.g., using a swab and a vial). However, the sampling kit(s) provided in Block S110 can additionally or alternatively be configured to facilitate reception of samples in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples from individuals can comprise one or more of: blood samples, plasma/serum samples (e.g., to enable extraction of cell-free DNA), and tissue samples.

Figure 3:
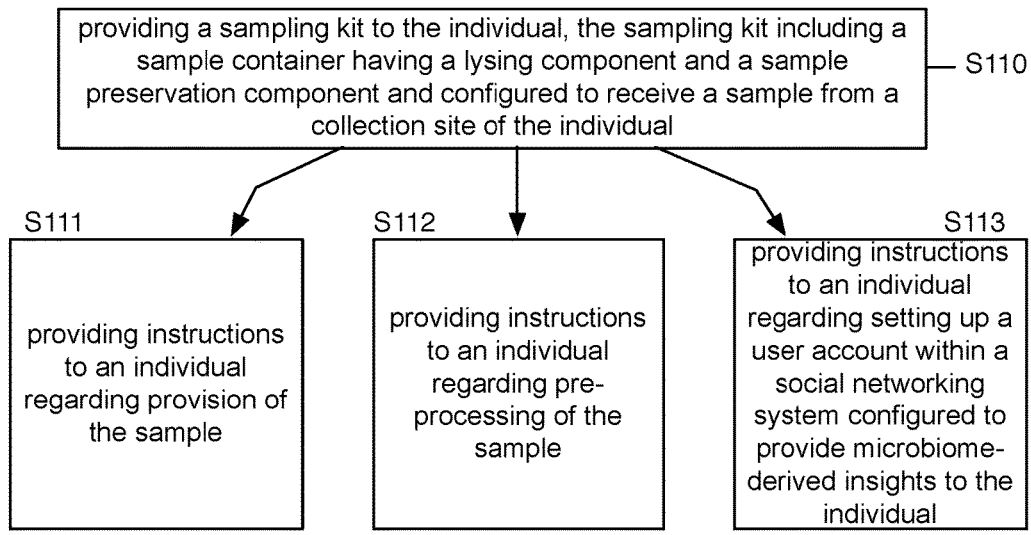
FIG. 3 is a flowchart of a variation of a portion of a method for performing microbiome analysis.

In Block S110, providing the sampling kit to an individual can further include one or more of: providing instructions to an individual regarding provision of the sample S111, providing instructions to an individual regarding pre-processing of the sample S112, and providing instructions to an individual regarding setting up a user account within a social networking system configured to provide microbiome-derived insights to the individual S113, as shown in FIG. 3. Blocks S111, S112, and S113 function to guide a remote individual in providing one or more samples in a dependable manner, guide a remote individual in performing some aspects of sample pre-processing (e.g., with the individual's acknowledgement, in a surreptitious manner without the individual's acknowledgement), and guide a remote individual in setting up a personalized account at which the individual can receive information related to his/her microbiome, respectively.

In variations of Block S111, providing instructions regarding provision of the sample can include one or more of: providing sample provision instructions specific to one or more of a set of collection sites of the body of an individual, providing instructions pertaining to an amount of sample to be provided by the individual, providing instructions pertaining to time(s) of day at which to provide samples, providing instructions pertaining to behaviors that should be avoided prior to and/or during sample provision, providing instructions pertaining to behavior that are encouraged prior to and/or during sample provision, providing instructions regarding correction of an improperly provided sample, providing instructions regarding storage of a sample prior to transmission to a sample handling network (e.g., with regard to temperature ranges at which to store a sample, with regard to orientation of a sample container, with regard to motion of a sample container, etc.), instructions regarding transmission of a sample to a sample handling network, and provision of any other suitable instructions related to sample provision.

In a specific example of Block S111, instructions for sample provision can be provided for collection sites associated with the gut, the skin, the mouth, the nose, the male genitals, and the female genitals. With regard to the gut, instructions for sample provision in the specific example include swabbing used toilet paper to collect a small amount of feces (e.g., enough to change the color of the swab). With regard to the skin, instructions for sample provision in the specific example include wetting a swab provided in the sampling kit with polymerase chain reaction (PCR) water provided in the sampling kit, and wiping the wetted swab along the lower half of the crease behind the ear for one minute (e.g., while pulling the ear forward or pulling hair out of the way, if necessary). With regard to the mouth, instructions for sample provision in the specific example include swabbing the inside of each cheek vigorously for 30 seconds, without touching the swab to the teeth or gums. With regard to the nose, instructions for sample provision in the specific example include wetting a swab provided in the sampling kit with polymerase chain reaction (PCR) water provided in the sampling kit, and wiping the wetted swab within each nostril at the depth of the swab for 30 seconds. With regard to the male genitals, instructions for sample provision in the specific example include wetting a swab provided in the sampling kit with polymerase chain reaction (PCR) water provided in the sampling kit, and wiping the wetted swab in a circular motion around the base of the head of the penis for one minute (e.g., with pulling back of the foreskin, if necessary). With regard to the female genitals, instructions for sample provision in the specific example include wetting a swab provided in the sampling kit with polymerase chain reaction (PCR) water provided in the sampling kit, and wiping the wetted swab in the area just inside the vaginal opening, to the depth of cotton on the swab, for one minute (e.g., with spreading of the labia using the hand not performing the swabbing motion).

In the specific example of Block S111, provided instructions include instructions to avoid sample contamination (e.g., by advising an individual to place caps of sample containers upside down in order to avoid transmitting a contaminant into the interior of the sample container). In the specific example, provided instructions further include instructions to avoid bathing or bringing substances that might disturb the microbiome into contact with a sample site for at least 8 hours prior to sample provision by an individual. In the specific example, the instructions further advise against contact with antiseptics antibiotic soaps, and lotions, and behaviors such as teeth brushing, using mouthwash, kissing, sex, hot tubbing, eating, swimming, and any behaviors that could disturb the microbiome of the individual. In the specific example, instructions include instructions regarding packaging of sample containers including collected samples prior to transmission to a sample handling network (e.g., using a parcel delivery service), and first aid instructions in the event of inappropriate usage. Variations of the specific example of Block S111 can, however, include any other suitable instructions related to sample provision.

In variations of Block S112, providing instructions regarding pre-processing of the sample can include one or more of: instructions pertaining to lysis of cells of a provided sample, instructions pertaining to incubation of cells of a provided sample, instructions pertaining to mixing a provided sample with process reagents prior to transmission to a sample handling network, and any other suitable instructions related to pre-processing of a biological sample. In a specific example of Block S112, the individual providing the sample is instructed to combine a sample on a swab with process reagents pre-packaged in a sample container provided by the sampling kit, by stirring the swab within the sample container for a minute without splashing contents of the sample container. In the specific example of Block S112, the individual is further instructed to shake the sample container with the process reagents and the sample for one minute, in order to begin a process of cell lysing within the sample and nucleic acid extraction from the sample. In Block S112, instructing the individual in pre-processing the sample can be conducted in an open manner wherein the individual is aware that he/she is involved in the sample pre-processing process, or alternatively in a surreptitious manner with the individual unaware that he/she is involved in the sample pre-processing process.

In variations of Block S113, providing instructions regarding setting up a user account within a social networking system configured to provide microbiome-derived insights to the individual can include providing a uniform resource locator (URL) or other internet address by which an individual can set up an account within an online social networking system. Provision of an address can be performed using a messaging client (e.g., a text messaging client, an email messaging client, etc.), using textual-based instructions provided within the sampling kit, using a machine-decodable tag (e.g., a QR code, a barcode, an antenna associated with a near field communication device, etc.), and/or in any other suitable manner. Instructions provided in association with Block S113 can further include instructions regarding initialization of an account (e.g., by providing a user name and a password), instructions regarding provision of personal information, instructions regarding associating a user account with an identifying aspect (e.g., registration ID) of a sampling kit, and any other suitable instructions. Information needed from the individual in setting up the user account can, in Block S113, be directly input by individual (e.g., using an input device of an electronic device associated with the individual), and can additionally or alternatively be automatically populated based upon accessing information databases associated with the individual. For instance information needed in setting up the user account can be populated upon accessing of an electronic health record (EHR) and/or a social network accounts (e.g., Facebook account, LinkedIn account, Twitter account, etc.) associated with the individual, upon receiving permission from the individual.

In any one or more of Blocks S111, S112, and S113, instruction provision can include one or more of: text-based instruction provision, picture-based instruction, video-based instruction provision, audio-based instruction provision, touch/haptic-based instruction provision, and any other suitable form of instruction provision. For instance, Blocks S111, S112, and/or S113 can include providing text and picture-based instructions on a card included with the sampling kit, or instructions included with an electronic storage device (e.g., memory card, disk, etc.). Additionally or alternatively, Block S113 can facilitate the instruction provision process, whereby text, picture, audio, and/or video-based instructions can be provided through the user account of the social networking system. For instance, once an individual has logged into his/her user account at an electronic device including input devices (e.g., a keyboard, a touch screen, a mouse, a touch pad, a microphone, a camera, etc.) and output devices (e.g., a display, a speaker, a vibration module, etc.), the electronic device can facilitate instruction provision as the individual interfaces with the social networking system.

As noted above, Block S110 is preferably implemented by way of a system 200, as shown in FIG. 2, that includes a sample handling network 210 that facilitates provision of sampling kits 220 to individuals. The sample handling network 210 thus functions as a platform from which sampling kits can be distributed to individuals who are remote from the sample handling network, and to which sample containers including samples from individuals can be returned for processing and analysis. One aspect of the sample handling network 210 thus functions as a distribution and receiving hub for biological sample handling, wherein individuals are able to transmit samples directly to the sample handling network without requiring direct contact between individuals and a clinical or laboratory-based intermediary staffed with trained personnel for biological sample handling. The sample handling network 210 is thus preferably configured to provide instructions directly to individuals pertaining to sample provision in a dependable manner without involving laboratory-trained personnel in the sample provision process, and is preferably configured to associate samples with individuals providing the samples in a secure and reliable manner that is compliant with regulatory standards (e.g., compliant with the Health Insurance Portability and Accountability Act, HIPAA). However, the sample handling network 210 can alternatively be configured to distribute sampling kits 220 and/or receive samples from individuals using a laboratory-based or clinical-based intermediary, and/or handle samples in any other suitable manner.

The sampling kit(s) 220 provided by way of the sample handling network 210 preferably include at least sample extraction element (e.g., permeable substrate, non-permeable substrate, swab, toilet paper, sponge, lancet, needle, syringe, etc.), at least one sample container (e.g., sample chamber, vial, well, etc.), instructions (e.g., as described in relation to Blocks S111, S112, and S113 above), sample provision reagents, sample process reagents, and features configured to facilitate association of the sampling kit and sample container(s) of the sampling kit with an individual providing the sample(s). In variations, the process reagent components can include a lysing component (e.g., beads, lysing reagents, etc.) and a sample preservation component; however, in other variations, the process reagent can include any other suitable process reagent that facilitates sample handling. The sampling kit(s) also preferably include packing elements that enable the individual to transmit a provided sample to the sample handling network 210. The sampling kit(s) 220 can additionally or alternatively include elements that prevent sample contamination (e.g., sample isolation elements), elements that promote hygiene of the individual post-provision of a sample (e.g., alcohol wipes, antibacterial wipes, lotions, soaps, etc.), and/or any other suitable elements that facilitate an individual prior to, during, and/or post provision of a sample.

Figure 4A:
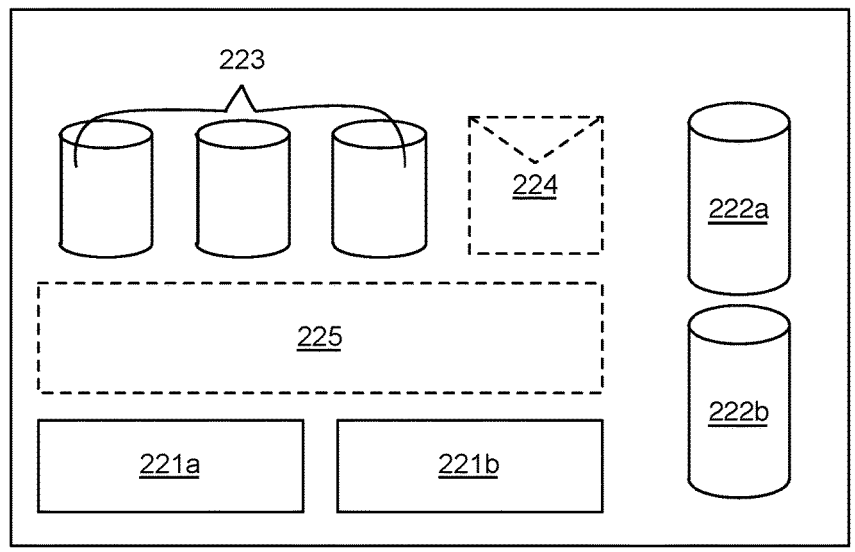
FIG. 4A is a schematic of a variation of a sampling kit in a method and system for performing microbiome analysis.

As such, in one variation, as shown in FIG. 4A, the sampling kit 220 can include a permeable substrate 221 (e.g., a swab) configured to facilitate extraction of a sample from a dedicated collection site of the individual's body (or an object that contacts the individual), and a sample process reagent (e.g., PCR water) configured to permeate the permeable substrate 221 in variations wherein a wetted permeable substrate would facilitate sample extraction from an individual. In the variation, the permeable substrate(s) 221 and the sample process reagent are preferably packaged in a sterile manner, in order to avoid sample contamination. In a specific example, the sampling kit 220 includes a set of swabs as permeable substrates 221, wherein each swab is sealed in a container in a sterile manner. In the specific example, the sampling kit 220 further includes a set of vials 222 of a PCR water for wetting one or more swabs of the set of swabs, wherein each vial is also sealed, prior to use by the individual, in a sterile manner.

Figure 4B:
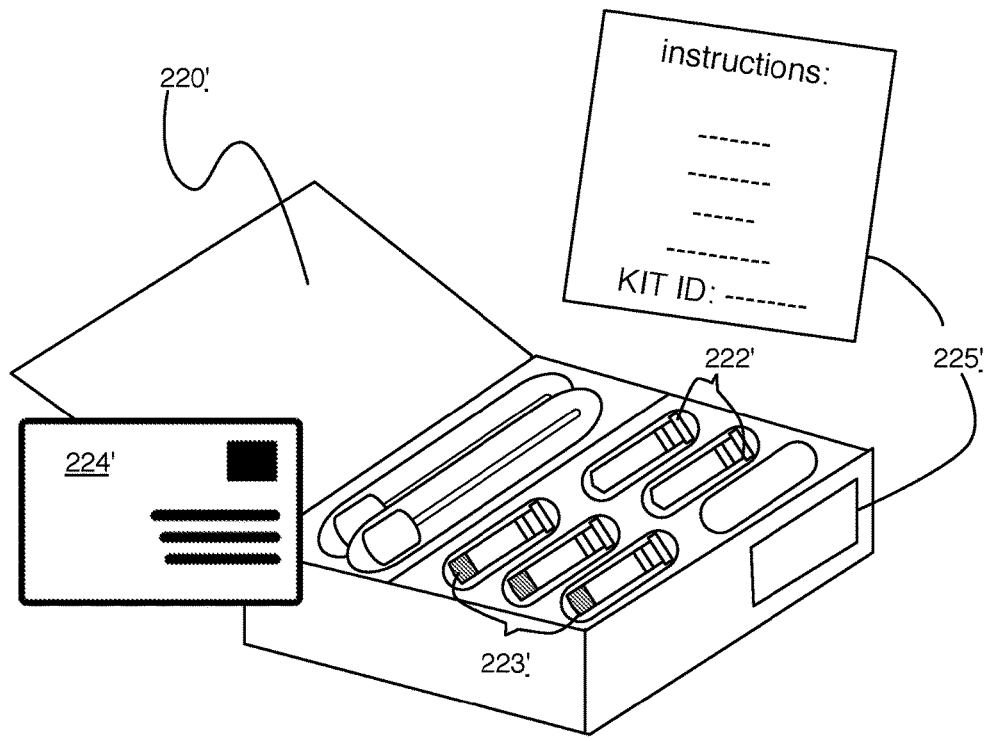
FIG. 4B is a schematic of a specific example of a sampling kit in a method and system for performing microbiome analysis.

Variations of the sample container(s) 223 provided with the sampling kit 220 can include sample chambers, vials, well-plates, and/or any other suitable sample containing element. A sample container 223 provided with the sampling kit 220 is preferably configured to have a sufficient volume for reception of a sample (e.g., by way of a permeable substrate), and/or mixing of the sample with sample processing reagents within the sample container 223. Additionally, a sample container 223 provided with the sampling kit 220 can be pre-packaged with sample processing reagents (e.g., sample lysis beads, sample lysis reagents, nucleic acid amplification reagents), and/or sample preservation reagents (e.g., reagents for preservation of nucleic acids). Additionally or alternatively, sample containers and/or any other suitable element of the sampling kit 220 can facilitate sample handling processes associated with one or more of: sample freezing (e.g., cryogenic freezing), sample lyophilization, active culture of a sample, and any other suitable downstream sample handling process. Furthermore, sample containers 223 provided in the sampling kit 220 can include unique identifying features (e.g., colors, textures, shapes, labels, etc.) associated with collection sites of the individual, that enable the individual to provide a sample within the correct sample container 223 with a reduced chance of error. In a specific example, as shown in FIG. 4B, the sampling kit 220' includes a set of color-coded vials (i.e., color coded and labeled according to collection site) as sample containers 223' for sample reception, wherein each vial includes Tris(hydroxymethyl)aminomethane (e.g., at a concentration of ≤1.8%) for buffering a sample, sodium chloride (e.g., at a concentration of ≤8%), Edetate disodium dehydrate (e.g., at a concentration of ≤18.6%) as a chelating agent, and guanidine thiocyanate (e.g., at a concentration of ≤2M) as a chaotropic agent for solubilizing cells. Variations of the specific example can additionally or alternatively include additional reagents for sample preservation, reagents that prepare the sample for further processing (e.g., reagents for amplification), and/or any other suitable reagents.

In variations wherein portions of the sampling kit 220 for sample reception (e.g., sample containers 223) are configured to be delivered back to the sample handling network 210, the sampling kit 220 can further include a packaging receptacle 224 (e.g., a bubble mailer, an envelope, a parcel, etc.), with or without postage for delivery to the sample handling network 110. Additionally or alternatively, portions of the sampling kit can be configured to be picked up by a courier service specifically associated with the sample handling network (e.g., using a staff of couriers configured to be contacted when a sample from an individual is ready to be picked up), wherein the individual is given instructions to contact the courier service once provision of a sample is complete. The sample delivery process can, however, be facilitated by the sampling kit 220 in any other suitable manner.

Identifying features 225 of the sampling kit 220 can include one or more of: a registration code of characters (e.g., alphanumeric characters), a biological identifier (e.g., a nucleic acid marker with a specific sequence and/or a specific concentration), a machine-readable tag (e.g., QR code, barcode, antenna detectable using a near field communication device, etc.), and any other suitable identifier. Furthermore, the sampling kit 220 can include or be configured to facilitate instruction provision to an individual, as described in relation to Blocks S111, S112, and S113 above. Variations of elements of the sampling kit 220 configured for instruction provision can include printed materials and/or digitally stored information (e.g., information stored in memory), and/or can comprise a link, code, or reference to digitally-stored information (e.g., a link to a program, a file, or an application). In some variations, the sampling kit can be configured to facilitate instruction provision by way of an electronic device associated with the individual. For instance, a QR code of the sampling kit 220 can be scanned using an electronic device of the individual, wherein the QR code links to an address that includes text and visual instructions for sample provision. In another example, a printed card in the sampling kit 220 can include a URL at which instructions for sample provision are provided to the individual. Identifying features and elements of the sampling kit 220 associated with instruction provision can, however, be configured in any other suitable manner.

Variations of the sampling kit(s) 220 and/or the sample handling network 210 can, however, comprise any other suitable elements and/or be configured in any other suitable manner.

1.2 Sample Reception

Block S120 recites: at a sample handling network, receiving the sample container with the sample from the collection site of the individual, which functions to enable generation of data from which microbiome-based insights for an individual and/or for a population of individuals can be derived. As noted above, reception of sample containers in Block S120 can be facilitated using one or more of a parcel delivery service and a courier service, or can alternatively be directly enabled with delivery of a sample container to the sample handling network by the individual associated with the sample container. Furthermore, samples received in Block S120 can be in a pre-processed state of lysing (i.e., due to agitation of a sample by an individual in Block S110), or can alternatively be in any other suitable state upon reception at the sample handling network.

In Block S120, an aggregate set of samples is preferably received from a wide variety of individuals, using an aggregate set of sampling kits provided to the individuals by way of the sample handling network. Preferably, the wide variety of individuals includes individuals of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), and any other suitable trait that has an effect on microbiome composition. As such, as the number of individuals increases, the power of insights generated in subsequent blocks of the method 100 increases, in relation to characterizing of a variety of individuals based upon their microbiomes. Additionally or alternatively, the samples received in Block S120 can include receiving biological samples from a targeted group of similar individuals in one or more of: demographic traits, health conditions, living situations, dietary habits, behavior tendencies, levels of mobility, and any other suitable trait that has an effect on microbiome composition, such that insights generated in subsequent blocks of the method 100 are insights targeted to specific groups of individuals. Preferably, the set of individuals from which samples are received includes individuals who do not have specific research training, clinical training, and/or laboratory training, such that the samples also represent non-trained individuals, who have been instructed in methods of providing samples in a dependable manner according to embodiments, variations, and examples of Block S110. However, Block S120 can alternatively include receiving samples from any suitable group of individuals, using any other suitable sample handling network-sample delivery service relationship.

In one such alternative variation, reception of sample containers with samples in Block S120 can be facilitated using a laboratory-based or a clinical-based intermediary that has staff trained in sample extraction from an individual and transmission of extracted samples to the sample handling network. However, reception of the sample at the sample handling network can be enabled in Block S120 in any other suitable manner.

1.3 Sample Processing—Amplification and Sequencing

Block S130 recites: at a sample processing module within the sample handling network, generating a microbiome sequence dataset based upon sequencing nucleic acid content of a microorganism portion of the sample. Block S130 functions to process each sample received in Block S120, in order to determine microbiome compositional aspects at the level of an individual and/or the level of a population of individuals. Compositional aspects can include compositional aspects at the microorganism level, including parameters related to distribution of microorgansims across different taxonomic groups of phyla, classes, orders, families, genera, and/or species (e.g., as measured in total abundance of each group, relative abundance of each group, total number of groups represented, etc.). Compositional aspects can additionally or alternatively include compositional aspects at the genetic level (e.g., in relation to 16S sequences, in relation to 18S sequences, in relation to ITS sequences, in relation to other genetic markers, etc.). Outputs of Block S130 can thus be used to identify features of interest which can be used to characterize the microbiomes of individuals and populations of individuals, wherein the features can be microorganism-based (e.g., presence of a genus of bacteria), genetic-based (e.g., based upon representation of specific genetic regions and/or sequences), and/or based at any other suitable scale.

Characterizing the microbiome composition associated with a sample preferably includes a combination of sample processing techniques (e.g., wet laboratory techniques) and computational techniques (e.g., utilizing tools of bioinformatics) to quantitatively and/or qualitatively characterize the microbiome associated with a sample from an individual.

Figure 5A:
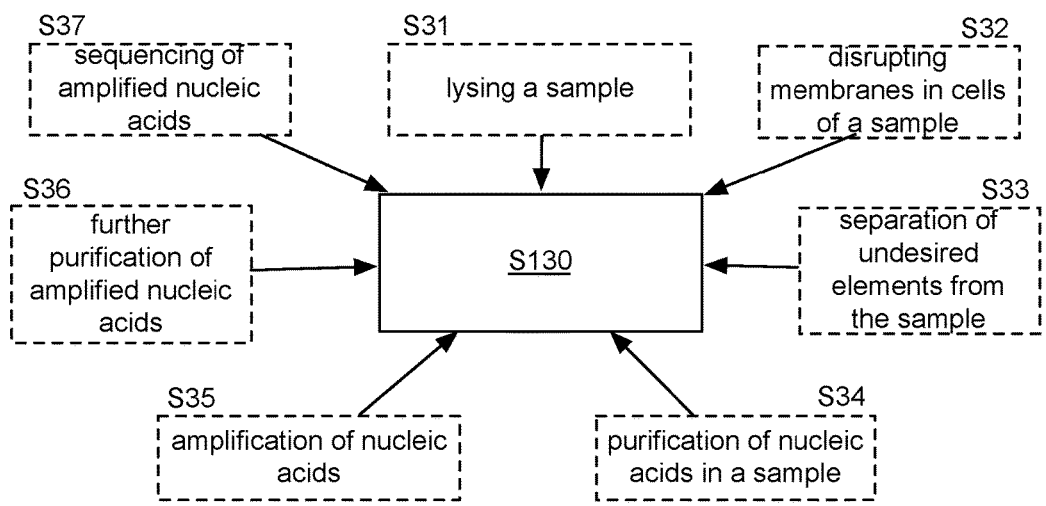
FIG. 5 is a flowchart of a variation of a portion of a method for performing microbiome analysis.

In variations, as shown in FIG. 5, sample processing in Block S130 can thus include any one or more of: lysing a sample S31, disrupting membranes in cells of a sample S32, separation of undesired elements (e.g., RNA, proteins) from the sample S33, purification of nucleic acids (e.g., DNA) in a sample to generate a nucleic acid sample comprising nucleic acid content of a microbiome of the individual and nucleic acid content of the individual S34, amplification of nucleic acids from the nucleic acid sample S35, further purification of amplified nucleic acids of the nucleic acid sample S36, and sequencing of amplified nucleic acids of the nucleic acid sample S37.

In variations, lysing a sample S31 and/or disrupting membranes in cells of a sample S32 preferably includes physical methods (e.g., bead beating, nitrogen decompression, homogenization, sonication) of cell lysing/membrane disruption, which omit certain reagents that produce bias in representation of certain microorganism groups upon sequencing. Additionally or alternatively, lysing or disrupting in Blocks S31 or S32 can involve chemical methods (e.g., using a detergent, using a solvent, using a surfactant, etc.). Blocks S31 and S32 can thus function to complete lysis of components of a sample, in variations wherein the sample has been received at the sample handling network in a pre-processed state of lysis. In variations, separation of undesired elements from the sample S33 can include removal of RNA using RNases and/or removal of proteins using proteases. In variations, purification of nucleic acids in a sample to generate a nucleic acid sample S34 can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of nucleic acids from the nucleic acid sample S35 preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically and phylogenetically. Thus, universal primers (e.g., a F27-R338 primer set, a F515-R806 primer set, etc.) configured to avoid amplification bias can be used in amplification. Primers used in variations of Block S35 can additionally or alternatively include incorporated barcode sequences specific to each biological sample, as described in further detail below, which can facilitate identification of biological samples post-amplification. Primers used in variations of Block S35 can additionally or alternatively include adaptor regions configured to cooperate with sequencing techniques involving complementary adaptors (e.g., Illumina Sequencing). Primers used in variations of Block S35 can additionally or alternatively be configured to target stable nucleic acid regions (e.g., conserved regions, regions not prone to mutation) flanking unstable one or more regions (e.g., mutation-prone regions). Primers used in amplification can, however, be configured in any other suitable alternative manner.

In one example, forward primers for amplification can be designed as shown in Table 1, reverse primers for amplification can be designed as shown in Table 2, and barcode sequences can be designed as shown in Tables 3 and 4, where "F idx" refers to a sequence corresponding to a forward index of an Illumina MiSeq/HiSeq platform; "i5" refers to a forward barcode sequence; transposase refers to a sequence corresponding to a transposase binding site for an Illumina MiSeq/HiSeq platform; "linker" refers to a zero, one, or two base fragment configured to reduce homogeneity and improve sequencing results, "N*" refers to a random base configured to reduce homogeneity and improve sequence results; "16Sv4F" refers to a sequence for targeting a specific target region of nucleic acid material, such as a 16Sv4 region, an ITS region, or an 18S region; "R idx" refers to a sequence corresponding to a reverse index of an Illumina MiSeq/HiSeq platform; and "i7" refers to a reverse barcode sequence. In the example, the forward and reverse barcode sequences comprise a dual indexing system, which can allow for sequencing 480 unique sequencing libraries using a combination of 100 primers.

In some variations, Block S35 can include generation of one or more sequencing libraries, which functions to consolidate amplification products for sequencing, for further analysis, reference, and/or processing. In generating sequencing libraries, amplification products can be normalized based upon an amount of nucleic acid in each amplification product. For example, the amount of each amplification product added to a sequencing library can be inversely proportional to the amount of nucleic acid in each amplification product, such that approximately the same amount of nucleic acid from each amplification product is added to the sequencing library. Sequencing libraries can be further consolidated into larger sequencing libraries, and similar to generation of a sequencing library, the amount of each sequencing library added to a larger sequencing library can be normalized. In an analogous example, the amount of each sequencing library added to the larger sequencing library can be inversely proportional to the amount of nucleic acid in each sequencing library, so that approximately the same amount of nucleic acid from each sequencing library is added to the larger sequencing library. Sequencing libraries can, however, be generated and/or consolidated in any other suitable manner in variations of Block S35.

In variations, sequencing of amplified nucleic acids of the nucleic acid sample S37 can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, single-molecule real-time (SMRT) techniques, sequencing by ligation (e.g., SOLiD) techniques, reversible terminator sequencing techniques, proton detection sequencing techniques, ion semiconductor (e.g., Ion Torrent) sequencing techniques, nanopore sequencing techniques, electronic sequencing techniques, and any other suitable type of sequencing technique. Sequencing in Block S37 can be conducted in a manner whereby multiple samples are sequenced in parallel, are sequenced multiple times (e.g., to ensure an adequate number of reads per sample), and/or are sequenced in any other suitable manner.

In a specific example, amplification and sequencing of nucleic acids from a sample includes: solid-phase PCR involving bridge amplification of DNA fragments of the biological samples on a substrate with oligo adapters, wherein amplification involves primers having a forward index sequence (e.g., corresponding to an Illumina forward index for MiSeq/HiSeq platforms), a forward barcode sequence, a transposase sequence (e.g., corresponding to a transposase binding site for MiSeq/HiSeq platforms), a linker (e.g., a zero, one, or two-base fragment configured to reduce homogeneity and improve sequence results), an additional random base, a sequence for targeting a specific target region (e.g., 16S region, 18S region, ITS region), a reverse index sequence (e.g., corresponding to an Illumina revers index for MiSeq/HiSeq platforms), and a reverse barcode sequence. In the specific example, sequencing comprises Illumina sequencing (e.g., with a HiSeq platform, with a MiSeq platform) using a sequencing-by-synthesis technique.

Aspects of sample processing in Block S130 can be performed in coordination with microbiome standards that include a known quantity and/or distribution of microorganisms (e.g., in terms of cell count, in terms of cell mass, in terms of number of colony forming units). For example, microbiome standards used in Block S130 can include a distribution of from 10-1,000,000 colony forming units (CFUs) of a species, and from 1-10 different species of microorganisms. In a specific example, microbiome standards are prepared with 10,000 CFUs of *Bacillus subtilis*, 100,000 CFUs of *Legionella pneumophilia*, 200 CFUs of *Clostridium perfringens*, 100 CFUs of *Enterococcus faecalis*, and buffer. In the example, the buffer can comprise Tris(hydroxymethyl)aminomethane (e.g., at a concentration of ≤1.8%), sodium chloride (e.g., at a concentration of ≤8%), Edetate disodium dehydrate (e.g., at a concentration of ≤18.6%), and guanidine thiocyanate (e.g., at a concentration of ≤2M), similar to that provided in examples of the sample containers described in relation to Block S110 above; however, the buffer and/or the microbiome standards used in Block S130 can additionally or alternatively comprise any other suitable microorganisms, any other suitable amounts of microorganisms, any other suitable relative distributions of microorganisms, and/or any other suitable buffer.

Furthermore, some aspects of sample processing (e.g., lysis, incubation) in Block S130 can be performed substantially simultaneously with sample provision in Block S110 and/or sample reception in Block S120; however, aspects of sample processing (e.g., amplification, sequencing, etc.) can alternatively be performed in a manner that is distinct from Blocks S110 and/or S120 of the method 100. Furthermore, some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

As noted above, Block S130 is preferably implemented by way of a system 200, as shown in FIGS. 2 and 6, that includes a sample processing module 230 configured to process samples within the sample handling network 210. The sample processing module 230 can comprise a laboratory environment 30 (e.g., wet laboratory environment) within sample handling network 210, wherein samples in sample containers received at the sample handling network 210 are transmitted within the sample handling network 210 to the sample processing module 230 for sample processing (e.g., purification of nucleic acid content, amplification of nucleic acid content, sequencing of nucleic acid content). The sample processing module 230 is preferably implemented entirely within the sample handling network 210, but can additionally or alternatively include sub-modules that are implemented within the sample handling network 210 (e.g., in an "in house" manner) and sub-modules that are implemented outside of the sample handling network 210 (e.g., in an "out of house" manner). In one variation, sample purification can be performed at a first sub-module of the sample processing module 230 within the sample handling network 210, amplification can be performed at a second sub-module of the sample processing module 230 outside of the sample handling network 210, and sequencing can be performed at a third sub-module of the sample processing module 230 outside of the sample handling network 210. The sample processing module 230 and sub-modules thereof can, however, be configured in any other suitable manner in relation to the sample handling network 210.

For sample processing and purification to extract and isolate nucleic acid content of a biological sample, the sample processing module 230 preferably comprises an environment 30 (e.g., sterilized laboratory hood, sterilized room) sterilized of any contaminating substances (e.g., substances that could affect nucleic acids in a sample or contribute to contaminant nucleic acids), wherein sample processing is conducted. The environment 30 can be temperature controlled, controlled for oxygen content, controlled for carbon dioxide content, and/or controlled for light exposure (e.g., exposure to ultraviolet light). The environment 30 can further comprise a lysing module 231 configured to disrupt cellular membranes and facilitate nucleic acid release from microorganism cells in a sample. In one variation, the lysing module 231 can include a bead milling apparatus (e.g., a Tissue Lyser) configured for use with beads that are mixed with a sample and function to agitate biological content of the sample. Alternatively, the lysing module 231 can comprise a combination of one or more of: lysing reagents (e.g., proteinases), heating modules, and any other suitable apparatus(es) for lysing. For isolation of nucleic acids from a lysed sample, the environment can include a purification module 232 for separation of non-nucleic acid content of a sample from nucleic acid content of a sample. A purification module 232 of the sample processing module 230 can operate based upon force-based separation, sized-based separation, binding-moiety-based separation (e.g., with magnetic binding moieties, with buoyant binding moieties, etc.), and/or any other suitable form of separation. For instance, a purification module 232 can include one or more of: a centrifuge to facilitate extraction of a supernatant, a filter (e.g., a filtration plate), a fluid delivery module configured to combine a lysed sample with moieties that bind to nucleic acid content and/or waste material of a sample, a wash reagent delivery system, an elution reagent delivery system, and any other suitable apparatus for purification of nucleic acid content from a sample.

For nucleic acid amplification, the sample processing module 230 preferably comprises amplification substrates 233 (e.g., PCR-compatible sample-receiving substrates) and a thermocycling module 234 configured to perform thermocycling on the amplification substrates 233, wherein the amplification substrates 233 are configured to receive one or more samples (e.g., lysed samples), primer solutions, reagents (e.g., a master mix, PCR water), and any other suitable materials for nucleic acid amplification. The thermocycling module 234 can be configured to thermocycle different amplification substrates according to individualized thermocycling sequences (e.g., temperatures, ramp up times, hold times, ramp down times, cycles, etc.) using an array of individually controllable heating elements, or can additionally or alternatively be configured to thermocycle different amplification substrates according to common thermocycling sequences using a single heating element or an array of co-controlled heating elements. The sample processing module 230 can additionally or alternatively include a second purification module 235 configured to purify nucleic acid amplification products from amplification reagents (e.g., excess primers, excess dNTPs, enzymes, salts, etc.). In variations, the purification module 235 can include purification kits comprising buffers, alcohols (e.g., ethanol, isopropanol, etc.), pH indicators, chaotropic salts, nucleic acid binding fillers, and centrifugation. The sample processing module 230 can, however, comprise any other suitable elements (e.g., spectrophotometric apparatus for quantitation, fluorescence modules for quantitation using fluorescent dyes that bind to nucleic acids, capillary elements for size selection, electrophoretic elements for size selection, filtration elements for size selection, quality control elements, etc).

For sequencing of amplified nucleic acids, the sample processing module 230 can comprise a sequencing module 236 that operates according to one of: sequencing-by-synthesis techniques (e.g., Illumina sequencing), capillary sequencing techniques (e.g., Sanger sequencing), pyrosequencing techniques, single-molecule real-time (SMRT) techniques, sequencing by ligation (e.g., SOLiD) techniques, reversible terminator sequencing techniques, proton detection sequencing techniques, ion semiconductor (e.g., Ion Torrent) sequencing techniques, nanopore sequencing techniques, electronic sequencing techniques, and any other suitable type of sequencing technique. In specific examples, the sequencing module 236 of the sample processing module 230 can include one or more of: an Applied Biosystems® ABI 3730 DNA Analyzer, a 454 Life Sciences® 454 FLX Titanium sequencer, an Illumina® sequencer (e.g., a GAIIx sequencer, a HiSeq sequencer, a MiSeq sequencer), a Pacific Biosciences® PacBio sequencer, an Ion Torrent' sequencer, and any other suitable sequencer.

Elements of the sample processing module 230 can be configured to operate in an automated manner, and in one example, the sample processing module 230 comprises a laboratory automation workstation (e.g., a Biomek® Laboratory Automation Workstation) which automates sample container handling and processing by way of actuators and fluid delivery systems governed by a control module. Alternatively the sample processing module 230 can be configured to be operated at least in part by a trained technician, in order to provide manual or semi-manual forms of sample handling and processing. Furthermore, the sample processing module 230 can be configured to operate in a continuous-flow manner by using fluidic devices (e.g., microfluidic devices) that enable multiple blocks of processing (e.g., sample lysing, nucleic acid extraction, nucleic acid purification, nucleic acid amplification, etc.) to be performed on a single fluidic device. Alternatively, elements of the sample processing module 230 can be configured to operate more discretely using different devices and/or different sample process chambers.

1.3.1 Sample Processing—Multiplex Amplification and Sequencing

In some embodiments of the method 100, sequencing of multiple target regions of nucleic acid materials in a multiplex manner can be performed. In particular, the method 100 can provide blocks configured to perform multiplex amplification and sequencing whereby multiplexed reactions are preformed simultaneously, and in a substantially non-interacting manner (e.g., within a single process chamber) in order to generate sufficient quantities of nucleic acid material for characterization and detection of the multiple target regions. The multiplex amplification and sequencing method described further functions to account for limitations of current multiplex methods and systems, which can be unreliable due to undesired interaction amongst primers (e.g., creation of primer-dimers that can competitively amplify during sample amplification), time consuming, resource consuming (e.g., expensive, requiring multiple separate reactions), and/or problematic due to other limitations.

In one embodiment, as shown in FIGS. 7A and 7B, a method 300 for multiplex amplification and sequencing can comprise: generating a solution upon combination of a sample with a first substrate set having a first primer type, associated with a first nucleic acid marker of a first microorganism portion of the sample and isolated to the first substrate set, and a second substrate set having a second primer type associated with a second nucleic acid marker of a second microorganism portion of the sample and isolated to the second substrate set S310; simultaneously amplifying genetic content associated with the first nucleic acid marker by way of the first substrate set and genetic content associated with the second nucleic acid marker by way of the second substrate set in a single reaction S320; and at a sample processing module within the sample handling network, generating a microbiome sequence dataset based upon sequencing genetic content associated with the first and the second nucleic acid markers S330.

The method 300 is preferably performed in solution, where the primer types and the substrate sets are not coupled to any solid matrix, and are free floating in solution. However, variations of the method 300 can be performed wherein at least one primer type and/or substrate set is not free-floating in solution. The method 300 is preferably implemented at least in part using an embodiment of the system 200, including the sample handling network 210 and the sample processing module 230 described above; however, the method 300 can additionally or alternatively be implemented using any other suitable system.

Block S310 recites: generating a solution upon combination of a sample with a first substrate set having a first primer type, associated with a first nucleic acid marker of a first microorganism portion of the sample and isolated to the first substrate set, and a second substrate set having a second primer type associated with a second nucleic acid marker of a second microorganism portion of the sample and isolated to the second substrate set. Block S310 functions to separate different primer types associated with different nucleic acid marker targets, to different substrates, in order to facilitate performance of simultaneous amplification reactions in a non-interacting manner within a single process chamber. As such, Block S310 can function to prevent formation of primer-dimers (e.g., interacting primers that result from the use of primers that are sufficiently long, but still shorter than nucleic acid fragments intended for amplification), which can competitively amplify with target nucleic acids during sample processing. Block S310 is preferably implemented at a variation of the sample processing module described in relation to Block S130 above; however, Block S310 can alternatively be implemented at any other suitable system configured to combine biological samples with process reagents in a sterile and dependable manner.

In Block S310, the first primer type can include a single primer (e.g., a forward primer, a reverse primer), or can alternatively comprise a pair of primers (i.e., a forward primer and reverse primer pair). Primers of the first primer type used in Block S310 can additionally correspond to target 16S regions, target 18S regions, or target ITS regions of a nucleic acid strand, in order to enable characterization of an associated first nucleic acid marker of a first microorganism portion within the sample. Similarly, primers of the second primer type can include a single primer or a pair of primers, and can be configured to correspond to target 16S regions, target 18S regions, or target ITS regions of a nucleic acid strand, in order to enable characterization of an associated second nucleic acid marker of a second microorganism portion within the sample. The first primer type and the second primer type used in Block S310 preferably correspond to different nucleic acid markers associated with different microorganism portions within the sample, in order to enable characterization of different markers within a single amplification reaction in subsequent blocks of the method 300. Example primers of the first primer type and primers of the second primer type can include primers described in Tables 1 and 2, described in the Appendix of U.S. App. No. 61/953,683, entitled "Multiplex Markers" and filed on 14 Mar. 2014, or any other suitable primers.

In Block S310, the first substrate set type preferably comprises a solid support having desired physical and/or chemical properties that can facilitate performance of multiplex reactions, or facilitate subsequent isolation of amplification products post-amplification. Substrates of the first substrate set type preferably have a dimension sufficiently large enough (e.g., greater than 10 nm) to prevent primer-primer interactions. Additionally, substrates of the first substrate type can have properties that allow for their manipulation (e.g., in solution), including one or more of: morphological properties (e.g., shape, size, etc.), magnetic properties (e.g., paramagnetic properties, diamagnetic properties), density properties (e.g., to affect buoyancy in solution), mass distribution properties (e.g., to affect inertial behavior), conductivity properties (e.g., thermal conductivity properties, electrical conductivity properties), electrical charge-based properties, chemical reactivity-derived properties, and any other suitable type of property. As such, the ability to selectively manipulate substrates of the first substrate type can enhance performance of multiple amplification and sequencing reactions, with reactions occurring in a non-interacting manner. However, substrates of the first substrate set type can alternatively have any other suitable dimensions, shape, physical properties, and/or chemical properties.

In variations, the first substrate set type used in Block S310 can comprise three dimensional substrates (e.g., beads, particles, matrices) and/or two-dimensional substrates (e.g., planar surfaces, non-planar surfaces) coupled to functional moieties that react with portions of different primer types in a selective manner. Substrates of the first substrate type can comprise one or more of: a metallic material (e.g., gold-based material, zirconium-based material, iron-based material, platinum-based material, etc.), a ceramic material (e.g., glass, silica-based material, silicon-based material) and any other suitable material treated for ligation to primers of the first primer type. As such, after an amplification reaction, one amplicon strand remains bound to a substrate, while the complementary amplicon strand is freed into solution.

In one variation, the first substrate set type can include beads bonded to (e.g., covalently bonded to) or comprising functional moieties configured to couple to at least one primer of the first primer type. In this variation, each substrate of the first substrate set can have one coupled primer or primer pair (e.g., forward primer and reverse primer pair), or can include multiple primers or primer pairs of the first primer type. In another variation, the first substrate set type can include a planar or non-planar substrate coupled to forward and reverse primers of the first primer type, in order to enable bridge-PCR for nucleic acid strands in a sample. Alternative variations can, however, comprise any other suitable substrate type configured to couple to any suitable number of primers of the first primer type in any other suitable manner.

The second substrate set type used in Block S310 can be identical to the first substrate set type in composition, morphology, and properties, as described above, aside from aspects of coupling to a different primer type. Alternatively, the second substrate set type used in Block S310 can be substantially different from the first substrate set type in composition, morphology, and/or properties, in order to enable independent manipulation of substrates of the second substrate set type and substrates of the first substrate set type. In one variation, substrates of the first substrate set type can have a first property (e.g., magnetic property, buoyancy-related property, size-related property, etc.) and substrates of the second substrate set type can have a second property, different from the first property, that allows substrates of the first substrate type and substrates of the second substrate type to be manipulated independently of each other. In one such example, substrates of the first substrate set type can be repelled by an applied magnetic field, while substrates of the second substrate set type can be attracted by the applied magnetic field, in order to allow for physical separation of the first substrate set type (and materials coupled thereto) and the second substrate set type (and materials coupled thereto) when desired. The second substrate set type and the first substrate set type can, however, comprise any other suitable combination of similar or dissimilar properties.

The second substrate set type and first substrate set type used in Block S310 can be completely isolated from each other, or can alternatively be indirectly coupled to each other, for instance, by occupying different regions of a larger substrate. Still alternatively, the first substrate set type and the second substrate set type can be positionally configured relative to each other in any other suitable manner.

While two primer types are described in relation to Block S310 above, variations of the method 300 can be expanded to cover variations involving more than two primer types coupled to more than two substrate set types. Furthermore, in alternative variations, one of the different primer types can be uncoupled from a substrate set type (e.g., such that the primer type is free-floating in solution, while other primer types are coupled to different sets of substrates).

Block S320 recites: simultaneously amplifying genetic content associated with the first nucleic acid marker by way of the first substrate set and genetic content associated with the second nucleic acid marker by way of the second substrate set in a single reaction. Block S320 functions to enable simultaneous amplification of multiple nucleic acid regions in non-interacting reactions, and in a manner that avoids undesired primer-primer interactions. Block S320 is preferably performed with the solution comprising the sample, the first substrate set having the first primer type, and the second substrate set having the second primer type contained within a single process chamber, such that multiple non-interacting amplification reactions are performed simultaneously in the single process chamber. In one variation, properties of the substrate sets can be used to further prevent interaction between amplification reactions associated with the first nucleic acid marker and amplification reactions associated with the second nucleic acid marker. In one such example, wherein the first substrate set is repelled by a magnetic field and wherein the second substrate set is attracted by a magnetic field, physical separation between simultaneously occurring reactions associated with a first nucleic acid marker and a second nucleic acid marker can be enhanced by positioning a magnetic field proximal to the process chamber containing the solution. In another such example, wherein the first substrate set has a first magnetic strength and wherein the second substrate set has a second magnetic strength, physical separation between simultaneously occurring reactions associated with a first nucleic acid marker and a second nucleic acid marker can be enhanced by positioning a magnetic field proximal to the process chamber containing the solution. In yet another such example, wherein the first substrate set has a first density and wherein the second substrate set has a second density different from the first density, physical separation between simultaneously occurring reactions associated with a first nucleic acid marker and a second nucleic acid marker can be enabled according to density-based separation between the first substrate set and the second substrate set. However, simultaneous amplification of genetic content associated with the first nucleic acid marker and genetic content associated with the second nucleic acid marker can be performed in any other suitable manner.

In Block S320, amplification is preferably performed in a manner similar to that described in Block S35 above, whereby amplification can include one of: polymerase chain reaction (PCR)-based techniques (e.g., solid-phase PCR, RT-PCR, qPCR, multiplex PCR, touchdown PCR, nano-PCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. Amplification is further preferably performed using an embodiment, variation, or example of the thermocycling module 234 described in relation to Block S130 above. However, amplification can additionally or alternatively be performed using any other suitable technique and/or system.

Block S330 recites: at a sample processing module within the sample handling network, generating a microbiome sequence dataset based upon sequencing genetic content associated with the first and the second nucleic acid markers. Similar to the above variations and examples of amplification, sequencing in a multiplexed, but non-interacting manner can be performed using different properties of the first substrate set and of the second substrate set. Sequencing genetic content associated with the first and the second nucleic acid markers in Block S330 is preferably performed in a manner similar to that described in Block S37 above, whereby sequencing can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, single-molecule real-time (SMRT) techniques, sequencing by ligation (e.g., SOLiD) techniques, reversible terminator sequencing techniques, proton detection sequencing techniques, ion semiconductor (e.g., Ion Torrent) sequencing techniques, nanopore sequencing techniques, electronic sequencing techniques, and any other suitable type of sequencing technique. Furthermore, sequencing is preferably performed using an embodiment, variation, or example of the sequencing module 236 described in relation to Block S130 above. However, sequencing in Block S330 can alternatively be performed using any other suitable sequencing technique/system.

While multiplex markers are described in the context of microbiome characterization and sequencing, variations of the methods for multiplex amplification and sequencing described above can be adapted to whole genome sequencing methods, single nucleotide polymorphism detection, screening and gene expression monitoring, and any other suitable applications benefitting from multiplex amplification and sequencing.

1.3.1 Sample Processing—Next Generation Amplification and Sequencing

In some embodiments of the method 100, a process 700 for next generation amplification and sequencing, as shown in FIG. 8, can include simultaneously amplifying an entire 16S region for each of a set of microorganisms 8710, fragmenting amplicons of the entire 16S region for each of the set of microorganisms to generate a set of amplicon fragments S750, and generating an analysis based upon the set of amplicon fragments S790 wherein the analysis includes at least one of microorganism population characteristics, microorganism species identifications, and identified target microorganism sequences.

The process 700 functions to rapidly generate libraries of microorganism genomes (or gene sequences) that facilitate microbiome analyses at gene function (e.g., product attributed to a specific sequence), individual sequence, individual species, and/or entire microbiome levels. The process 700 can also facilitate multiplex PCR methods, single-pot PCR methods, multiple-pot PCR methods, and/or any other suitable PCR methods. In particular, the process 700 can facilitate processing of 16S sequences (i.e., a relatively long target amplicon) using inexpensive universal primers, while enabling robust analytical results to be obtained. In variations, the process 700 can be adapted to processing and analyzing nucleic acid regions of interest in addition to the 16S region. For instance, variations of the process 700 can be adapted to analysis of heat shock proteins, antibiotic resistance genes (e.g., aminoglycoside resistance genes, beta lactamase resistance genes, macrolide-lincosamide-streptogramin B resistance genes, multi-drug transporter resistance genes, tetracycline resistance genes, vancomycin resistance genes, etc.), the 18S region of organisms, the ITS region of organisms, proteins that code for specific enzymes, human genes (e.g., as in genomic analyses), and any other suitable region of interest.

Block S710 recites: amplifying an entire 16S region for each of a set of microorganisms, which functions to amplify whole regions of interest (i.e., the 16S region) of a bacterial genome. Instead of amplifying and analyzing each subregion (e.g., the V1-V9 hypervariable subregions, the V4 subregion) of the 16S region independently, Block S710 allows for amplification of the entire 16S region of a bacterial genome, for a set of microorganisms. Downstream analysis of the hypervariable subregions (i.e., the V1-V9 subregions, the V4 subregion) can still, however, be performed in implementation of the process 700, which allows for identification and/or differentiation of different taxonomic groups of microorganisms or specific sequences, thus providing insights into one's microbiome composition. In Block S710, amplification is preferably performed with universal primers appropriate for a wide variety of microorganisms. In examples, amplification is performed with universal primers comprising one or more of: an 8F primer, a 27F primer, a CC[F] primer, a 357F primer, a 515F primer, a 533F primer, a 16S.1100.F16 primer, a 1237F primer, a 519R primer, a CD[R] primer, a 907R primer, a 1391R primer, a 1492R(I) primer, a 1492R(s) primer, a U1492R primer, a 928F primer, a 336R primer, an 1100F primer, an 1100R primer, a 337F primer, a 785F primer, an 805R primer, a 518R primer, and any other suitable universal primer. Alternatively, for samples in which specific primers would be appropriate, amplification can be performed with specific primers. In examples, specific primers can include: a CYA106 primer (for cyanobacteria), a CYA359F primer (for cyanobacteria), an 895F primer (for bacteria excluding plastids and cyanobacteria), a CYA781R primer (for cyanobacteria), a 902R primer (for bacteria excluding plastids and cyanobacteria), a 904R primer (for bacteria excluding plastids and cyanobacteria), an 1100R primer (for bacteria), an 1185mR primer (for bacteria excluding plastids and cyanobacteria), an 1185aR primer (for lichen-associated Rhizobiales), a 1381R primer (for bacteria excluding Asterochloris species plastids), or any other suitable specific primer.

In Block S710, amplification is preferably performed for a number of cycles to achieve a desired number amplicons (e.g., total number of amplicons, total concentration of amplicons, total number of 16S amplicons per microorganism, etc.). In a specific example, amplification in Block S710 can be performed for 30 cycles to achieve a desired number of amplicons per microorganism represented in a sample. However, any other suitable number of cycles of amplification can be performed in Block S710. In Block S710, amplification preferably includes effective denaturation of a nucleic acid template, adequate extension times to generate amplicons, and protection of target amplicons from damage (e.g., by depurination). In examples, effective denaturation can be achieved using one or more of: higher temperatures for shorter durations and cosolvents (e.g., 1-10% DMSO, Betaine). In examples, extension can be achieved at a temperature below 68° C. and for a duration greater than 15 minutes. However, any other suitable amplification conditions can be used in Block S710.

Block S750 recites: fragmenting amplicons of the entire 16S region for each of the set of microorganisms to generate a set of amplicon fragments, which functions to generate shorter read sequences that can be sequenced and/or analyzed according to other blocks of the method. In Block S750, fragmenting can be performed using one or more of: enzymatic fragmentation methods (e.g., Nextera enzyme-mediated fragmentation), bead beating, sonication (e.g., with a Covaris sonication device, with a Biruptor sonication device, etc.), and any other suitable amplicon fragmentation mechanism. In variations, fragmentation length can be controlled based upon the intensity of the fragmentation mechanism (e.g. concentration of enzyme, intensity of bead beating, intensity of sonication), the duration over which the fragmentation mechanism is applied, using a combination of fragmentation mechanisms, and/or in any other suitable manner (e.g., size of beads used in bead beating). Furthermore, in implementation of Block S750, size-selection of fragments with a desired length (e.g., for sequence reads) can be performed. In variations, size selection can be performed using one or more of: magnetic separation (e.g., paramagnetic beads with a binding moiety, diamagnetic beads with a binding moiety, AMPure beads, MagJET beads, etc.), buoyancy-based separation (e.g., low density beads with a binding moiety), microfluidic channel-based separation (e.g., using inertial focusing, using stagnation flows, using confining channels, etc.), and any other suitable size-selection approach.

Block S790 recites: generating an analysis based upon the set of amplicon fragments wherein the analysis includes at least one of microorganism population characteristics, microorganism species identifications, and identified target microorganism sequences. Block S790 functions to further process the set of amplicon fragments generated as outputs from Block S750, and to analyze the amplicons to derive sequence-specific insights, species-specific insights, other taxonomic group-specific insights, and/or microbiome population-specific insights. Block S790 can include one or more of: sequencing the set of amplicon fragments S791, assembling a full gene based upon sequenced amplicon fragments S792, performing Bayesian statistics for characterization based upon species, strain and/or gene identification S793, detection of specific sequences from the set of amplicon fragments S794, analyzing product-sequence associations based upon reading the set of amplicon fragments S795, and performing any other suitable downstream analysis of the set of amplicon fragments.

In variations and examples of Block S791, sequencing the set of amplicon fragments can include any one or more of: ligating at least a subset of the set of amplicon fragments (e.g., using a Nextera ligation process reagent); performing an enzyme-mediated reaction (e.g., enzyme-mediated insertion, enzyme-mediated integration, enzyme-mediated synthesis, etc.) with amplicons of the set of amplicon fragments; combining the set of amplicon fragments with custom primers associated with a sequencing technique (e.g., custom Illumina® primers for a sequencing-by-synthesis approach); performing random primer PCR (e.g., random amplified polymorphic DNA PCR); and performing any other suitable sequencing operation, variations and examples of which are described in other portions of this specification.

In variations and examples of Block S792 and S794, assembling a full gene based upon sequenced amplicon fragments and/or detection of specific sequences from the set of amplicon fragments functions to specific gene and/or nucleic acid sequence-level analyses associated with an individual's microbiome to be analyzed. Blocks S792 and/or S794 can be performed as described in relation to Block S140 below, wherein sequence alignment, mapping, and encoding enable full gene assembly and/or detection of specific sequences from the set of amplicon fragments. Additionally or alternatively, full gene assembly and/or detection of specific sequences from the set of amplicon fragments can be performed in any other suitable manner.

In variations and examples of Block S793, performing Bayesian statistics for characterization based upon species, strain and/or gene identification functions to implement bioinformatics techniques to reveal intrinsic features (e.g., phylogenetic relationships, metabolic potential, diversity-related features, etc.) derived from amplicon fragments of the 16S region. In Block S793, Bayesian statistics algorithms utilized begin with a prior probability distribution that represents what is known about the diversity of the microbiome associated with a sample. Block S793 can implement any suitable number of assumptions (e.g., assumptions related to interdependencies between species, assumptions related to aggregation of species, etc.) related to diversity of the microbiome. The Bayesian approach then determines a posterior distribution using observed sequence information to generate probabilities of different estimations of microbiome population characteristics. Outputs of Block S793 can be fine-tuned based upon incorporation of weighting factors (e.g., lower weights attributed to unreliability of low frequency reads), use of Bayesian inference to update the probability of a diversity hypothesis (i.e., as new information is acquired), and/or in any other suitable manner. Furthermore, outputs of Block S793 for individual microbiome communities can be used to generate comparisons of diversity between multiple microbiome communities, as described in further detail below. Additionally or alternatively, Block S793 can implement any other suitable bioinformatics-based approach to describe species, strain, and/or gene diversity of the microbiome associated with a sample While Blocks S710, S750, and S790 are described in one order above, amplification, fragmentation, sequencing, and downstream processing can alternatively be performed in any other suitable order, in order to facilitate generation of microbiome-based analyses from biological samples.

Furthermore, while the process 700 is described in the context of microbiome characterization and sequencing, variations of the process 700 described above can be adapted to whole genome sequencing methods, single nucleotide polymorphism detection, screening and gene expression monitoring, and any other suitable applications benefitting from multiplex amplification and sequencing.

1.4 Microbiome Characterization—Sequence Alignment, Mapping, and Encoding

Block S140 recites: at a processing system within the sample handling network, identifying a set of microorganisms represented in the microorganism portion based upon performance of a mapping operation on portions of the microbiome sequence dataset. Block S140 functions to implement computational processing techniques, in transforming an input of unanalyzed microbiome sequence data into an output that characterizes represented microorganisms within the sample. Outputs of Block S140 can thus be used to derive values of parameters related to relative distributions of microorganism groups within the microbiome of an individual, abundances of microorganism groups within the microbiome of an individual, represented genetic markers within the microbiome of an individual, and/or any other suitable parameters, as further described in Block S150 below. In variations, as shown in FIG. 9A, computational processing in Block S140 can include any one or more of: identifying sequences associated with the microorganism portion S141 (e.g., as opposed to human sequences and contaminants), and performing alignment and mapping of sequences associated with the microorganism portion S142 (e.g., alignment of fragmented sequences using one or more of single-ended alignment, ungapped alignment, gapped alignment, pairing).

Identifying sequences associated with the microorganism portion, as in Block S141, can include mapping of sequence data from sample processing to a human reference genome (e.g., provided by the Genome Reference Consortium), in order to remove human genome-derived sequences. Additionally, identifying sequences associated with the microorganism portion can include discarding sequences associated with unintelligible and/or low quality reads at a module of the processing system configured to perform quality filtering of reads (e.g., according to the use of Q or Phred quality scores), such that only non-human and high quality reads (e.g., reads above a certain quality score threshold in terms of a Q or Phred score) remain after Block S141 is performed. However, identifying sequences associated with the microorganism portion can be performed in any other suitable manner.

In Block S142, unidentified sequences remaining after mapping of sequence data to the human reference genome can then be further clustered into operational taxonomic units (OTUs) based upon sequence similarity and/or reference-based approaches (e.g., using VAMPS, using MG-RAST, using QIIME databases), assembled based upon overlapping with other reads, and aligned to reference sequences. In Block S142, alignment can be performed in multiple phases, using one or more of: single-ended alignment, ungapped alignment, gapped alignment, paired alignment (e.g., with forward and reverse pairs of sequences), clustered alignment (e.g., with clustering of forward reads and clustering of reverse reads), and any other suitable phase of alignment. Furthermore, alignment algorithms implemented at a module of the processing system can be configured for specific read lengths or ranges of read lengths, in order to increase the efficiency of alignment processing based upon sequence lengths. Alignment algorithms in Block S142 can implement a hashing approach with large contiguous seeds and/or with adaptive stopping techniques, whereby a read is considered to be aligned based upon a determination of the best read alignment across a set of read alignment candidates, and the number of read alignment candidates considered. Alignment algorithms in Block S142 can additionally or alternatively include string comparison algorithms that compare a number of mismatches between two strings (e.g., a reference read and a sequence read) of the same length. Alignment algorithms in Block S142 can additionally or alternatively use profile stochastic context-free grammars (e.g., implementing covariance models), using, for instance, an SSU-align algorithm. Any other suitable type of alignment algorithm can be used, and variations of alignment algorithms are noted below.

In variations, alignment and mapping to reference bacterial genomes (e.g., provided by the National Center for Biotechnology Information) in Block S142 can be performed using an alignment algorithm including one or more of: a Needleman-Wunsch algorithm that performs a global alignment of two reads (e.g., a sequencing read and a reference read) with a stopping condition based upon scoring of the global alignment (e.g., in terms of insertions, deletions, matches, mismatches); a Smith-waterman algorithm that performs a local alignment of two reads (e.g., a sequencing read and a reference read) with scoring of the local alignment (e.g., in terms of insertions, deletions, matches, mismatches); a Basic Local Alignment Search Tool (BLAST) that identifies regions of local similarity between sequences (e.g., a sequencing read and a reference read); a FPGA accelerated alignment tool; a BWT-indexing with BWA tool; a BWT-indexing with SOAP tool; a BWT-indexing with Bowtie tool; Sequence Search and Alignment by Hashing Algorithm (SSAHA2) that maps nucleic acid sequencing reads onto a genomic reference sequence using word hashing and dynamic programming; and any other suitable alignment algorithm. Mapping of unidentified sequences in Block S142 can further include mapping to reference viral genomes and/or fungal genomes, in order to further identify viral and/or fungal components of the microbiome of an individual. For instance, PCR can be performed with multiple markers (e.g., a first marker, a second marker, a third marker, an Nth marker) in parallel or in series, and associated with one or more of bacterial markers, fungal markers, and eukaryotic markers. Furthermore, overlapping reads (e.g., generated by paired end sequencing) can be assembled based upon outputs of the alignment algorithm, or aligned sequence reads can be merged with reference sequences (e.g., using a hidden Markov model banding technique, using a Durbin-Holmes technique). Alignment and mapping in Block S142 can, however, implement any other suitable algorithm or technique.

In relation to Blocks S140, S141, and S142, sequence reads can be encoded to facilitate alignment and mapping operations performed. In one example, each base of a sequence can be encoded as a byte according to the arrangement 0000TGCA, whereby the least significant bit is 1 if the base is sequenced as possibly containing the base A (e.g., A is represented as 00000001), the next significant bit is 1 if the base is sequenced as possibly containing the base C (e.g., C is represented as 00000010), the next significant bit is 1 if the base is sequenced as possibly containing the base G (e.g., G is represented as 00000100), and the next significant bit is 1 if the base is sequenced as possibly containing the base T (e.g., T is represented as 00001000). In the example, the four most significant bits are set to zero. However, alternative variations of the example can encode bases in any other suitable manner. Furthermore, known sequences of primers used during amplification in Block S130 can be used to trim sequence reads to omit primer sequences to increase the efficiency of alignment and mapping.

In one variation with encoded sequences, a simhash (i.e., fuzzy hash) algorithm can be used to form aligned clusters that can be compared to reference sequences in an efficient manner. In this variation, the simhash algorithm can be configured to ignore the four most significant bits set to zero (e.g., in relation to the example of encoding described above), and to produce a hash, wherein similar inputs are converted to similar hash outputs in a manner that facilitates cluster analyses of hashed outputs. The simhash algorithm can be configured with a comparison sequence length (e.g., having a given "wordlength") in order to determine how sensitive the hash is to ordering, which can be used to determine the granularity of the algorithm and the number of resulting clusters.

Hashing can include reducing a length of a read to a shorter length (e.g., from 300 bases to 10-25 bases) in a fuzzy hash process, and using the fuzzy hash process to cluster sequences with identical fuzzy hashes. The distribution of clustered sequences can comprise a large group of clusters with a small number of reads (e.g., 1-5 reads), which can be processed separately from a group of clusters with a large number of reads. After the sequences are clustered together, they can be indexed with a strict hash (e.g., a word length of 25-300 bases), and the clusters can be compared to a set of reference sequences, wherein the set of reference sequences can be trimmed (e.g., based upon known primer sequences used to amplify the sample) and hashed at the same hash length as that of the clusters to produce hashed references that are associated with the set of reference sequences. Then, further hashing of both the set of reference sequences and the distribution of clustered sequences, with comparison between the set of reference sequences and the distribution of clustered sequences at each iteration, can be performed until a threshold condition of matching between reference sequences and clustered sequences is satisfied.

In a first variation, the hashing process can be performed for amplicons of similar type (e.g., amplicons of specific 16S hypervariable subregions, amplicons of 18S subregions, amplicons of ITS subregions, etc.), whereby clusters of amplicon reads having a desired length can be indexed and compared to one or more reference sequences (e.g., reference sequences trimmed to the desired length). In the comparison operation, the amplicon reads and the reference reads can each be encoded as a byte (e.g., as a byte according to the arrangement 0000TGCA, as described above), whereby each base of a read is aligned and the sum of the aligned encoded bases is used for comparison according to a threshold condition. In one example, as shown in FIG. 16, ones in an encoded base can be transformed into twos and zeroes in an encoded base can be transformed into ones prior to summation, and the summed amplicon read can then be transformed back into binary, whereby positive digits are transformed back to ones, and negative digits are transformed back to zeroes. Summation and comparison can, however, be performed in any other suitable manner. In the first variation, amplicon reads can then be grouped by similarity according to the threshold condition, in order to facilitate generation of microbiome population insights (e.g., taxonomic group representation, diversity, etc.).

In a second variation, the hashing process can be performed for a set of random amplicon fragments (e.g., generated according to the process 700 described above), whereby a desired word length (e.g., 1-5 bases) can be used for comparison between amplicon fragment reads and reference reads. In the second variation, fragments can be clustered according to fragment length or any other suitable characteristic. In the second variation, a sequence (e.g., GCCA) can be chosen and detected (or not detected) across all amplicon fragment reads, wherein the chosen sequence can be used to compare the amplicon fragment reads to the reference read. As such, the second variation can provide an order-independent comparison operation that is sensitive to deletions in bases of a sequence. Similar to the first variation, in the comparison operation, the random amplicon fragment reads and the reference reads can each be encoded as a byte (e.g., as a byte according to the arrangement 0000TGCA, as described above), whereby each base of a read is aligned and the sum of the aligned encoded bases is used for comparison according to a threshold condition. Summation and comparison can, however, be performed in any other suitable manner. In the second variation, reads can then be grouped by similarity according to the threshold condition, in order to facilitate generation of microbiome population insights (e.g., taxonomic group representation, diversity, etc.).

Mapping of encoded sequences to reference sequences can, however, be performed in any other suitable manner.

As noted above, Block S140 is preferably implemented by way of a system 200, as shown in FIGS. 2 and 9B, that includes a processing system 240 configured to perform microbiome-based analyses on sequenced nucleic acid content of biological samples processed within the sample handling network 210. The processing system 240 can be in direct communication with modules of the sample processing module 230, and in one variation, a sequencing module 236 of the sample handling network 210 can be configured to provide sequenced data as an output to a module of the processing system 240. Additionally or alternatively, the processing system 240 can be configured to receive inputs from outputs of the sample processing module 230 by way of a storage device 241 configured to store derived from processing of samples received at the sample handling network 210. The processing system 240 is preferably implemented in one or more computing systems, wherein the computing system(s) can be implemented at least in part in the cloud and/or as a machine (e.g., computing machine, server, etc.) configured to receive a computer-readable medium storing computer-readable instructions. As such, the processing system 240 can comprise one or more processing modules, implemented in the cloud and/or as machine, comprising instructions for performing blocks of the method 100. In one variation, the processing system 240 can include a first module 242 configured to receive data derived from outputs of the sequencing module 236, a second module 243 configured align and map sequenced data from the first module 242 as described in relation to Blocks S140-S142 above, and a third module 244 configured to receive outputs of the second module 243 in order to generate features and derive insights, as described in relation to Block S150 below. The processing system 240 can, however, be configured in any other suitable manner.

1.4.1 Processing and Characterization Controls—Sample Identification

In processing a sample to generate a microbiome sequence dataset from a sample, Blocks S130 and/or S140 can include an identification step that combines one or more nucleic acid identification sequences as "barcodes" with each sample or for each individual associated with a set of samples received at the sample handling network in Block S120. Use of identification sequences can thus function to enable identification of samples in association with a specific individual, enable detection of contamination (e.g., cross-contamination) of samples, and facilitate quantification of reads associated with given sequences in a sample that is processed in a multiplex manner. A nucleic acid identification sequence can comprise a synthetic strand of one or more of 16S DNA, 16S RNA, 18S DNA, 18S RNA, ITS DNA, ITS RNA, and any other suitable region of DNA or RNA, wherein synthetic nucleic acid molecules can be non-naturally occurring and/or comprise non-natural bases. Alternatively, a nucleic acid identification sequence can comprise a non-synthetic strand of nucleic acid material.

Furthermore, an identification sequence can be used for identification based upon its specific sequence and/or its expression level in solution. With multiple nucleic acid identification sequences and multiple expression levels for each sequence, $m^N$ samples can be uniquely encoded, where N represents the number of unique nucleic acid identification sequences and m represents the number of unique expression levels for each unique nucleic acid identification sequence. In a specific example, 10 distinct nucleic acid identification sequences, each having three possible expression levels (e.g., no expression, moderate expression, high expression) provides encoding for up to $3^{10}$ samples. However, any other suitable number of identification sequences, and any other suitable number of expression levels can be used to expand the total number of possible encoded samples. In implementing nucleic acid barcodes, Blocks S130 and/or S140 can thus include generating a mixture upon combination of an identifying reagent, including a subset of a set of nucleic acid identification sequences, each having one of a set of expression levels, with a sample received from an individual, whereby later detection of the nucleic acid identification sequences and expression levels can be used to uniquely identify the sample at various stages of sample processing. The identifying reagent can be included in a sample container provided in a sampling kit, as described in relation to Block S110 above, or can additionally or alternatively be combined with a sample after a sample has been received at the sample handling network.

One variation of a method 400 for sample processing using identification sequences, as shown in FIG. 10, can include: generating a mixture upon combining a nucleic acid sample, generated from a sample, with a first synthetic nucleic acid molecule having a first sequence and a first concentration and a second synthetic nucleic acid molecule having a second sequence and a second concentration S41; generating a sequence dataset based upon sequencing nucleic acid content of the microbiome and of the first and the second synthetic nucleic acid molecule of the mixture S42; and associating the sequence dataset with the individual based upon identification of the first and the second sequence and the first and the second concentration from the sequence dataset S43. Blocks S41-S43 can, however, be expanded to cover variations with fewer than or more than two synthetic acid molecules, each with a range of expression levels, functioning as "barcode" or identification sequences.

Block S41 recites: generating a mixture upon combining the nucleic acid sample with a first synthetic nucleic acid molecule having a first sequence and a first concentration and a second synthetic nucleic acid molecule having a second sequence and a second concentration. Block S41 functions to tag each sample received in Block S120 with an identifying reagent having a specific and known composition of one or more identification sequences, which can be detected and used for sample identification during other blocks of the method 100. Generating the mixture in Block S43 can be performed during sample provision and facilitated by way of sample containers of the sampling kit provided in Block S110. In one variation, each sample container configured to receive a sample in Block S110 can be packaged with the identifying reagent having the first and the second synthetic nucleic acid molecules, such that the identifying reagent is combined with the sample as the individual (or another entity) mixes (e.g., stirs, shakes) the sample container during sample pre-processing. In this variation, sampling kits can be linked with specific identifying reagents, in order to enable association of samples received by way of the sampling kits, with the synthetic nucleic acid sequences of the identifying reagent. Alternatively, identifying reagent(s) having the first and the second synthetic nucleic acid molecules can be combined with the sample after reception at the sample handling network, in order to generate the mixture.

The barcode sequences can comprise greater than 5 bases, but can alternatively comprise any other suitable number of bases. Furthermore, the barcode sequences and concentrations are preferably different from that contributed by potential undesirable sample contaminants, such that confusion between contaminants and barcode sequences is avoided. Even further, the barcode sequences can comprise sequences substantially different from target nucleic acid sequences of the sample used for microbiome characterization, which can facilitate making distinctions between target nucleic acid sequences and barcode sequences during sample processing. Alternatively, the barcode sequences can comprise sequences similar to target nucleic acid sequences of the sample used for microbiome characterization, with any suitable degree of similarity. The first concentration of the first synthetic nucleic acid molecule and the second concentration of the second synthetic nucleic acid molecule are preferably selected amongst a discrete number of concentrations (e.g., up to 10 concentrations ranging between a low concentration and a high concentration); however, first concentration of the first synthetic nucleic acid molecule and the second concentration of the second synthetic nucleic acid molecule can alternatively be selected amongst a continuous spectrum of concentrations. Furthermore, identifying characteristics of the first synthetic nucleic acid molecule and the second synthetic nucleic acid molecule can comprise characteristics differing in more than sequence and concentration (e.g., difference in length, difference in morphology, difference in folding behavior, etc.).

As noted above, the barcode sequences can be associated with primers implemented during an amplification process, or otherwise combined with a sample in any other suitable manner. Example barcode sequences are noted in Tables 3 and 4; however, variations and examples of Block S41 can include any other suitable barcode sequences.

Block S42 recites: generating a sequence dataset based upon sequencing nucleic acid content of the microorganism ecosystem and of the first and the second synthetic nucleic acid molecule of the mixture, which functions to sequence nucleic acid content of the sample for microbiome characterization, in cooperation with sequencing of the first and the second synthetic nucleic acid molecules for sample identification. Block S42 is preferably implemented at an embodiment, variation, or example of the sample processing module described in relation to Block S130 above; however, Block S42 can additionally or alternatively be implemented at any other suitable system configured to amplify and/or sequence nucleic acid content of a biological sample. In Block S42, amplification and sequencing are preferably performed according to the embodiments, variations, and/or examples of Blocks S130, S35, and S37 described above; however, amplification and sequencing in Block S42 can alternatively be performed in any other suitable manner.

Block S43 recites: associating the sequence dataset with the individual based upon identification of the first and the second sequence and the first and the second concentration from the sequence dataset, which functions to verify the identity of a sample and/or sequence dataset based upon detection and characterization parameters derived from the first synthetic nucleic acid molecule and the second synthetic nucleic acid molecule upon processing as in Block S42. Block S43 is preferably performed at an embodiment, variation, or example of the processing system described in relation to Blocks S140-S142 above; however Block S43 can additionally or alternatively be implemented using any other suitable computing system configured to determine parameters derived from sequencing data for purposes of sample identification.

In Block S43, the processing system can be configured to locate all reads corresponding to the first and the second sequence, as associated with the first synthetic nucleic acid molecule and the second synthetic nucleic acid molecule. The processing system can then be configured to determine a first value indicative of a first abundance of the first synthetic nucleic acid molecule and a second value indicative of a second abundance of the second synthetic nucleic acid molecule. The first value and the second value can then be used to estimate or determine a value of a parameter indicative of the first concentration and the second concentration of the first and the second synthetic nucleic acid molecules, in order to verify identification of the sample's identity based upon barcode sequences. The parameter can be a ratio between the relative abundances of reads having the first sequence and reads having the second sequence, which can be indicative of a ratio between the first concentration and the second concentration. Alternatively, the parameter can be related to the first and/or the second concentration, as adjusted by an efficiency of primers used in the amplification process. In variations, the first value and the second value can be determined according to quantitation of the first and the second synthetic nucleic acid molecules, for instance, using a spectrophotometric or fluorescence-based approach; however, the first value and the second value can alternatively be determined in any other suitable manner.

In Block S43, the processing system can further comprise a module configured to compare reads against all synthetic nucleic acid modules used as barcode sequences in the method 100 and/or system 200, which functions to enable identification of cross-contamination between samples. For instance, the module can be configured to detect presence of one or more unanticipated synthetic nucleic acid sequences present in the sample or processed versions thereof, which can indicate that samples were mixed together and should not be trusted for accurate characterization. Upon identification of an unanticipated presence of a set of undesired synthetic nucleic acid molecules in a sample, Block S43 can further include identifying a second sample associated with the set of undesired synthetic nucleic acid molecules, and performing an error correction action. In variations, the error correction action can comprise one or more of: analyzing the second sample to determine if contamination only occurred in one direction (e.g., the second sample contaminated the sample, but the sample did not contaminate the second sample) or in both directions, notifying an entity of the sample handling network of potential contamination, notifying an entity of the sample handling network that further processing of a contaminated sample should not continue, notifying the individual providing the sample that another sample may need to be re-provided, and any other suitable error correction action. Block S43 can, however, comprise any other suitable steps or blocks configured to enhance sample identification and/or identification of sample contamination.

While identification in Blocks S41-S43 is described in relation to analysis of a microbiome portion of a sample from an individual, Blocks S41-S43 can be adapted to methods for performing analyses on any other suitable biological sample, using any other suitable biological component as a barcode/identifying feature (e.g., distribution of synthetic organelles for identification purposes, distribution of cell populations for identification purposes, etc.).

1.4.2 Processing and Characterization Controls—Plasmid Controls

In processing a sample to generate a microbiome sequence dataset from a sample, Blocks S130 and/or S140 can additionally include blocks configured to facilitate simultaneous quantification of nucleic acid material within a sample and identification of a sample in association with an individual. Blocks associated with simultaneous quantification and identification can include processing a sample with a combination of a solution having a target nucleic acid sequence and a solution having a reference sequence coupled to the target sequence, which can be used to back-calculate a quantity of nucleic acid molecules having the target sequence, while enabling verification of the identity of the sample by way of the reference sequence.

In one such variation, as shown in FIGS. 11A and 11B, a method 500 for associating a sequence dataset with an individual and determining a quantity of nucleic acid molecules represented in the sequence dataset and having a target sequence, can include: preparing a first solution including a first sample of nucleic acid material having a target sequence S51; preparing a second solution containing a second sample of nucleic acid material having the target sequence and an identification sequence S52; preparing a third solution upon combination of a first portion of the first solution and a second portion of the second solution, wherein the second portion includes a reference quantity of nucleic acid material S53; preparing a fourth solution upon amplifying nucleic acid material of the third solution S54; generating the sequence dataset based upon sequencing nucleic acid material of the fourth solution S55; from the sequence dataset, determining a reference number of reads associated with the identification sequence and a total number of reads associated with the target sequence S56; determining the quantity of nucleic acid molecules having the target sequence based upon the total number of reads, the reference number of reads, and the reference quantity of nucleic acid material S57; and associating the sequence dataset with the individual based upon at least one of detection of the identification sequence and the reference number of reads S58.

The method 500 can be used to identify and quantify samples using combinations of synthetic nucleic acid molecules, measure background contamination to allow for quality control, enable contamination level nucleic acid molecules to be distinguished from target nucleic acid molecules in a sample, enable quantification of gene expression, enable simultaneous investigation of gene expression of multiple regions within a single sample, enable relative abundances of various genetic markers to be determined, and to enable absolute abundances of certain genetic markers to be determined. The method 500 is preferably implemented using an embodiment, variation, or example of the system 200, comprising a sample handling module 230 and a processing system 240, described above; however, the method 500 can additionally or alternatively be implemented using any other suitable system(s).

Block S51 recites: preparing a first solution including a first sample of nucleic acid material having a target sequence, which functions to provide a sample solution that can be combined with other functional solutions, amplified, sequenced, and analyzed in order to back-calculate a number of strands of nucleic acid molecules having the target sequence in the first sample. Preferably, the first sample comprises a nucleic acid material derived from a biological sample from an individual. As such, the first sample can comprise a sample taken from a collection site of an individual, as described in relation to Block S110 above. The first solution comprising the first sample can, however, comprise any other suitable sample having a target sequence of interest. The target sequence is preferably a known sequence, in order to facilitate calculation of a number of strands of nucleic acids having the target sequence post amplification of a solution containing the sample solution.

In one example, the target sequence can correspond to a DNA primer, such that the primer includes a first primer solution with a degenerate DNA sequence including the following bases: CCAGCASCYGCGGTAATTCC, and a second primer solution with a degenerate DNA sequence including the following bases: ACTTTCGTTCTTGATYRA. In another example, the target sequence can correspond to a DNA primer, such that the primer includes a first primer solution with a DNA sequence including the following bases: TGGTCATTTAGAGGAAGTAA, and a second primer solution with a DNA sequence including the following bases: TGCGTTCTTCATCGATGC. In yet another example, the target sequence can correspond to a DNA primer, such that the primer includes a first primer solution with a degenerate DNA sequence including the following bases: GTGCCAGCMGCCGCGGTAA, and a second primer solution with a degenerate DNA sequence including the following bases: GGACTACHVGGGTWTCTAAT. In yet another example, the target sequence can correspond to a DNA primer, such that the primer includes a first primer solution with a DNA sequence including the following bases: AGAGTTTGATCCTGGCTCAG, and a second primer solution with a DNA sequence including the following bases: ATTACCGCGGCTGCTGG. The target sequence of the first sample can, however, comprise any other suitable sequence corresponding to any other suitable primer(s).

Block S52 recites: preparing a second solution containing a second sample of nucleic acid material having the target sequence and a reference sequence, which functions to provide a second solution that includes nucleic acid molecules having features that can 1) facilitate identification of a solution, having nucleic acid molecules with the target sequence, combined with the second solution upon amplification and sequencing, and 2) quantification of nucleic acid molecules of the solution having the target sequence. Preferably, the second sample comprises a sample of nucleic acid material having a reference sequence that functions as an identification sequence (e.g., a barcode, as in Blocks S41-S43 above). Furthermore, the sample of nucleic acid material can have a first primer part and a second primer part, associated with the target sequence of the first solution, wherein the first primer part and the second primer part flank the identification sequence. The reference sequence/identification sequence preferably includes synthetic nucleic acid material statistically unlikely to appear in the first solution with the first sample, such that the reference sequence is readily distinguishable from sequences potentially represented in the first solution. However, the reference sequence/identification sequence can alternatively be similar to a nucleic acid sequence potentially present in the first solution, with any suitable degree of similarity.

In one example, the second sample of nucleic acid material having the target sequence and a reference sequence can include a first primer part with a DNA sequence including the following bases: CCAGCAGCTGCGGTAATTC, followed by a reference sequence including the following bases: TACGACGGTACACGT, followed by the reverse compliment of a second primer part including the following bases: TCGATCAAGAACGAAAGT. In another example, the second sample of nucleic acid material having the target sequence and a reference sequence can include a first primer part with a DNA sequence including the following bases: TGGTCATTTAGAGGAAGTAA, followed by a reference sequence including the following bases: TCCGAAAGGGCTTTGA, followed by the reverse compliment of a second primer part including the following base pairs: GCATCGATGAAGAACGCA. In still another example, the second sample of nucleic acid material having the target sequence and a reference sequence can include a first primer part with a DNA sequence including the following bases: GTGCCAGCAGCCGCGGTAA, followed by a reference sequence including the following bases: CTTATTACCTGCGAGT, followed by the reverse compliment of a second primer part including the following base pairs: ATTAGATACCCGTGTAGTCC. In still another example, the second sample of nucleic acid material having the target sequence and a reference sequence can include a first primer part with a DNA sequence including the following bases: AGAGTTTGATCCTGGCTCAG, followed by a reference sequence including the following bases: ACCCGTACTTCTAGT, followed by the reverse compliment of a second primer part including the following base pairs: CCAGCAGCCGCGGTAAT. In variations of the examples, the nucleic acid material of the second sample can additionally or alternatively comprise RNA material. Furthermore, additional example barcode sequences are presented in Table 3;

however, Block S52 of the method 500 can additionally or alternatively include any other suitable barcode sequences configured relative to primer sequences in any other suitable manner.

Block S53 recites: preparing a third solution upon combination of a first portion of the first solution and a second portion of the second solution, wherein the second portion includes a reference quantity of nucleic acid material. Block S53 functions to create a combined solution that can be amplified, sequenced, and analyzed to determine a quantity of nucleic acid molecules having the target sequence in the first solution, as in Block S57 below. Combination can include a pipetting technique to combine the first portion of the first solution and the second portion of the second solution in a précises precise manner that enables determination of the reference quantity of nucleic acid material having the target sequence and the reference sequence; however, combination can additionally or alternatively include any other suitable method of sample solution combination. In Block S53, the reference quantity of nucleic acid material is preferably known, and functions to facilitate normalization of a number of reads from part of the first solution, in order to enable determination of a quantity of nucleic acid molecules having the target sequence in the first solution. Block S53 is preferably implemented at an embodiment, variation, or example of the sample processing module 230 of the system 200 described in relation to Block S130 above; however, Block S53 can additionally or alternatively be implemented using any other suitable system.

Block S54 recites: preparing a fourth solution upon amplifying nucleic acid material of the third solution, which functions to facilitate sequencing in Block S54 by providing a sufficient quantity of nucleic acid material from the third solution for sequencing. Block S54 is preferably implemented at an embodiment, variation, or example of the sample processing module described in relation to Block S130 above; however, Block S54 can additionally or alternatively be implemented at any other suitable system configured to amplify and/or sequence nucleic acid content of a biological sample. In Block S54, amplification is preferably performed according to the embodiments, variations, and/or examples of Blocks S130 and S35 described above; however, amplification in Block S54 can alternatively be performed in any other suitable manner.

Block S55 recites: generating the sequence dataset based upon sequencing nucleic acid material of the fourth solution, which functions to identify sequences of nucleic acid material amplified in Block S54, in order to facilitate determination of values of parameters based upon specific sequences that can be used to determine a quantity of nucleic acid materials having the target sequence in the first solution. Block S55 is preferably implemented at an embodiment, variation, or example of the sample processing module described in relation to Block S130 above; however, Block S55 can additionally or alternatively be implemented at any other suitable system configured to amplify and/or sequence nucleic acid content of a biological sample. In Block S55, sequencing is preferably performed according to the embodiments, variations, and/or examples of Blocks S130 and S37 described above; however, sequencing in Block S55 can alternatively be performed in any other suitable manner.

Block S56 recites: from the sequence dataset, determining a reference number of reads associated with the reference sequence and a total number of reads associated with the target sequence, which functions to determine values of read parameters that can be used to determine the quantity of nucleic acid molecules having the target sequence in the first solution, as in Block S57. Quantification of sequence reads associated with the reference sequence and sequence reads associated with the target sequence is preferably performed at an embodiment, variation, or example of the processing system 240 of the system 200 described in relation to Block S140 above; however, quantification in Block S56 can additionally or alternatively be performed at any other suitable system configured to identify similar or identical sequence reads, compare the sequence reads to reference sequences and target sequences, and quantify reads associated with the reference sequence and sequence reads associated with the target sequence.

Block S57 recites: determining the quantity of nucleic acid molecules having the target sequence based upon the total number of reads, the reference number of reads, and the reference quantity of nucleic acid material. Block S57 functions to take read counts determined in Block S56 and the reference quantity of nucleic acid material known from Block S53, to determine a quantity of nucleic acid molecules having the target sequence in the first solution, based upon a back-calculation method. In one variation of Block S57, the quantity of nucleic acid molecules having the target sequence in the first solution can be determined based upon calculation of a difference between the total number of reads and the reference number of reads, wherein the difference is multiplied by a ratio between the reference quantity of nucleic acid material and the reference number of reads. As such, in the example, the quantity of nucleic acid molecules having the target sequence, y, can be determined according to expression [1], where b is the total number of reads, where x is the reference quantity of nucleic acid material of Block S53, and where a is the reference number of reads:

$$y=(b-a)*(x/a) \qquad [1]$$

In Block S57, the quantity of nucleic acid molecules having the target sequence in the first solution can, however, be determined in any other suitable manner based upon the total number of reads, the reference number of reads, and the reference quantity of nucleic acid material.

Blocks S51-S57 can be further adapted to variations wherein multiple target sequences are of interest. For instance, for a given target sequence n, the quantity of nucleic acid molecules having the target sequence, $y_n$, can be determined according to expression [2], where $b_n$ is the total number of reads, where $x_n$ is a reference quantity of nucleic acid material having the target sequence coupled with a reference sequence, and where $a_n$ is the reference number of reads having the reference sequence, post amplification and sequencing:

$$y_n=(b_n-a_n)*(x_n/a_n) \qquad [2]$$

With multiple target sequences, relative abundances of nucleic acid molecules having the respective target sequences can be determined by relating versions of expression [2], determined for each target sequence, to each other. In one such example applied to a first target sequence and a second target sequence, a relative abundance between nucleic acid molecules having the first target sequence, $y_1$, and nucleic acid molecules having the second target sequence, $y_2$, can be determined according to expression [3], where $b_1$ is the total number of reads having a first reference sequence post amplification and sequencing, where $b_2$ is the total number of reads having a second reference sequence post amplification and sequencing, where $x_1$ is a reference quantity of nucleic acid material having the first target sequence coupled with the first reference sequence, where $x_2$ is a reference quantity of nucleic acid material having the second target sequence coupled with the second reference sequence, where $a_1$ is the reference number of reads having the first reference sequence, post amplification and sequencing, and where $a_2$ is the reference number of reads having the first reference sequence, post amplification and sequencing:

$$y_1/y_2=[(b_1-a_1)/(b_2-a_2)]*(x_1/x_2)*(a_2/a_1) \quad [3]$$

In expression [3], if the total number of reads having the first reference sequence is identical to the total number of reads having the second reference sequence, and if the reference quantity of nucleic acid material having the first target sequence coupled with the first reference sequence is equal to the reference quantity of nucleic acid material having the second target sequence coupled with the second reference sequence, expression [3] can be simplified as expression [4] in order to facilitate determination of the relative abundances between nucleic acid molecules having the first target sequence, $y_1$, and nucleic acid molecules having the second target sequence, $y_2$:

$$y_1/y_2=[(b-a_1)/(b-a_2)]*(a_2/a_1) \quad [4]$$

Determination of relative abundances of nucleic acid molecules having target sequences can, however, be determined in any other suitable manner according to expanded variations of Block S57.

Block S58 recites: associating the sequence dataset with the individual based upon the reference number of reads, which functions to verify the identity of a sample and/or sequence dataset based upon detection and characterization parameters derived from the reference number of reads determined in Block S56. Block S58 is preferably performed at an embodiment, variation, or example of the processing system described in relation to Block S140 above; however Block S58 can additionally or alternatively be implemented using any other suitable computing system configured to determine parameters derived from sequencing data for purposes of sample identification.

Similar to Block S43 described above, the processing system implementing Block S58 can further comprise a module configured to compare the reference number of reads against all synthetic nucleic acid modules used as identification sequences in the method 100 and/or system 200, which functions to enable identification of cross-contamination between samples. For instance, the module can be configured to detect presence of one or more unanticipated synthetic nucleic acid sequences present in the first solution or processed versions thereof (e.g., as determined post-amplification and post-sequencing), which can indicate that samples were mixed together and should not be trusted for accurate characterization. Upon identification of an unanticipated presence of an unanticipated synthetic nucleic acid molecule in the first solution, Block S58 can further include identifying another sample associated with the unanticipated synthetic nucleic acid molecule, and performing an error correction action. In variations, the error correction action can comprise one or more of: analyzing the other sample to determine if contamination only occurred in one direction (e.g., the other sample contaminated the first sample, but the first sample did not contaminate the other sample) or in both directions, notifying an entity of the sample handling network of potential contamination, notifying an entity of the sample handling network that further processing of a contaminated sample should not continue, notifying the individual providing the first sample that an additional sample may need to be re-provided, and any other suitable error correction action. Block S58 can, however, comprise any other suitable steps or blocks configured to enhance sample identification and/or identification of sample contamination.

While processing and identification in Blocks S51-S58 are described in relation to analysis of a microbiome portion of a sample from an individual, Blocks S51-S58 can be adapted to methods for performing analyses on any other suitable biological sample, using any other suitable biological component that can detected and/or quantified throughout processing as a barcode/identifying feature (e.g., distribution of synthetic organelles for identification purposes, distribution of cell populations for identification purposes, etc.).

1.5 Insight Generation and Sharing

Block S150 recites: at the processing system, generating an analysis based upon a set of features related to the microorganism portion, which functions to transform outputs of Block S140 into features that can be processed algorithmically to determine microbiome-based insights at the individual level and population of individuals level. As shown in FIG. 12, Block S150 can include generating features derived from compositional aspects of the microbiome associated with the sample S151, and generating an analysis based upon features derived from compositional aspects of the microbiome associated with the sample S152. Blocks S150-S152 are preferably implemented at least in part at an embodiment, variation, or example of the processing system 240 of the system 200 described in relation to Block S140 above; however, Blocks S150-S152 can additionally or alternatively be implemented using any other suitable system(s).

Upon identification of represented groups of microorganisms of the microbiome associated with a sample, based upon the mapping and alignment operations of Block S140, generating features derived from compositional aspects of the microbiome associated with a sample can be performed in Block S151. In one variation, generating features can include generating features that describe the presence or absence of certain taxonomic groups of microorganisms. Additionally or alternatively, generating features can include inferring phylogenetic traits associated with aligned, mapped, and/or merged reads, which can include determining placement of sequences on a reference phylogenetic tree of microorganisms. Additionally or alternatively, generating features can include generating features describing quantities of represented taxonomic groups. Additionally or alternatively, generating features can include generating features describing diversity of different microorganism groups and relative abundance of different microorganism groups, for instance, using a Genome Relative Abundance and Average size (GAAS) approach and/or a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Block S120 can, however, include generation of any other suitable feature(s) derived from sequencing and mapping of nucleic acids of a biological sample.

Upon feature generation in Block S151, generating an analysis based upon the generated features can be performed in Block S152. In generation of the analysis, Block S152 can implement supplementary data that can enhance correlations and/or predictions included in the analysis. As such, Block S152 can include Block S153, which recites: receiving a supplementary dataset that includes demographic and behavioral information from at least one of the individual and the population of individuals. In Block S153, the supplementary dataset preferably includes survey-derived data, but can additionally or alternatively include any one or more of: contextual data derived from sensors, medical data, and any other suitable type of data.

In variations of Block S153 including reception of survey-derived data, the survey-derived data preferably provides physiological, demographic, and behavioral information in association with an individual. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. In one example, a survey configured to facilitate generation of the supplementary dataset includes a question related to height of the individual, weight of the individual, diet of the individual, alcohol consumption of the individual, smoking behavior of the individual, caffeinated beverage consumption of the individual, and diet beverage consumption of the individual. Survey-derived data can thus include quantitative data and/or qualitative data that can be converted to quantitative data (e.g., using scales of severity, mapping of qualitative responses to quantified scores, etc.). A specific example of a survey is shown in FIG. 13.

In facilitating reception of survey-derived data, Block S153 can include providing one or more surveys to an individual, or to an entity (e.g., healthcare provider, caretaker, spouse, relative, etc.) associated with the individual. Surveys can be provided in person (e.g., in coordination with sample provision and reception from an individual), electronically (e.g., during account setup by an individual in Block S110, at an application executing at an electronic device of an individual), and/or in any other suitable manner.

Additionally or alternatively, portions of the supplementary dataset of Block S153 can be derived from sensors associated with the individual(s) (e.g., sensors of wearable computing devices, sensors of mobile devices, biometric sensors associated with the user, etc.). As such, Block S153 can include receiving one or more of: physical activity- or physical action-related data (e.g., accelerometer and gyroscope data from a mobile device or wearable electronic device of an individual), environmental data (e.g., temperature data, elevation data, climate data, light parameter data, etc.), patient nutrition or diet-related data (e.g., data from food establishment check-ins, data from spectrophotometric analysis, etc.), biometric data (e.g., data recorded through sensors within the patient's mobile computing device, data recorded through a wearable or other peripheral device in communication with the patient's mobile computing device), location data (e.g., using GPS elements), and any other suitable data. Additionally or alternatively, portions of the supplementary dataset can be derived from medical record data and/or clinical data of the individual(s). As such, portions of the supplementary dataset of Block S153 can be derived from one or more electronic health records (EHRs) of the individual(s). The supplementary dataset received in Block S153 can, however, comprise any other suitable type of supplementary data.

As such, generating the analysis in Block S152 can include generating values of parameters derived from features of Block S151, generation of associations between features (or values of parameters derived from features) and information derived from the supplementary dataset, generation of confidence metrics or measures of correlational strength between microbiome-based features (or values of parameters derived from features) and behavioral or demographic characteristics derived from the supplementary dataset, and/or any other suitable insights. In some variations, portions of the analysis can support or provide diagnostic tools that can characterize an individual (e.g., in terms of behavioral traits, in terms of medical conditions, in terms of demographic traits, etc.) based upon their microbiome composition, and/or predict an individual's microbiome composition based upon one or more of their behavioral traits, medical conditions, demographic traits, and any other suitable traits.

In Block S152, portions of an analysis can be derived from machine learning-based techniques, whereby input data derived from generated features can be processed with a training dataset having features linked to candidate classifications (e.g., derived from a supplementary dataset) to provide a classification model that links microbiome-based features to other characteristics of an individual. In one variation, a classification model generated in Block S152 can be trained to identify microbiome-based features and/or feature combinations that have high degrees (or low degrees) of predictive power in accurately predicting a classification of an individual. As such, refinement of the classification model with the training dataset identifies feature sets (e.g., of individual features, of combinations of features) having high correlation with specific classifications of individuals.

Feature selection approaches can include correlation feature selection (CFS) methods, consistency methods, relief methods, information gain methods, symmetrical uncertainty methods, and/or any other suitable methods of feature selection. In one variation, the feature vectors can include features related to one or more of: microbiome diversity metrics (e.g., in relation to distribution across taxonomic groups, in relation to distribution across bacterial, viral, and/or fungal groups), presence of taxonomic groups in one's microbiome, representation of specific genetic sequences (e.g., 16S sequences, 18S sequences, ITS sequences, etc.) in one's microbiome, relative abundance of taxonomic groups in one's microbiome, microbiome resilience metrics (e.g., in response to a perturbation determined from the supplementary dataset), and any other suitable features derived from the microbiome diversity dataset and/or the supplementary dataset. Additionally, combinations of features can be used in a feature vector, wherein features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, representation of a specific 18S sequence in one's microbiome, representation of an ITS sequence in one's microbiome, and relative abundance of a first phylum over a second phylum of bacteria. However, the feature vectors can additionally or alternatively be determined in any other suitable manner.

As shown in FIG. 14, in one variation of Block S152 involving generation of a classification model using a machine-learning classifier, the classification model can be generated and trained according to a random forest predictor (RFP) algorithm that combines bagging (i.e., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the classification model, in identifying features that are strong in predicting classifications can be increased substantially. In this variation, measures to prevent bias (e.g., sampling bias) and/or account for an amount of bias can be included during processing to increase robustness of the model.

While a random forest method of machine learning is described in the variation above, Block S140 can additionally or alternatively utilize any other suitable machine learning algorithms in forming and/or training the classification model. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm, some forms of which are described in U.S. App. No. 61/953,683, entitled "Multiplex Markers" and filed on 14 Mar. 2014.

Additionally or alternatively, portions of the analysis generated in Block S150 can be generated using statistical methods and tools, including one or more of: basic statistics, scatterplot analysis, principal component analysis (PCA), edge PCT, UniFrac analyses (e.g., to calculate distances between identified microorganism communities using phylogentic information), multivariate analyses, analyses of variance, cluster analysis, Kantorovich-Rubinstein metrics, and any other suitable statistical method.

Block S160 recites: from the processing system, transmitting information derived from values of the set of parameters to the individual, which functions to share insights derived from the analysis of Block S150 with one or more individuals. In Block S160, transmitting information to an individual can be facilitated by way of the user account for the individual, set up in variations of Block S113, such that the information is accessible at an electronic device (e.g., personal computer, smart phone, head-mounted wearable computing device, wrist-mounted wearable computing device, tablet, laptop, netbook, etc.) of the individual. Additionally or alternatively, information can be provided to the individual in the form of a printed report, an electronic document (e.g., a PDF), as raw data, and/or in any other suitable form.

In variations, the information can indicate one or more of: the presence of one or more microorganisms in an individual's microbiome (e.g., the presence of *Streptococcus* bacteria in an oral sample); the absence of one or more microorganisms in an individual's microbiome; the abundance (e.g., relative abundance, absolute abundance) of one or more microorganisms in an individual's microbiome; and comparisons between the microbiome composition of an individual relative to one or more subpopulations of individuals or populations of individuals based upon any physiological, demographic, or behavioral classification. Information can additionally or alternatively be provided in Block S160 in the context of average, typical, or healthy ranges. In one example, as shown in FIG. 15A, information provided to an individual can depict an amount of a given type of microorganism present in a sample from an individual with reference to an average range of amounts of the given type of microorganism and reference to a full range of amounts of the given type of microorganism from a population of individuals.

Information provided in Block S160 can additionally or alternatively be organized into different user levels, wherein each user level can have access to different data, analyses, and/or other tools. For instance, user levels can be organized according to one or more of: profession (e.g., scientist, researcher, clinician, healthcare provider, etc.), status (e.g., consumer, patient), and any other classification of user level. For instance, in one example, scientists/researchers can be permitted to upload research or study data, compare research or study data to other research or study data, compare research or study data to data from different subpopulations of individuals, and predict results of a larger study from results of a pilot study. In another example, clinicians can be permitted to view information pertaining to patients, and patients can be permitted to share information with their clinicians.

Information provided in Block S160 can additionally or alternatively be presented within a certain time from receipt of a sample from an individual (e.g. within a period of 90 days, etc.), and in variations wherein multiple samples are provided by an individual, information can be provided with a time-varying and/or sample-site adjustable component. Furthermore, information can be provided with respect to any suitable number of microorganism taxonomic groups (e.g., from 1 to 10,000 species, from 10,000 genera, etc.).

In Block S160, information can be provided (e.g., in a printed report, in an electronic document) or rendered at an electronic display using visualization tools including one or more of: visualization tools for taxonomic data (e.g., tables and/or graphics showing domain, kingdom, phylum, class, order, family, genus, species, and/or subspecies relationships, an example of which is shown in FIG. 15F), phylogenetic trees, cladograms, dendrograms, pie charts, bar charts, scatter plots, and any other suitable visualization tool. Furthermore, a user interface associated with a user account can provide controls, examples of which are shown in FIG. 15B, to adjust levels of detail provided to the individual, to adjust types of comparison information provided to the individual, to adjust a taxonomy level of an analysis provided to the individual, and/or to adjust any other suitable parameter pertaining to information provided to the individual.

In examples shown in FIG. 15C, information provided in Block S160 can be rendered at a display in the form of one or more of: a scatterplot 610, a network chart 620, a pie chart 630, a graphic showing microbiome-based parameters relative to collection sites of an individual 640, a set of comparison diagrams between microbiome compositional features of an individual in comparison to one or more subpopulations of individuals 650, and a set of comparison matrices between microbiome compositional features of an individual in comparison to one or more subpopulations of individuals 660. In one example, as shown in FIG. 15D, Block S160 can include rendering a pie chart 710 displaying microbiome compositional information for a sample from an individual, with a legend 720 describing represented microbiome components. In another example, as shown in FIG. 15B, Block S160 can include rendering a set of pie charts 810, 820 comparing the microbiome composition of a sample from an individual to an average of all samples provided from a population of individuals at a taxonomic level (e.g., genus level), in coordination with a user interface 830 that allows an individual to receive information at other taxonomic levels (e.g., the domain level, the phylum level, the class level, the order level, the family level, the genus level, the species level, the sub-species level) upon receiving of an input at the user interface by the individual. In yet another example, as shown in FIG. 15E, Block S160 can include rendering a set of bar charts 910, 920, 930, 940 comparing the microbiome composition of a sample from an individual to the average microbiome composition for a subpopulation of healthy omnivores, the average microbiome composition for a subpopulation of vegetarians, and the average microbiome composition for the entire population of individuals analyzed.

2. Specific Application

A specific application of example workflows is described, wherein in a workflow, an individual receives a sampling kit, interacts with the sampling kit, and provides samples for analysis by using components of the sampling kit. In the workflow, the sample(s) from an individual is received, processed, analyzed, and used to provide information to the individual.

In the specific application of the first workflow, an individual receives a sampling kit, transmits one or more samples from one or more collection sites into sample containers of the sampling kit, and returns the sample containers to a sample handling network by way of packaging receptacles included in the sampling kit. Registration codes (e.g., barcodes) associated with the sampling kit and the sample container(s) are logged, at the sample handling network, for tracking. Samples from the individual are then introduced into an automated sample handling workflow implementing a sample processing module and a processing system, wherein nucleic acids from the samples are purified, amplified, tagged, and sequenced. Data derived from sequenced nucleic acids is then associated with samples based upon identifiers (e.g., identification sequences, barcodes, tags, etc.) and analyzed to derive microbiome information. Information pertaining to the microbiome of the individual is then presented to the individual by way of an interactive website that provides renderings of graphs, charts, and comparisons between the microbiome of each sample from the individual, and relevant subpopulations of individuals, relevant ranges of metrics, and/or relevant microbiome-based studies.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for analyzing a microbiome of an individual, comprising:

providing a sampling kit to the individual at a remote location, the sampling kit including a sample container having a pre-process reagent component and configured to receive a sample from a collection site of the individual;

from the remote location, receiving the sample container with the sample from the collection site of the individual;

with a bridge amplification substrate of a next generation sequencing platform of a sample processing system, generating a microbiome sequence dataset based upon sequencing nucleic acid content of a microorganism portion of the sample;

at computing devices of the processing system in communication with the next generation sequencing platform, identifying a set of microorganisms represented in the microorganism portion based upon performance of a mapping operation on portions of the microbiome sequence dataset;

at the processing system, generating an analysis based upon a set of features related to the microorganism portion; and from the processing system, transmitting information derived from the analysis to the individual.

2. The method of claim 1, wherein providing the sampling kit to the individual comprises providing instructions to the individual regarding provision of the sample, providing instructions to the individual regarding pre-processing of the sample, and providing instructions to the individual regarding setup of a user account within a social networking system configured to provide microbiome-derived insights to the individual.

3. The method of claim 2, wherein providing instructions regarding provision of the sample comprises instructing the individual to use permeable substrate of the sampling kit to swab used toilet paper to collect a feces sample, to stir the feces sample within the sample container with the sample preservation component, and to agitate the sample container with the feces sample in order to pre-process the sample.

4. The method of claim 2, wherein providing instructions to the individual regarding pre-processing of the sample comprises guiding the user in accessing instructional content provided through the user account of the social networking system, the instructional content including video instructions to stir the sample within the sample container with the sample preservation component, and to agitate the sample container with the sample.

5. The method of claim 4, wherein receiving the sample container comprises receiving the sample in a pre-processed state of lysis by individual prior to reception.

6. The method of claim 5, wherein receiving comprises receiving a set of sample containers each containing a pre-processed sample from one of a population of individuals, and wherein the population of individuals comprises individuals of different demographics, different health conditions, different living situations, different dietary habits, different sexual orientations, and different substance-use behaviors.

7. The method of claim 6, wherein generating the analysis comprises receiving a supplementary dataset, by way of the social networking system, comprising survey data with information regarding demographic and behavioral information of each of the population of individuals.

8. The method of claim 7, wherein generating the analysis comprises training a machine-learning classifier to generate a ranking of features of the set of features having high predictive power for demographic classifications of the population of individuals and behavioral classifications of the populations of individuals in association with microbiome composition, determined based upon the supplementary dataset.

9. The method of claim 1, wherein generating the microbiome sequence dataset comprises amplifying nucleic acid material of the sample, with a forward primer and a reverse primer having a forward index sequence, a forward barcode sequence, a linker sequence configured to reduce homogeneity in amplification, a transposase sequence corresponding to a transposase binding site, a target sequence configured to target a target region of nucleic acid material in the sample, a reverse barcode sequence, and a reverse index sequence, wherein the forward barcode sequence and the reverse barcode sequence facilitate unique association of the sample with the individual amongst a set of samples, from a population of individuals, received at the sample handling network.

10. The method of claim 9, wherein generating the microbiome sequence dataset comprises using microbiome standards prepared with colony forming units of *Bacillus subtilis, Legionella pneumophilia, Clostridium perfringens*, and *Enterococcus faecalis*, in a ratio of 100:1000:2:1.

11. The method of claim 1, wherein performance of the mapping operation on portions of the microbiome sequence dataset comprises performing quality filtering of reads of the microbiome sequence dataset, and identifying and removing human genome-derived sequences from the microbiome sequence dataset.

12. The method of claim 11, wherein sequence reads of the microbiome sequence dataset are encoded into a binary sequence and hashed using a simhash algorithm with clustering in the mapping operation.

13. The method of claim 1, wherein transmitting information derived from the analysis to the individual comprises rendering a graphic derived from the analysis at a display of an electronic device associated with the individual, upon accessing of the user account by the individual at the electronic device, wherein the graphic depicts a distribution of taxonomic groups of microorganisms present in the sample with comparisons to distributions from other groups of individuals.

14. The method of claim 1, wherein generating the microbiome sequence dataset comprises simultaneously amplifying an entire 16S region for each of the set of microorganisms represented in the sample using universal primers; fragmenting amplicons of the entire 16S region for each of the set of microorganisms to generate a set of amplicon fragments; and generating an assessment of the set of amplicon fragments, wherein the assessment includes at least one of microorganism population characteristics, microorganism species identifications, and identified target microorganism sequences.

15. The method of claim 14, wherein generating the assessment comprises implementing a Bayesian statistics algorithm for characterization of the microbiome portion of the sample based upon at least one of species identification, strain identification, and gene identification; assembling a full gene based upon sequenced amplicon fragments; and detecting specific sequences from the set of amplicon fragments.

16. A system for analyzing a microbiome of an individual comprising:
    a sampling kit including a sample container having a pre-process reagent component and configured to receive a sample from a collection site of the individual;
    a sample processing system comprising a bridge amplification substrate of a next generation sequencing platform configured to receive the sample container, associate the sample container with the individual, and generate a microbiome sequence dataset based upon sequencing nucleic acid content of a microorganism portion of the sample with the bridge amplification substrate; and
    a computing device, during operation, communicates with the next generation sequencing platform of the sample processing system and identifies a set of microorganisms represented in the microorganism portion based upon performance of a mapping operation on portions of the microbiome sequence dataset, generates an analysis based upon a set of features related to the microorganism portion, and transmits information derived from the analysis to the individual.

17. The system of claim 16, wherein the sampling kit includes a set of permeable substrates, a sample process reagent configured to facilitate sample extraction from the collection site, a return receptacle, and instructions for the individual regarding provision of the sample to the sample handling network using the return receptacle, regarding pre-processing of the sample, and regarding setup of a user account within a social networking system configured to provide microbiome-derived insights derived from the analysis to the individual.

18. The system of claim 17, wherein the sample processing system receives the sample in a pre-processed state of lysing, associates the sample with the individual and the user account of the individual, and transmits microbiome-derived information to the individual upon accessing of the user account within the social networking system by the individual.

19. The system of claim 18, wherein during operation, the computing device receives a supplementary dataset, by way of the social networking system, comprising survey data with information regarding demographic and behavioral information of each of a population individuals, and trains a machine-learning classifier to generate a ranking of features of the set of features having high predictive power for at least one of demographic classifications and behavioral classifications determined based upon the supplementary dataset.

20. The system of claim 19, wherein during operation, the computing device renders a graphic derived from the analysis at a display of an electronic device associated with the individual, upon accessing of the user account by the individual at the electronic device, wherein the graphic depicts a distribution of taxonomic groups of microorganisms present in the sample with comparisons to distributions from other groups of individuals.

21. A method for analyzing a microbiome of an individual, comprising:
  providing a sampling kit to the individual at a remote location, the sampling kit configured to provide:
    a sample container having a lysing component and a sample preservation component and configured to receive a sample from a collection site of the individual, and
    instructions for providing the sample, pre-processing the sample, and setting up a user account within a social networking system;
  from the remote location, receiving the sample container with the sample from the collection site of the individual, the sample pre-processed by the individual at the remote location;
  with a bridge amplification substrate of a next generation sequencing platform of a sample processing system, generating a microbiome sequence dataset based upon sequencing nucleic acid content of a microorganism portion of the sample,
    wherein generating the microbiome sequence dataset comprises simultaneously amplifying an entire 16S region for each microorganism of the microorganism portion of the sample using universal primers; fragmenting amplicons of the entire 16S region for each microorganism of the microorganism portion to generate a set of amplicon fragments; and generating an assessment of the set of amplicon fragments, wherein the assessment includes at least one of microorganism population characteristics, microorganism species identifications, and identified target microorganism sequences;
  at computing devices of the processing system, identifying a set of microorganisms represented in the microorganism portion based upon performance of a mapping operation on portions of the microbiome sequence dataset;
  at the processing system, generating an analysis including values of a set of parameters related to the microorganism portion; and
  from the processing system, transmitting information derived from the analysis to the individual, as facilitated by the user account within the social networking system.

22. The method of claim 21, wherein providing instructions to the individual regarding pre-processing the sample comprises guiding the user in accessing instructional content provided through the user account of the social networking system, the instructional content including video instructions to stir the sample within the sample container with the sample preservation component, and to agitate the sample container with the sample.

* * * * *

SEQUENCE LISTING

```
<160> NUMBER OF SEQ ID NOS: 269

<210> SEQ ID NO 1
<211> LENGTH: 20
<212> TYPE: DNA
<213> ORGANISM: Unknown
<220> FEATURE:
<223> OTHER INFORMATION: Synthesized Degenerate Sequence

<400> SEQUENCE: 1
ccagcascyg cggtaattcc                                              20

<210> SEQ ID NO 2
<211> LENGTH: 18
<212> TYPE: DNA
<213> ORGANISM: Unknown
<220> FEATURE:
<223> OTHER INFORMATION: Synthesized Degenerate Sequence

<400> SEQUENCE: 2
actttcgttc ttgatyra                                                18

<210> SEQ ID NO 3
<211> LENGTH: 19
<212> TYPE: DNA
<213> ORGANISM: Unknown
<220> FEATURE:
<223> OTHER INFORMATION: Synthetic microbiome primer sequence

<400> SEQUENCE: 3
ccagcagctg cggtaattc                                               19

<210> SEQ ID NO 4
<211> LENGTH: 16
<212> TYPE: DNA
<213> ORGANISM: Unknown
<220> FEATURE:
<223> OTHER INFORMATION: Synthesized Synthetic Barcode Sequence

<400> SEQUENCE: 4
tacgacggta cacagt                                                  16

<210> SEQ ID NO 5
<211> LENGTH: 18
<212> TYPE: DNA
<213> ORGANISM: Unknown
<220> FEATURE:
<223> OTHER INFORMATION: Synthesized Primer Sequence

<400> SEQUENCE: 5
tcgatcaaga acgaaagt                                                18

<210> SEQ ID NO 6
<211> LENGTH: 20
<212> TYPE: DNA
<213> ORGANISM: Unknown
<220> FEATURE:
<223> OTHER INFORMATION: Synthesized Primer Sequence

<400> SEQUENCE: 6
```
tggtcattta gaggaagtaa                                                    20

<210> SEQ ID NO 7
<211> LENGTH: 18
<212> TYPE: DNA
<213> ORGANISM: Unknown
<220> FEATURE:
<223> OTHER INFORMATION: Synthesized Primer Sequence

<400> SEQUENCE: 7
tgcgttcttc atcgatgc                                                      18

<210> SEQ ID NO 8
<211> LENGTH: 20
<212> TYPE: DNA
<213> ORGANISM: Unknown
<220> FEATURE:
<223> OTHER INFORMATION: Synthesized Primer Sequence

<400> SEQUENCE: 8
tggtcattta gaggaagtaa                                                    20

<210> SEQ ID NO 9
<211> LENGTH: 16
<212> TYPE: DNA
<213> ORGANISM: Unknown
<220> FEATURE:
<223> OTHER INFORMATION: Synthesized Synthetic Barcode Sequence

<400> SEQUENCE: 9
tccgaaaggg ctttga                                                        16

<210> SEQ ID NO 10
<211> LENGTH: 18
<212> TYPE: DNA
<213> ORGANISM: Unknown
<220> FEATURE:
<223> OTHER INFORMATION: Synthesized Primer Sequence

<400> SEQUENCE: 10
gcatcgatga agaacgca                                                      18

<210> SEQ ID NO 11
<211> LENGTH: 19
<212> TYPE: DNA
<213> ORGANISM: Unknown
<220> FEATURE:
<223> OTHER INFORMATION: Synthesized Degenerate Primer Sequence

<400> SEQUENCE: 11
gtgccagcmg ccgcggtaa                                                     19

<210> SEQ ID NO 12
<211> LENGTH: 20
<212> TYPE: DNA
<213> ORGANISM: Unknown
<220> FEATURE:
<223> OTHER INFORMATION: Synthesized Degenerate Primer Sequence

<400> SEQUENCE: 12
ggactachvg ggtwtctaat                                                    20

<210> SEQ ID NO 13
<211> LENGTH: 20
<212> TYPE: DNA
<213> ORGANISM: Unknown

```
<220> FEATURE:
<223> OTHER INFORMATION: Synthesized Primer Sequence

<400> SEQUENCE: 13
agagtttgat cctggctcag                                              20

<210> SEQ ID NO 14
<211> LENGTH: 17
<212> TYPE: DNA
<213> ORGANISM: Unknown
<220> FEATURE:
<223> OTHER INFORMATION: Synthesized Primer Sequence

<400> SEQUENCE: 14
attaccgcgg ctgctgg                                                 17

<210> SEQ ID NO 15
<211> LENGTH: 20
<212> TYPE: DNA
<213> ORGANISM: Unknown
<220> FEATURE:
<223> OTHER INFORMATION: Synthesized Primer Sequence

<400> SEQUENCE: 15
agagtttgat cctggctcag                                              20

<210> SEQ ID NO 16
<211> LENGTH: 15
<212> TYPE: DNA
<213> ORGANISM: Unknown
<220> FEATURE:
<223> OTHER INFORMATION: Synthesized synthetic barcode sequence

<400> SEQUENCE: 16
acccgtactt ctagt                                                   15

<210> SEQ ID NO 17
<211> LENGTH: 17
<212> TYPE: DNA
<213> ORGANISM: Unknown
<220> FEATURE:
<223> OTHER INFORMATION: Synthesized Primer Sequence

<400> SEQUENCE: 17
ccagcagccg cggtaat                                                 17

<210> SEQ ID NO 18
<211> LENGTH: 23
<212> TYPE: DNA
<213> ORGANISM: Unknown
<220> FEATURE:
<223> OTHER INFORMATION: Synthesized Fungal Primer Sequence

<400> SEQUENCE: 18
cttggtcatt tagaggaaag taa                                          23

<210> SEQ ID NO 19
<211> LENGTH: 20
<212> TYPE: DNA
<213> ORGANISM: Unknown
<220> FEATURE:
<223> OTHER INFORMATION: Synthesized Fungal Primer Sequence

<400> SEQUENCE: 19
gctgcgttct tcatcgatgc                                              20
```

<210> SEQ ID NO 20
<211> LENGTH: 22
<212> TYPE: DNA
<213> ORGANISM: Unknown
<220> FEATURE:
<223> OTHER INFORMATION: Synthesized Bacteria and Archea 16s Primer
      Sequence

<400> SEQUENCE: 20
tcagagtttg atcctggctc ag                                            22

<210> SEQ ID NO 21
<211> LENGTH: 17
<212> TYPE: DNA
<213> ORGANISM: Unknown
<220> FEATURE:
<223> OTHER INFORMATION: Synthesized Bacteria and Archea 16s Primer
      Sequence

<400> SEQUENCE: 21
attaccgcgg ctgctgg                                                  17

<210> SEQ ID NO 22
<211> LENGTH: 22
<212> TYPE: DNA
<213> ORGANISM: Unknown
<220> FEATURE:
<223> OTHER INFORMATION: Synthesized Bacteria and Archea 16s Degenerate
      Primer Sequence

<400> SEQUENCE: 22
cgtgtgccag cmgccgcggt aa                                            22

<210> SEQ ID NO 23
<211> LENGTH: 22
<212> TYPE: DNA
<213> ORGANISM: Unknown
<220> FEATURE:
<223> OTHER INFORMATION: Synthesized Bacteria and Archea 16s Degenerate
      Primer Sequence

<400> SEQUENCE: 23
ccggactach vgggtwtcta at                                            22

<210> SEQ ID NO 24
<211> LENGTH: 20
<212> TYPE: DNA
<213> ORGANISM: Unknown
<220> FEATURE:
<223> OTHER INFORMATION: Synthesized Eukaryote 18s Degenerate Primer
      Sequence

<400> SEQUENCE: 24
ccagcascyg cggtaattcc                                               20

<210> SEQ ID NO 25
<211> LENGTH: 18
<212> TYPE: DNA
<213> ORGANISM: Unknown
<220> FEATURE:
<223> OTHER INFORMATION: Synthesized Eukaryote 18s Degenerate Primer
      Sequence

<400> SEQUENCE: 25
actttcgttc ttgatyra                                                 18

```
<210> SEQ ID NO 26
<211> LENGTH: 20
<212> TYPE: DNA
<213> ORGANISM: Unknown
<220> FEATURE:
<223> OTHER INFORMATION: Synthesized Eukaryotic 18s Primer Sequence

<400> SEQUENCE: 26
ccagcascyg cggtaattcc                                              20

<210> SEQ ID NO 27
<211> LENGTH: 18
<212> TYPE: DNA
<213> ORGANISM: Unknown
<220> FEATURE:
<223> OTHER INFORMATION: Synthesized Eukaryotic 18s Primer Sequence

<400> SEQUENCE: 27
actttcgttc ttgatyra                                                18

<210> SEQ ID NO 28
<211> LENGTH: 22
<212> TYPE: DNA
<213> ORGANISM: Unknown
<220> FEATURE:
<223> OTHER INFORMATION: Synthesized Fungal Ribosomal ITS primer
      sequence

<400> SEQUENCE: 28
cttggtcatt tagaggaagt aa                                           22

<210> SEQ ID NO 29
<211> LENGTH: 20
<212> TYPE: DNA
<213> ORGANISM: Unknown
<220> FEATURE:
<223> OTHER INFORMATION: Synthesized Fungal Ribosomal ITS primer
      sequence

<400> SEQUENCE: 29
gctgcgttct tcatcgatgc                                              20

<210> SEQ ID NO 30
<211> LENGTH: 19
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 30
gtgccagcmg ccgcggtaa                                               19

<210> SEQ ID NO 31
<211> LENGTH: 20
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 31
ggactachvg ggtwtctaat                                              20

<210> SEQ ID NO 32
<211> LENGTH: 20
<212> TYPE: DNA
```

-continued

```
<213> ORGANISM: Unknown
<220> FEATURE:
<223> OTHER INFORMATION: Synthesized Bacterial Ribosomal 16S primer
      sequence

<400> SEQUENCE: 32
agagtttgat cctggctcag                                              20

<210> SEQ ID NO 33
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 33
attaccgcgg ctgctgg                                                 17

<210> SEQ ID NO 34
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 34
cctacgggag gcagcag                                                 17

<210> SEQ ID NO 35
<211> LENGTH: 18
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 35
ccgtcaattc mtttragt                                                18

<210> SEQ ID NO 36
<211> LENGTH: 19
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 36
caacgcgarg aaccttacc                                               19

<210> SEQ ID NO 37
<211> LENGTH: 18
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 37
acaacacgag ctgacgac                                                18

<210> SEQ ID NO 38
<211> LENGTH: 13
<212> TYPE: DNA
<213> ORGANISM: Unknown
```

```
<220> FEATURE:
<223> OTHER INFORMATION: Synthesized Bacterial Ribosomal 16S primer
      sequence

<400> SEQUENCE: 38
ggmttagata ccc                                                      13

<210> SEQ ID NO 39
<211> LENGTH: 15
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 39
crtacthchc aggyg                                                    15

<210> SEQ ID NO 40
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 40
cctacgggag gcagcag                                                  17

<210> SEQ ID NO 41
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 41
attaccgcgg ctgctgg                                                  17

<210> SEQ ID NO 42
<211> LENGTH: 30
<212> TYPE: DNA
<213> ORGANISM: Unknown
<220> FEATURE:
<223> OTHER INFORMATION: synthesized plant primer sequence

<400> SEQUENCE: 42
atgtcaccac aaacagagac taaagcaagt                                    30

<210> SEQ ID NO 43
<211> LENGTH: 21
<212> TYPE: DNA
<213> ORGANISM: Unknown
<220> FEATURE:
<223> OTHER INFORMATION: synthesized plant primer sequence

<400> SEQUENCE: 43
cttcttcagg tggaactcca g                                             21

<210> SEQ ID NO 44
<211> LENGTH: 20
<212> TYPE: DNA
<213> ORGANISM: Unknown
<220> FEATURE:
<223> OTHER INFORMATION: synthesized plant primer sequence
```

```
<400> SEQUENCE: 44
tcctccgctt attgatatgc                                           20

<210> SEQ ID NO 45
<211> LENGTH: 22
<212> TYPE: DNA
<213> ORGANISM: Unknown
<220> FEATURE:
<223> OTHER INFORMATION: synthesized plant primer sequence

<400> SEQUENCE: 45
cgatacttgg tgtgaattgc ag                                        22

<210> SEQ ID NO 46
<211> LENGTH: 20
<212> TYPE: DNA
<213> ORGANISM: Unknown
<220> FEATURE:
<223> OTHER INFORMATION: Synthesized euphausiid primer sequence

<400> SEQUENCE: 46
tttattgggg cgataaaaat                                           20

<210> SEQ ID NO 47
<211> LENGTH: 22
<212> TYPE: DNA
<213> ORGANISM: Unknown
<220> FEATURE:
<223> OTHER INFORMATION: Synthesized euphausiid primer sequence

<400> SEQUENCE: 47
tcgaggtcgy aatctttctt gt                                        22

<210> SEQ ID NO 48
<211> LENGTH: 20
<212> TYPE: DNA
<213> ORGANISM: Unknown
<220> FEATURE:
<223> OTHER INFORMATION: Synthesized mitochondrial 16s primer sequence

<400> SEQUENCE: 48
cccacatcaa ataccccta                                            20

<210> SEQ ID NO 49
<211> LENGTH: 20
<212> TYPE: DNA
<213> ORGANISM: Unknown
<220> FEATURE:
<223> OTHER INFORMATION: Synthesized mitochondrial 16s primer sequence

<400> SEQUENCE: 49
gggtcattgg tggtcagaag                                           20

<210> SEQ ID NO 50
<211> LENGTH: 21
<212> TYPE: DNA
<213> ORGANISM: Unknown
<220> FEATURE:
<223> OTHER INFORMATION: Synthesized Noto rDNA primer sequence

<400> SEQUENCE: 50
ccctatgaag cttyagacrt a                                         21

<210> SEQ ID NO 51
<211> LENGTH: 23
```

<212> TYPE: DNA
<213> ORGANISM: Unknown
<220> FEATURE:
<223> OTHER INFORMATION: Synthesized Noto rDNA primer sequence

<400> SEQUENCE: 51
ccttgttgat awggtctcta aaa                                    23

<210> SEQ ID NO 52
<211> LENGTH: 26
<212> TYPE: DNA
<213> ORGANISM: Unknown
<220> FEATURE:
<223> OTHER INFORMATION: Synthesized synthesized amphipod 18S primer
      sequence

<400> SEQUENCE: 52
ctgcggttaa aaggctcgta gttgaa                                 26

<210> SEQ ID NO 53
<211> LENGTH: 24
<212> TYPE: DNA
<213> ORGANISM: Unknown
<220> FEATURE:
<223> OTHER INFORMATION: Synthesized synthesized amphipod 18S primer
      sequence

<400> SEQUENCE: 53
actgctttra gcactctgat ttac                                   24

<210> SEQ ID NO 54
<211> LENGTH: 30
<212> TYPE: DNA
<213> ORGANISM: Unknown
<220> FEATURE:
<223> OTHER INFORMATION: Synthesized cephalopod 28S primer sequence

<400> SEQUENCE: 54
cgccgaatcc cgtcgcmagt aaamggcttc                             30

<210> SEQ ID NO 55
<211> LENGTH: 26
<212> TYPE: DNA
<213> ORGANISM: Unknown
<220> FEATURE:
<223> OTHER INFORMATION: Synthesized cephalopod 28S primer sequence

<400> SEQUENCE: 55
ccaagcaacc cgactctcgg atcgaa                                 26

<210> SEQ ID NO 56
<211> LENGTH: 15
<212> TYPE: DNA
<213> ORGANISM: Unknown
<220> FEATURE:
<223> OTHER INFORMATION: Synthesized all prey 16S primer sequence

<400> SEQUENCE: 56
gacgakaaga cccta                                             15

<210> SEQ ID NO 57
<211> LENGTH: 22
<212> TYPE: DNA
<213> ORGANISM: Unknown
<220> FEATURE:
<223> OTHER INFORMATION: Synthesized all prey 16S primer sequence

```
<400> SEQUENCE: 57
cgctgttatc cctadrgtaa ct                                    22

<210> SEQ ID NO 58
<211> LENGTH: 17
<212> TYPE: DNA
<213> ORGANISM: Unknown
<220> FEATURE:
<223> OTHER INFORMATION: Synthesized green plants primer sequence

<400> SEQUENCE: 58
gggcaatcct gagccaa                                          17

<210> SEQ ID NO 59
<211> LENGTH: 22
<212> TYPE: DNA
<213> ORGANISM: Unknown
<220> FEATURE:
<223> OTHER INFORMATION: Synthesized green plants primer sequence

<400> SEQUENCE: 59
ccattgagtc tctgcaccta tc                                    22

<210> SEQ ID NO 60
<211> LENGTH: 26
<212> TYPE: DNA
<213> ORGANISM: Unknown
<220> FEATURE:
<223> OTHER INFORMATION: Synthesized land plants primer sequence

<400> SEQUENCE: 60
atgtcaccac caacagagac taaagc                                26

<210> SEQ ID NO 61
<211> LENGTH: 21
<212> TYPE: DNA
<213> ORGANISM: Unknown
<220> FEATURE:
<223> OTHER INFORMATION: Synthesized land plants primer sequence

<400> SEQUENCE: 61
cttcttcagg tggaactcca g                                     21

<210> SEQ ID NO 62
<211> LENGTH: 22
<212> TYPE: DNA
<213> ORGANISM: Unknown
<220> FEATURE:
<223> OTHER INFORMATION: Synthesized land plants primer sequence

<400> SEQUENCE: 62
gttatgcatg aacgtaatgc tc                                    22

<210> SEQ ID NO 63
<211> LENGTH: 21
<212> TYPE: DNA
<213> ORGANISM: Unknown
<220> FEATURE:
<223> OTHER INFORMATION: Synthesized land plants primer sequence

<400> SEQUENCE: 63
cgcgcatggt ggattcacaa t                                     21

<210> SEQ ID NO 64
<211> LENGTH: 18
```

```
<212> TYPE: DNA
<213> ORGANISM: Unknown
<220> FEATURE:
<223> OTHER INFORMATION: Synthesized vertebrates 12s primer sequence

<400> SEQUENCE: 64
tagaacaggc tcctctag                                                 18

<210> SEQ ID NO 65
<211> LENGTH: 18
<212> TYPE: DNA
<213> ORGANISM: Unknown
<220> FEATURE:
<223> OTHER INFORMATION: Synthesized vertebrates 12s primer sequence

<400> SEQUENCE: 65
ttagataccc cactatgc                                                 18

<210> SEQ ID NO 66
<211> LENGTH: 20
<212> TYPE: DNA
<213> ORGANISM: Unknown
<220> FEATURE:
<223> OTHER INFORMATION: Synthesized chordata 16s primer sequence

<400> SEQUENCE: 66
cgagaagacc ctrtggagct                                               20

<210> SEQ ID NO 67
<211> LENGTH: 19
<212> TYPE: DNA
<213> ORGANISM: Unknown
<220> FEATURE:
<223> OTHER INFORMATION: Synthesized chordata 16s primer sequence

<400> SEQUENCE: 67
ggattgcgct gttatccct                                                19

<210> SEQ ID NO 68
<211> LENGTH: 20
<212> TYPE: DNA
<213> ORGANISM: Unknown
<220> FEATURE:
<223> OTHER INFORMATION: Synthesized chordata 16s primer sequence

<400> SEQUENCE: 68
cgagaagacc ctrtggagct                                               20

<210> SEQ ID NO 69
<211> LENGTH: 16
<212> TYPE: DNA
<213> ORGANISM: Unknown
<220> FEATURE:
<223> OTHER INFORMATION: Synthesized chordata 16s primer sequence
<220> FEATURE:
<221> NAME/KEY: misc_feature
<222> LOCATION: (4)..(4)
<223> OTHER INFORMATION: n is a, c, g, or t

<400> SEQUENCE: 69
cctnggtcgc cccaac                                                   16

<210> SEQ ID NO 70
<211> LENGTH: 30
<212> TYPE: DNA
<213> ORGANISM: Unknown
<220> FEATURE:
```

<223> OTHER INFORMATION: Synthesized insecta COI primer sequence

<400> SEQUENCE: 70
agatattgga acwttatatt ttattttttgg                                    30

<210> SEQ ID NO 71
<211> LENGTH: 24
<212> TYPE: DNA
<213> ORGANISM: Unknown
<220> FEATURE:
<223> OTHER INFORMATION: Synthesized insecta COI primer sequence

<400> SEQUENCE: 71
wactaatcaa ttwccaaatc ctcc                                           24

<210> SEQ ID NO 72
<211> LENGTH: 21
<212> TYPE: DNA
<213> ORGANISM: Unknown
<220> FEATURE:
<223> OTHER INFORMATION: Synthesized lumbricidae 12S primer sequence

<400> SEQUENCE: 72
tgtgtactgc cgtcgtaagc a                                              21

<210> SEQ ID NO 73
<211> LENGTH: 20
<212> TYPE: DNA
<213> ORGANISM: Unknown
<220> FEATURE:
<223> OTHER INFORMATION: Synthesized lumbricidae 12S primer sequence

<400> SEQUENCE: 73
aagagcgacg ggcgatgtgt                                                20

<210> SEQ ID NO 74
<211> LENGTH: 22
<212> TYPE: DNA
<213> ORGANISM: Unknown
<220> FEATURE:
<223> OTHER INFORMATION: Synthesized 16S primer sequence

<400> SEQUENCE: 74
ccggtctgaa ctcagatcac gt                                             22

<210> SEQ ID NO 75
<211> LENGTH: 20
<212> TYPE: DNA
<213> ORGANISM: Unknown
<220> FEATURE:
<223> OTHER INFORMATION: Synthesized 16S primer sequence

<400> SEQUENCE: 75
cgcctgttta tcaaaaacat                                                20

<210> SEQ ID NO 76
<211> LENGTH: 20
<212> TYPE: DNA
<213> ORGANISM: Unknown
<220> FEATURE:
<223> OTHER INFORMATION: Synthesized papillomavirus primer sequence

<400> SEQUENCE: 76
cgtccmarrg gawactgatc                                                20

<210> SEQ ID NO 77
<211> LENGTH: 20
<212> TYPE: DNA
<213> ORGANISM: Unknown
<220> FEATURE:
<223> OTHER INFORMATION: Synthesized papillomavirus primer sequence

<400> SEQUENCE: 77
gcmcagggwc ataayaatgg                                           20

<210> SEQ ID NO 78
<211> LENGTH: 27
<212> TYPE: DNA
<213> ORGANISM: Unknown
<220> FEATURE:
<223> OTHER INFORMATION: Synthesized coronavirus primer sequence

<400> SEQUENCE: 78
gggawgggat tacmcaaart gygaymg                                   27

<210> SEQ ID NO 79
<211> LENGTH: 24
<212> TYPE: DNA
<213> ORGANISM: Unknown
<220> FEATURE:
<223> OTHER INFORMATION: Synthesized coronavirus primer sequence
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 79
cccasaagwt gtaccnccng gytt                                      24

<210> SEQ ID NO 80
<211> LENGTH: 24
<212> TYPE: DNA
<213> ORGANISM: Unknown
<220> FEATURE:
<223> OTHER INFORMATION: Synthesized Epstein Barr virus primer sequence

<400> SEQUENCE: 80 gktagactttt gccagcytst accc                                     24

<210> SEQ ID NO 81
<211> LENGTH: 24
<212> TYPE: DNA
<213> ORGANISM: Unknown
<220> FEATURE:
<223> OTHER INFORMATION: Synthesized Epstein Barr virus primer sequence

<400> SEQUENCE: 81
gggagtcmgt gtcsccgtak atga                                      24

<210> SEQ ID NO 82
<211> LENGTH: 36
<212> TYPE: DNA
<213> ORGANISM: Unknown
<220> FEATURE:
<223> OTHER INFORMATION: Synthesized papillomavirus primer sequence
<220> FEATURE:
<221> NAME/KEY: misc_feature
<222> LOCATION: (30)..(30)
<223> OTHER INFORMATION: n is a, c, g, or t

```
<400> SEQUENCE: 82
gagcttataa acacagttat tgaggayggn gayatg                                36

<210> SEQ ID NO 83
<211> LENGTH: 32
<212> TYPE: DNA
<213> ORGANISM: Unknown
<220> FEATURE:
<223> OTHER INFORMATION: Synthesized papillomavirus primer sequence
<220> FEATURE:
<221> NAME/KEY: misc_feature
<222> LOCATION: (24)..(24)
<223> OTHER INFORMATION: n is a, c, g, or t

<400> SEQUENCE: 83
aacagttgat tgtcccagca gaynacrttr tt                                    32

<210> SEQ ID NO 84
<211> LENGTH: 15
<212> TYPE: DNA
<213> ORGANISM: Unknown
<220> FEATURE:
<223> OTHER INFORMATION: Synthesized enterovirus primer sequence

<400> SEQUENCE: 84
tccggcccct gaatg                                                       15

<210> SEQ ID NO 85
<211> LENGTH: 18
<212> TYPE: DNA
<213> ORGANISM: Unknown
<220> FEATURE:
<223> OTHER INFORMATION: Synthesized enterovirus primer sequence

<400> SEQUENCE: 85
caccggatgg ccaatcca                                                    18

<210> SEQ ID NO 86
<211> LENGTH: 20
<212> TYPE: DNA
<213> ORGANISM: Unknown
<220> FEATURE:
<223> OTHER INFORMATION: Synthesized influenza A primer sequence

<400> SEQUENCE: 86
cagattgctg actcccagca                                                  20

<210> SEQ ID NO 87
<211> LENGTH: 23
<212> TYPE: DNA
<213> ORGANISM: Unknown
<220> FEATURE:
<223> OTHER INFORMATION: Synthesized influenza A primer sequence

<400> SEQUENCE: 87
gaccagcact ggagctagga tga                                              23

<210> SEQ ID NO 88
<211> LENGTH: 25
<212> TYPE: DNA
<213> ORGANISM: Unknown
<220> FEATURE:
<223> OTHER INFORMATION: Synthesized adenovirus primer sequence

<400> SEQUENCE: 88
gccgcagtgg tcttacatgc acatc                                            25
```

<210> SEQ ID NO 89
<211> LENGTH: 23
<212> TYPE: DNA
<213> ORGANISM: Unknown
<220> FEATURE:
<223> OTHER INFORMATION: Synthesized adenovirus primer sequence

<400> SEQUENCE: 89
cagcacgccg cggatgtcaa agt                                          23

<210> SEQ ID NO 90
<211> LENGTH: 20
<212> TYPE: DNA
<213> ORGANISM: Unknown
<220> FEATURE:
<223> OTHER INFORMATION: Synthesized cytomegalovirus primer sequence

<400> SEQUENCE: 90
gttctctcgt ctcctccgtg                                              20

<210> SEQ ID NO 91
<211> LENGTH: 20
<212> TYPE: DNA
<213> ORGANISM: Unknown
<220> FEATURE:
<223> OTHER INFORMATION: Synthesized cytomegalovirus primer sequence

<400> SEQUENCE: 91
cctgtggagc tcgttagagg                                              20

<210> SEQ ID NO 92
<211> LENGTH: 18
<212> TYPE: DNA
<213> ORGANISM: Unknown
<220> FEATURE:
<223> OTHER INFORMATION: Synthesized EBV primer sequence

<400> SEQUENCE: 92
gagggtggtt tggaaagc                                                18

<210> SEQ ID NO 93
<211> LENGTH: 22
<212> TYPE: DNA
<213> ORGANISM: Unknown
<220> FEATURE:
<223> OTHER INFORMATION: Synthesized EBV primer sequence

<400> SEQUENCE: 93
aacagacaat ggactcccctt ag                                          22

<210> SEQ ID NO 94
<211> LENGTH: 20
<212> TYPE: DNA
<213> ORGANISM: Unknown
<220> FEATURE:
<223> OTHER INFORMATION: Synthesized Parovirus B19 primer sequence

<400> SEQUENCE: 94
gatactcaac cccatggaga                                              20

<210> SEQ ID NO 95
<211> LENGTH: 22
<212> TYPE: DNA
<213> ORGANISM: Unknown
<220> FEATURE:

```
<223> OTHER INFORMATION: Synthesized Parovirus B19 primer sequence

<400> SEQUENCE: 95
gccctaacac atatgggtac tt                                              22

<210> SEQ ID NO 96
<211> LENGTH: 23
<212> TYPE: DNA
<213> ORGANISM: Unknown
<220> FEATURE:
<223> OTHER INFORMATION: Synthesized human herpes primer sequence

<400> SEQUENCE: 96
taagatgtat gctgaagaac gtg                                             23

<210> SEQ ID NO 97
<211> LENGTH: 19
<212> TYPE: DNA
<213> ORGANISM: Unknown
<220> FEATURE:
<223> OTHER INFORMATION: Synthesized human herpes primer sequence

<400> SEQUENCE: 97
gcttgtcttc gtcgtttcg                                                  19

<210> SEQ ID NO 98
<211> LENGTH: 21
<212> TYPE: DNA
<213> ORGANISM: Unknown
<220> FEATURE:
<223> OTHER INFORMATION: Synthesized influenza A primer sequence

<400> SEQUENCE: 98
cttctaaccg aggtcgaaac g                                               21

<210> SEQ ID NO 99
<211> LENGTH: 25
<212> TYPE: DNA
<213> ORGANISM: Unknown
<220> FEATURE:
<223> OTHER INFORMATION: Synthesized influenza A primer sequence

<400> SEQUENCE: 99
agggcatttt ggacaaagtc gtcta                                           25

<210> SEQ ID NO 100
<211> LENGTH: 21
<212> TYPE: DNA
<213> ORGANISM: Unknown
<220> FEATURE:
<223> OTHER INFORMATION: Synthesized ABCCB-related hyperinsulinism
      primer sequence

<400> SEQUENCE: 100
cagctgagcc cgagcccaga c                                               21

<210> SEQ ID NO 101
<211> LENGTH: 23
<212> TYPE: DNA
<213> ORGANISM: Unknown
<220> FEATURE:
<223> OTHER INFORMATION: Synthesized ABCCB-related hyperinsulinism
      primer sequence

<400> SEQUENCE: 101
tcctccctcc ctgctctccc gtc                                             23
```

<210> SEQ ID NO 102
<211> LENGTH: 26
<212> TYPE: DNA
<213> ORGANISM: Unknown
<220> FEATURE:
<223> OTHER INFORMATION: Synthesized Alkaptonuria primer sequence

<400> SEQUENCE: 102
gggaattctg taaccggtta aataag                                    26

<210> SEQ ID NO 103
<211> LENGTH: 25
<212> TYPE: DNA
<213> ORGANISM: Unknown
<220> FEATURE:
<223> OTHER INFORMATION: Synthesized Alkaptonuria primer sequence

<400> SEQUENCE: 103
cttgctttaa ctcagccatt ttctc                                     25

<210> SEQ ID NO 104
<211> LENGTH: 22
<212> TYPE: DNA
<213> ORGANISM: Unknown
<220> FEATURE:
<223> OTHER INFORMATION: Synthesized Alpha-1 antitrypsin primer sequence

<400> SEQUENCE: 104
caccgtgaag gtgcctatga tg                                        22

<210> SEQ ID NO 105
<211> LENGTH: 22
<212> TYPE: DNA
<213> ORGANISM: Unknown
<220> FEATURE:
<223> OTHER INFORMATION: Synthesized Alpha-1 antitrypsin primer sequence

<400> SEQUENCE: 105
ggcattgccc aggtatttca tc                                        22

<210> SEQ ID NO 106
<211> LENGTH: 21
<212> TYPE: DNA
<213> ORGANISM: Unknown
<220> FEATURE:
<223> OTHER INFORMATION: Synthesized alpha-mannosidosis primer sequence

<400> SEQUENCE: 106
acgccagtgt cacctttagc c                                         21

<210> SEQ ID NO 107
<211> LENGTH: 20
<212> TYPE: DNA
<213> ORGANISM: Unknown
<220> FEATURE:
<223> OTHER INFORMATION: Synthesized alpha-mannosidosis primer sequence

<400> SEQUENCE: 107
gcacagccag acctcgcaat                                           20

<210> SEQ ID NO 108
<211> LENGTH: 20
<212> TYPE: DNA
<213> ORGANISM: Unknown
<220> FEATURE:

<223> OTHER INFORMATION: Synthesized SLC12A6 primer sequence

<400> SEQUENCE: 108
tgaatcaaga aacccagact                                          20

<210> SEQ ID NO 109
<211> LENGTH: 21
<212> TYPE: DNA
<213> ORGANISM: Unknown
<220> FEATURE:
<223> OTHER INFORMATION: Synthesized SLC12A6 primer sequence

<400> SEQUENCE: 109
attccatgtt ttcaccacta c                                        21

<210> SEQ ID NO 110
<211> LENGTH: 22
<212> TYPE: DNA
<213> ORGANISM: Unknown
<220> FEATURE:
<223> OTHER INFORMATION: Synthesized ARS1 primer sequence

<400> SEQUENCE: 110
cttttcccac gtggtggagt ag                                       22

<210> SEQ ID NO 111
<211> LENGTH: 21
<212> TYPE: DNA
<213> ORGANISM: Unknown
<220> FEATURE:
<223> OTHER INFORMATION: Synthesized ARS1 primer sequence

<400> SEQUENCE: 111
cccgcacaac aggtaaaaga c                                        21

<210> SEQ ID NO 112
<211> LENGTH: 18
<212> TYPE: DNA
<213> ORGANISM: Homo sapiens

<400> SEQUENCE: 112
ctgaaggccg aggccaag                                            18

<210> SEQ ID NO 113
<211> LENGTH: 19
<212> TYPE: DNA
<213> ORGANISM: Homo sapiens

<400> SEQUENCE: 113
cctcacggga cacaagcag                                           19

<210> SEQ ID NO 114
<211> LENGTH: 22
<212> TYPE: DNA
<213> ORGANISM: Homo sapiens

<400> SEQUENCE: 114
ggtagctgcg tggctaacgg ag                                       22

<210> SEQ ID NO 115
<211> LENGTH: 25
<212> TYPE: DNA
<213> ORGANISM: Homo sapiens

<400> SEQUENCE: 115

```
ccacatacat tatcatccac tgtag                                          25

<210> SEQ ID NO 116
<211> LENGTH: 25
<212> TYPE: DNA
<213> ORGANISM: Homo sapiens

<400> SEQUENCE: 116
gaaaggatca tttctccctt gagtc                                          25

<210> SEQ ID NO 117
<211> LENGTH: 25
<212> TYPE: DNA
<213> ORGANISM: Homo sapiens

<400> SEQUENCE: 117
caggaacttg actccatagg gaaag                                          25

<210> SEQ ID NO 118
<211> LENGTH: 20
<212> TYPE: DNA
<213> ORGANISM: Homo sapiens

<400> SEQUENCE: 118
cctgtcttgc tttcctctcc                                                20

<210> SEQ ID NO 119
<211> LENGTH: 20
<212> TYPE: DNA
<213> ORGANISM: Homo sapiens

<400> SEQUENCE: 119
tcctcctctt tccccagaag                                                20

<210> SEQ ID NO 120
<211> LENGTH: 22
<212> TYPE: DNA
<213> ORGANISM: Homo sapiens

<400> SEQUENCE: 120
gccccattac attccagatt tg                                             22

<210> SEQ ID NO 121
<211> LENGTH: 20
<212> TYPE: DNA
<213> ORGANISM: Homo sapiens

<400> SEQUENCE: 121
ctcatacacg gcagccacat                                                20

<210> SEQ ID NO 122
<211> LENGTH: 24
<212> TYPE: DNA
<213> ORGANISM: Homo sapiens

<400> SEQUENCE: 122
ctttcttttc gtaatatgcg gcct                                           24

<210> SEQ ID NO 123
<211> LENGTH: 25
<212> TYPE: DNA
<213> ORGANISM: Homo sapiens
```

```
<400> SEQUENCE: 123
tcctgagagg atcaagactg gaaac                                          25

<210> SEQ ID NO 124
<211> LENGTH: 20
<212> TYPE: DNA
<213> ORGANISM: Homo sapiens

<400> SEQUENCE: 124
gccacaatgc ctctgaaagc                                                20

<210> SEQ ID NO 125
<211> LENGTH: 21
<212> TYPE: DNA
<213> ORGANISM: Homo sapiens

<400> SEQUENCE: 125
cttcatagca aggccaagaa c                                              21

<210> SEQ ID NO 126
<211> LENGTH: 21
<212> TYPE: DNA
<213> ORGANISM: Homo sapiens

<400> SEQUENCE: 126
cttcaaccct ccaggctaaa t                                              21

<210> SEQ ID NO 127
<211> LENGTH: 21
<212> TYPE: DNA
<213> ORGANISM: Homo sapiens

<400> SEQUENCE: 127
caaaactcgc cactgacaga a                                              21

<210> SEQ ID NO 128
<211> LENGTH: 19
<212> TYPE: DNA
<213> ORGANISM: Homo sapiens

<400> SEQUENCE: 128
tggcactggc tgtctcagg                                                 19

<210> SEQ ID NO 129
<211> LENGTH: 20
<212> TYPE: DNA
<213> ORGANISM: Homo sapiens

<400> SEQUENCE: 129
gacaggacag gttgcaggac                                                20

<210> SEQ ID NO 130
<211> LENGTH: 22
<212> TYPE: DNA
<213> ORGANISM: Homo sapiens

<400> SEQUENCE: 130
cattctgtca cccttagaag cc                                             22

<210> SEQ ID NO 131
<211> LENGTH: 22
<212> TYPE: DNA
<213> ORGANISM: Homo sapiens
```

```
<400> SEQUENCE: 131
ggctatcaga gtccagattc cg                                          22

<210> SEQ ID NO 132
<211> LENGTH: 20
<212> TYPE: DNA
<213> ORGANISM: Homo sapiens

<400> SEQUENCE: 132
cgtacatacg tactgacgca                                             20

<210> SEQ ID NO 133
<211> LENGTH: 19
<212> TYPE: DNA
<213> ORGANISM: Homo sapiens

<400> SEQUENCE: 133
taagcaacca cctgacagg                                              19

<210> SEQ ID NO 134
<211> LENGTH: 25
<212> TYPE: DNA
<213> ORGANISM: Homo sapiens

<400> SEQUENCE: 134
gcatagcaga gtacctgaaa cagga                                       25

<210> SEQ ID NO 135
<211> LENGTH: 26
<212> TYPE: DNA
<213> ORGANISM: Homo sapiens

<400> SEQUENCE: 135
gacgtttgtc tcactaatga gtgaac                                      26

<210> SEQ ID NO 136
<211> LENGTH: 20
<212> TYPE: DNA
<213> ORGANISM: Homo sapiens

<400> SEQUENCE: 136
cagattgtct acagggagct                                             20

<210> SEQ ID NO 137
<211> LENGTH: 20
<212> TYPE: DNA
<213> ORGANISM: Homo sapiens

<400> SEQUENCE: 137
cttggcaaca aacagatcag                                             20

<210> SEQ ID NO 138
<211> LENGTH: 20
<212> TYPE: DNA
<213> ORGANISM: Homo sapiens

<400> SEQUENCE: 138
actacatttc ccaggattcc                                             20

<210> SEQ ID NO 139
<211> LENGTH: 20
<212> TYPE: DNA
```

```
<213> ORGANISM: Homo sapiens

<400> SEQUENCE: 139
tgcaggaaga gtaacaatcg                                              20

<210> SEQ ID NO 140
<211> LENGTH: 25
<212> TYPE: DNA
<213> ORGANISM: Homo sapiens

<400> SEQUENCE: 140
atgcctagac tcctgactac aacac                                        25

<210> SEQ ID NO 141
<211> LENGTH: 25
<212> TYPE: DNA
<213> ORGANISM: Homo sapiens

<400> SEQUENCE: 141
ctttgagtgg cagtgagaaa ataat                                        25

<210> SEQ ID NO 142
<211> LENGTH: 25
<212> TYPE: DNA
<213> ORGANISM: Homo sapiens

<400> SEQUENCE: 142
ctctcaaggt atatttctga catac                                        25

<210> SEQ ID NO 143
<211> LENGTH: 21
<212> TYPE: DNA
<213> ORGANISM: Homo sapiens

<400> SEQUENCE: 143
caaggcgtat ttgcttgaga g                                            21

<210> SEQ ID NO 144
<211> LENGTH: 19
<212> TYPE: DNA
<213> ORGANISM: Homo sapiens

<400> SEQUENCE: 144
gccagtgttt ttgcctgag                                               19

<210> SEQ ID NO 145
<211> LENGTH: 20
<212> TYPE: DNA
<213> ORGANISM: Homo sapiens

<400> SEQUENCE: 145
gactgctctc atagcatcgc                                              20

<210> SEQ ID NO 146
<211> LENGTH: 20
<212> TYPE: DNA
<213> ORGANISM: Homo sapiens

<400> SEQUENCE: 146
agttggcacc agctaaagat                                              20

<210> SEQ ID NO 147
<211> LENGTH: 20
```

```
<212> TYPE: DNA
<213> ORGANISM: Homo sapiens

<400> SEQUENCE: 147
tgtgaaccac agcagaatct                                              20

<210> SEQ ID NO 148
<211> LENGTH: 22
<212> TYPE: DNA
<213> ORGANISM: Homo sapiens

<400> SEQUENCE: 148
gtgaaggcac tgataaaaga gc                                           22

<210> SEQ ID NO 149
<211> LENGTH: 23
<212> TYPE: DNA
<213> ORGANISM: Homo sapiens

<400> SEQUENCE: 149
tggtagagtc cctgaagtca gaa                                          23

<210> SEQ ID NO 150
<211> LENGTH: 28
<212> TYPE: DNA
<213> ORGANISM: Homo sapiens

<400> SEQUENCE: 150
tcaggcgctc agctccgttt cggtttca                                     28

<210> SEQ ID NO 151
<211> LENGTH: 26
<212> TYPE: DNA
<213> ORGANISM: Homo sapiens

<400> SEQUENCE: 151
aagcgccatt ggagccccgc acttcc                                       26

<210> SEQ ID NO 152
<211> LENGTH: 20
<212> TYPE: DNA
<213> ORGANISM: Homo sapiens

<400> SEQUENCE: 152
agaggctggg gccaactgga                                              20

<210> SEQ ID NO 153
<211> LENGTH: 27
<212> TYPE: DNA
<213> ORGANISM: Homo sapiens

<400> SEQUENCE: 153
catactgcat gtgagagtct ggagacg                                      27

<210> SEQ ID NO 154
<211> LENGTH: 23
<212> TYPE: DNA
<213> ORGANISM: Homo sapiens

<400> SEQUENCE: 154
acccaggagc ccaagttccc ttt                                          23

<210> SEQ ID NO 155
```

```
<211> LENGTH: 20
<212> TYPE: DNA
<213> ORGANISM: Homo sapiens

<400> SEQUENCE: 155
acagatcagc atggctaaat                                              20

<210> SEQ ID NO 156
<211> LENGTH: 20
<212> TYPE: DNA
<213> ORGANISM: Homo sapiens

<400> SEQUENCE: 156
ttggtgtttg ctcaggaaga                                              20

<210> SEQ ID NO 157
<211> LENGTH: 20
<212> TYPE: DNA
<213> ORGANISM: Homo sapiens

<400> SEQUENCE: 157
ggcctacagg ggtttcaaat                                              20

<210> SEQ ID NO 158
<211> LENGTH: 18
<212> TYPE: DNA
<213> ORGANISM: Homo sapiens

<400> SEQUENCE: 158
caatagggcc ggcttgac                                                18

<210> SEQ ID NO 159
<211> LENGTH: 22
<212> TYPE: DNA
<213> ORGANISM: Homo sapiens

<400> SEQUENCE: 159
tgcaacaatt agttggaaaa gc                                           22

<210> SEQ ID NO 160
<211> LENGTH: 20
<212> TYPE: DNA
<213> ORGANISM: Homo sapiens

<400> SEQUENCE: 160
agtgtggggt cgggagtgtg                                              20

<210> SEQ ID NO 161
<211> LENGTH: 20
<212> TYPE: DNA
<213> ORGANISM: Homo sapiens

<400> SEQUENCE: 161
cgggcagctc tcggattctg                                              20

<210> SEQ ID NO 162
<211> LENGTH: 20
<212> TYPE: DNA
<213> ORGANISM: Homo sapiens

<400> SEQUENCE: 162
ccaaacccac ctctagcaaa                                              20
```

-continued

```
<210> SEQ ID NO 163
<211> LENGTH: 18
<212> TYPE: DNA
<213> ORGANISM: Homo sapiens

<400> SEQUENCE: 163
agagctgagg cggaatgg                                                 18

<210> SEQ ID NO 164
<211> LENGTH: 21
<212> TYPE: DNA
<213> ORGANISM: Homo sapiens

<400> SEQUENCE: 164
ctatgcctgg ttgcttagct g                                             21

<210> SEQ ID NO 165
<211> LENGTH: 22
<212> TYPE: DNA
<213> ORGANISM: Homo sapiens

<400> SEQUENCE: 165
cttcgttcta cccgaatcca tt                                            22

<210> SEQ ID NO 166
<211> LENGTH: 18
<212> TYPE: DNA
<213> ORGANISM: Homo sapiens

<400> SEQUENCE: 166
ctcaagcaca gtggattg                                                 18

<210> SEQ ID NO 167
<211> LENGTH: 19
<212> TYPE: DNA
<213> ORGANISM: Homo sapiens

<400> SEQUENCE: 167
gctctgaaga aaactctag                                                19

<210> SEQ ID NO 168
<211> LENGTH: 20
<212> TYPE: DNA
<213> ORGANISM: Homo sapiens

<400> SEQUENCE: 168
acggctgtca tcacttagac                                               20

<210> SEQ ID NO 169
<211> LENGTH: 20
<212> TYPE: DNA
<213> ORGANISM: Homo sapiens

<400> SEQUENCE: 169
ctccccttcc tatgacatga                                               20

<210> SEQ ID NO 170
<211> LENGTH: 21
<212> TYPE: DNA
<213> ORGANISM: Homo sapiens

<400> SEQUENCE: 170
aagcactgca gtaccttgga a                                             21
```

<210> SEQ ID NO 171
<211> LENGTH: 24
<212> TYPE: DNA
<213> ORGANISM: Homo sapiens

<400> SEQUENCE: 171
tcatgtagca tttaccacag ttga                                               24

<210> SEQ ID NO 172
<211> LENGTH: 10
<212> TYPE: DNA
<213> ORGANISM: Homo sapiens

<400> SEQUENCE: 172
tgcaagcgag                                                               10

<210> SEQ ID NO 173
<211> LENGTH: 11
<212> TYPE: DNA
<213> ORGANISM: Homo sapiens

<400> SEQUENCE: 173
caagccttta t                                                             11

<210> SEQ ID NO 174
<211> LENGTH: 22
<212> TYPE: DNA
<213> ORGANISM: Homo sapiens

<400> SEQUENCE: 174
acctttgcag ggaatacagg gc                                                 22

<210> SEQ ID NO 175
<211> LENGTH: 24
<212> TYPE: DNA
<213> ORGANISM: Homo sapiens

<400> SEQUENCE: 175
tgtcttcctc tctctaaggg gttc                                               24

<210> SEQ ID NO 176
<211> LENGTH: 20
<212> TYPE: DNA
<213> ORGANISM: Homo sapiens

<400> SEQUENCE: 176
cggagattta acggggacgt                                                    20

<210> SEQ ID NO 177
<211> LENGTH: 20
<212> TYPE: DNA
<213> ORGANISM: Homo sapiens

<400> SEQUENCE: 177 tcgattttc caccccgcc                                                      20

<210> SEQ ID NO 178
<211> LENGTH: 20
<212> TYPE: DNA
<213> ORGANISM: Homo sapiens

<400> SEQUENCE: 178
cctaggtttg tgatgcctct                                                    20

```
<210> SEQ ID NO 179
<211> LENGTH: 20
<212> TYPE: DNA
<213> ORGANISM: Homo sapiens

<400> SEQUENCE: 179
taggttcaac tctctcctga                                               20

<210> SEQ ID NO 180
<211> LENGTH: 20
<212> TYPE: DNA
<213> ORGANISM: Homo sapiens

<400> SEQUENCE: 180
ccaggcaggg acccaagaat                                               20

<210> SEQ ID NO 181
<211> LENGTH: 20
<212> TYPE: DNA
<213> ORGANISM: Homo sapiens

<400> SEQUENCE: 181
ccactccgca ctgtccctct                                               20

<210> SEQ ID NO 182
<211> LENGTH: 16
<212> TYPE: DNA
<213> ORGANISM: Homo sapiens

<400> SEQUENCE: 182
acccaacccc tcccac                                                   16

<210> SEQ ID NO 183
<211> LENGTH: 17
<212> TYPE: DNA
<213> ORGANISM: Homo sapiens

<400> SEQUENCE: 183
agcttcagag accggag                                                  17

<210> SEQ ID NO 184
<211> LENGTH: 20
<212> TYPE: DNA
<213> ORGANISM: Homo sapiens

<400> SEQUENCE: 184
caaagaggtg ccctatggtg                                               20

<210> SEQ ID NO 185
<211> LENGTH: 19
<212> TYPE: DNA
<213> ORGANISM: Homo sapiens

<400> SEQUENCE: 185
caatcacgcg agctctctc                                                19

<210> SEQ ID NO 186
<211> LENGTH: 20
<212> TYPE: DNA
<213> ORGANISM: Homo sapiens

<400> SEQUENCE: 186
```

-continued caccgttatc ccttaggtct                                            20

<210> SEQ ID NO 187
<211> LENGTH: 19
<212> TYPE: DNA
<213> ORGANISM: Homo sapiens

<400> SEQUENCE: 187
taggtcaagc tctgggaca                                             19

<210> SEQ ID NO 188
<211> LENGTH: 21
<212> TYPE: DNA
<213> ORGANISM: Homo sapiens

<400> SEQUENCE: 188
cctatatgga aaacaatgtg g                                          21

<210> SEQ ID NO 189
<211> LENGTH: 20
<212> TYPE: DNA
<213> ORGANISM: Homo sapiens

<400> SEQUENCE: 189
aaggagctaa catttcaggc                                            20

<210> SEQ ID NO 190
<211> LENGTH: 21
<212> TYPE: DNA
<213> ORGANISM: Homo sapiens

<400> SEQUENCE: 190
gcgcttctct cggctcctta g                                          21

<210> SEQ ID NO 191
<211> LENGTH: 19
<212> TYPE: DNA
<213> ORGANISM: Homo sapiens

<400> SEQUENCE: 191
ggctgcgctg ggtgtagtg                                             19

<210> SEQ ID NO 192
<211> LENGTH: 20
<212> TYPE: DNA
<213> ORGANISM: Homo sapiens

<400> SEQUENCE: 192 cttccctgc aatttcattt                                             20

<210> SEQ ID NO 193
<211> LENGTH: 20
<212> TYPE: DNA
<213> ORGANISM: Homo sapiens

<400> SEQUENCE: 193
ccagggacct tcctagacaa                                            20

<210> SEQ ID NO 194
<211> LENGTH: 20
<212> TYPE: DNA
<213> ORGANISM: Homo sapiens

<400> SEQUENCE: 194
ccatgaccca ggagccattc                                              20

<210> SEQ ID NO 195
<211> LENGTH: 25
<212> TYPE: DNA
<213> ORGANISM: Homo sapiens

<400> SEQUENCE: 195
cgattacctc gacgactgag taaga                                        25

<210> SEQ ID NO 196
<211> LENGTH: 29
<212> TYPE: DNA
<213> ORGANISM: Homo sapiens

<400> SEQUENCE: 196
ggtacgtggg gctgcttgaa gagacgctg                                    29

<210> SEQ ID NO 197
<211> LENGTH: 32
<212> TYPE: DNA
<213> ORGANISM: Homo sapiens

<400> SEQUENCE: 197
gaagatctgg gtaggcagca ggtccaggga gc                                32

<210> SEQ ID NO 198
<211> LENGTH: 18
<212> TYPE: DNA
<213> ORGANISM: Homo sapiens

<400> SEQUENCE: 198
ccgaagcagg gagctttg                                                18

<210> SEQ ID NO 199
<211> LENGTH: 18
<212> TYPE: DNA
<213> ORGANISM: Homo sapiens

<400> SEQUENCE: 199
cggtgcatgc cttcacaa                                                18

<210> SEQ ID NO 200
<211> LENGTH: 18
<212> TYPE: DNA
<213> ORGANISM: Homo sapiens

<400> SEQUENCE: 200
ctacgcctgc ccgcactg                                                18

<210> SEQ ID NO 201
<211> LENGTH: 19
<212> TYPE: DNA
<213> ORGANISM: Homo sapiens

<400> SEQUENCE: 201
ccaaggacca caggggaca                                               19

<210> SEQ ID NO 202
<211> LENGTH: 21
<212> TYPE: DNA
<213> ORGANISM: Homo sapiens

<400> SEQUENCE: 202
cattcacctc tgtgggtaag c                                    21

<210> SEQ ID NO 203
<211> LENGTH: 20
<212> TYPE: DNA
<213> ORGANISM: Homo sapiens

<400> SEQUENCE: 203
aggccttcac atttcacagc                                      20

<210> SEQ ID NO 204
<211> LENGTH: 20
<212> TYPE: DNA
<213> ORGANISM: Homo sapiens

<400> SEQUENCE: 204
agcattcctg atgccatgga                                      20

<210> SEQ ID NO 205
<211> LENGTH: 19
<212> TYPE: DNA
<213> ORGANISM: Homo sapiens

<400> SEQUENCE: 205
cttgcgaaag ccttccttg                                       19

<210> SEQ ID NO 206
<211> LENGTH: 25
<212> TYPE: DNA
<213> ORGANISM: Homo sapiens

<400> SEQUENCE: 206
ggctgtgtca ttttcttctc gctgg                                25

<210> SEQ ID NO 207
<211> LENGTH: 23
<212> TYPE: DNA
<213> ORGANISM: Homo sapiens

<400> SEQUENCE: 207
tccaccaaac gtacccagac aag                                  23

<210> SEQ ID NO 208
<211> LENGTH: 24
<212> TYPE: DNA
<213> ORGANISM: Homo sapiens

<400> SEQUENCE: 208
tgtgtatgtg tctatcaact tatc                                 24

<210> SEQ ID NO 209
<211> LENGTH: 21
<212> TYPE: DNA
<213> ORGANISM: Homo sapiens

<400> SEQUENCE: 209
caaccccctt actggaaact a                                    21

<210> SEQ ID NO 210
<211> LENGTH: 34
<212> TYPE: DNA
<213> ORGANISM: Homo sapiens

```
<400> SEQUENCE: 210
catgtgaagc ttatgaatcc tgcgagcgat gggg                         34

<210> SEQ ID NO 211
<211> LENGTH: 32
<212> TYPE: DNA
<213> ORGANISM: Homo sapiens

<400> SEQUENCE: 211
accatggaat tcctatggcc tcttttccgc ag                           32

<210> SEQ ID NO 212
<211> LENGTH: 16
<212> TYPE: DNA
<213> ORGANISM: Homo sapiens

<400> SEQUENCE: 212
cccctgcgtg gcagcc                                             16

<210> SEQ ID NO 213
<211> LENGTH: 22
<212> TYPE: DNA
<213> ORGANISM: Homo sapiens

<400> SEQUENCE: 213
gtctttccca accgatccta tc                                      22

<210> SEQ ID NO 214
<211> LENGTH: 26
<212> TYPE: DNA
<213> ORGANISM: Homo sapiens

<400> SEQUENCE: 214
cgtgcgaaga tttgatgaac gaggtg                                  26

<210> SEQ ID NO 215
<211> LENGTH: 24
<212> TYPE: DNA
<213> ORGANISM: Homo sapiens

<400> SEQUENCE: 215
gcccttctgg gtagtctctg gatc                                    24

<210> SEQ ID NO 216
<211> LENGTH: 19
<212> TYPE: DNA
<213> ORGANISM: Homo sapiens

<400> SEQUENCE: 216
cactgcttaa ccaaatcac                                          19

<210> SEQ ID NO 217
<211> LENGTH: 20
<212> TYPE: DNA
<213> ORGANISM: Homo sapiens

<400> SEQUENCE: 217
cagagcacag tgaaatttag                                         20

<210> SEQ ID NO 218
<211> LENGTH: 30
<212> TYPE: DNA
```

<213> ORGANISM: Homo sapiens

<400> SEQUENCE: 218
ccggaattcg agacgcttca tctgaaggaa                30

<210> SEQ ID NO 219
<211> LENGTH: 31
<212> TYPE: DNA
<213> ORGANISM: Homo sapiens

<400> SEQUENCE: 219
cccaagcttc tgactcaaac acctgctgga t               31

<210> SEQ ID NO 220
<211> LENGTH: 19
<212> TYPE: DNA
<213> ORGANISM: Homo sapiens

<400> SEQUENCE: 220
ccagccgctg attgggaag                             19

<210> SEQ ID NO 221
<211> LENGTH: 19
<212> TYPE: DNA
<213> ORGANISM: Homo sapiens

<400> SEQUENCE: 221
gaactcagcc accatgtcc                             19

<210> SEQ ID NO 222
<211> LENGTH: 19
<212> TYPE: DNA
<213> ORGANISM: Homo sapiens

<400> SEQUENCE: 222
ggacggtctt gggtcgcct                             19

<210> SEQ ID NO 223
<211> LENGTH: 19
<212> TYPE: DNA
<213> ORGANISM: Homo sapiens

<400> SEQUENCE: 223
tgctccgggg tcgctatca                             19

<210> SEQ ID NO 224
<211> LENGTH: 22
<212> TYPE: DNA
<213> ORGANISM: Homo sapiens

<400> SEQUENCE: 224
ccgcagcaca agcacagata ag                         22

<210> SEQ ID NO 225
<211> LENGTH: 19
<212> TYPE: DNA
<213> ORGANISM: Homo sapiens

<400> SEQUENCE: 225
cccccgagtg accccccact                            19

<210> SEQ ID NO 226
<211> LENGTH: 17

<212> TYPE: DNA
<213> ORGANISM: Homo sapiens

<400> SEQUENCE: 226
ggcacgagct gcccagg                                                  17

<210> SEQ ID NO 227
<211> LENGTH: 19
<212> TYPE: DNA
<213> ORGANISM: Homo sapiens

<400> SEQUENCE: 227
cccaaaactc caagcctgc                                                19

<210> SEQ ID NO 228
<211> LENGTH: 23
<212> TYPE: DNA
<213> ORGANISM: Homo sapiens

<400> SEQUENCE: 228
gtcagagatt cagggacact tgg                                           23

<210> SEQ ID NO 229
<211> LENGTH: 19
<212> TYPE: DNA
<213> ORGANISM: Homo sapiens

<400> SEQUENCE: 229
atgctttcag cctcacacc                                                19

<210> SEQ ID NO 230
<211> LENGTH: 29
<212> TYPE: DNA
<213> ORGANISM: Homo sapiens

<400> SEQUENCE: 230
cggtcgacgg gggacccttt gtcatgaag                                     29

<210> SEQ ID NO 231
<211> LENGTH: 29
<212> TYPE: DNA
<213> ORGANISM: Homo sapiens

<400> SEQUENCE: 231
cgggatccca tttgatacca gcggttgtt                                     29

<210> SEQ ID NO 232
<211> LENGTH: 37
<212> TYPE: DNA
<213> ORGANISM: Homo sapiens

<400> SEQUENCE: 232
actgaatgtc agtgcagtcc aatttacagg ctggagc                            37

<210> SEQ ID NO 233
<211> LENGTH: 36
<212> TYPE: DNA
<213> ORGANISM: Homo sapiens

<400> SEQUENCE: 233
cctctgtccc atttgcaagc ttcagtaact gttccc                             36

<210> SEQ ID NO 234

```
<211> LENGTH: 20
<212> TYPE: DNA
<213> ORGANISM: Homo sapiens

<400> SEQUENCE: 234
tggaaccaga tgtaccagca                                              20

<210> SEQ ID NO 235
<211> LENGTH: 20
<212> TYPE: DNA
<213> ORGANISM: Homo sapiens

<400> SEQUENCE: 235
gggaagaggg actgatttgc                                              20

<210> SEQ ID NO 236
<211> LENGTH: 20
<212> TYPE: DNA
<213> ORGANISM: Homo sapiens

<400> SEQUENCE: 236
acgtagggct taatagtggg                                              20

<210> SEQ ID NO 237
<211> LENGTH: 20
<212> TYPE: DNA
<213> ORGANISM: Homo sapiens

<400> SEQUENCE: 237
gtttaatgct caaacgctcc                                              20

<210> SEQ ID NO 238
<211> LENGTH: 30
<212> TYPE: DNA
<213> ORGANISM: Homo sapiens

<400> SEQUENCE: 238
aatctcattt atatgtactt acatgccagt                                   30

<210> SEQ ID NO 239
<211> LENGTH: 29
<212> TYPE: DNA
<213> ORGANISM: Homo sapiens

<400> SEQUENCE: 239
ggttcatatt cataccaaag aatgacatc                                    29

<210> SEQ ID NO 240
<211> LENGTH: 20
<212> TYPE: DNA
<213> ORGANISM: Homo sapiens

<400> SEQUENCE: 240
gctgctgggc cagggctgtg                                              20

<210> SEQ ID NO 241
<211> LENGTH: 20
<212> TYPE: DNA
<213> ORGANISM: Homo sapiens

<400> SEQUENCE: 241
gcagaggcag ctggcaccag                                              20
```

-continued

```
<210> SEQ ID NO 242
<211> LENGTH: 19
<212> TYPE: DNA
<213> ORGANISM: Homo sapiens

<400> SEQUENCE: 242
gccggcagag cggcggtac                                                  19

<210> SEQ ID NO 243
<211> LENGTH: 18
<212> TYPE: DNA
<213> ORGANISM: Homo sapiens

<400> SEQUENCE: 243
ctggctcccg cgccttcc                                                   18

<210> SEQ ID NO 244
<211> LENGTH: 20
<212> TYPE: DNA
<213> ORGANISM: Homo sapiens

<400> SEQUENCE: 244
tggctggatt ttgtacttac                                                 20

<210> SEQ ID NO 245
<211> LENGTH: 20
<212> TYPE: DNA
<213> ORGANISM: Homo sapiens

<400> SEQUENCE: 245
accagaaagc aggatttagt                                                 20

<210> SEQ ID NO 246
<211> LENGTH: 22
<212> TYPE: DNA
<213> ORGANISM: Homo sapiens

<400> SEQUENCE: 246
cataccacag gggcatcctc ac                                              22

<210> SEQ ID NO 247
<211> LENGTH: 22
<212> TYPE: DNA
<213> ORGANISM: Homo sapiens

<400> SEQUENCE: 247
cagagcaggt gcgtgaggtg ct                                              22

<210> SEQ ID NO 248
<211> LENGTH: 20
<212> TYPE: DNA
<213> ORGANISM: Homo sapiens

<400> SEQUENCE: 248
gctgactctg ccagtgcctg                                                 20

<210> SEQ ID NO 249
<211> LENGTH: 20
<212> TYPE: DNA
<213> ORGANISM: Homo sapiens

<400> SEQUENCE: 249
cagggccatc acaggtcccc                                                 20
```

```
<210> SEQ ID NO 250
<211> LENGTH: 24
<212> TYPE: DNA
<213> ORGANISM: Homo sapiens

<400> SEQUENCE: 250
tggctatttt tacctccttt gttt                                          24

<210> SEQ ID NO 251
<211> LENGTH: 20
<212> TYPE: DNA
<213> ORGANISM: Homo sapiens

<400> SEQUENCE: 251
agttccagat ggatcccaga                                               20

<210> SEQ ID NO 252
<211> LENGTH: 20
<212> TYPE: DNA
<213> ORGANISM: Homo sapiens

<400> SEQUENCE: 252
agaacccctg actccttaga                                               20

<210> SEQ ID NO 253
<211> LENGTH: 18
<212> TYPE: DNA
<213> ORGANISM: Homo sapiens

<400> SEQUENCE: 253
gagggagagg cattcaaa                                                 18

<210> SEQ ID NO 254
<211> LENGTH: 20
<212> TYPE: DNA
<213> ORGANISM: Homo sapiens

<400> SEQUENCE: 254
ttgtcttttg ggctgtagca                                               20

<210> SEQ ID NO 255
<211> LENGTH: 26
<212> TYPE: DNA
<213> ORGANISM: Homo sapiens

<400> SEQUENCE: 255
tcatgacaga gatcattgta ctgaaa                                        26

<210> SEQ ID NO 256
<211> LENGTH: 29
<212> TYPE: DNA
<213> ORGANISM: Homo sapiens

<400> SEQUENCE: 256
tcccattgct cacaaaggtc ttgtttttg                                     29

<210> SEQ ID NO 257
<211> LENGTH: 20
<212> TYPE: DNA
<213> ORGANISM: Homo sapiens

<400> SEQUENCE: 257
attcctcgca acactgggaa                                               20
```

<210> SEQ ID NO 258
<211> LENGTH: 18
<212> TYPE: DNA
<213> ORGANISM: Homo sapiens

<400> SEQUENCE: 258
gacgccagag ctgggtca                                                18

<210> SEQ ID NO 259
<211> LENGTH: 18
<212> TYPE: DNA
<213> ORGANISM: Homo sapiens

<400> SEQUENCE: 259
ctgcccaccg tccctctt                                                18

<210> SEQ ID NO 260
<211> LENGTH: 20
<212> TYPE: DNA
<213> ORGANISM: Homo sapiens

<400> SEQUENCE: 260
tgcctgtgac actgaactcc                                              20

<210> SEQ ID NO 261
<211> LENGTH: 20
<212> TYPE: DNA
<213> ORGANISM: Homo sapiens

<400> SEQUENCE: 261
tcctgaggca gaacttcacc                                              20

<210> SEQ ID NO 262
<211> LENGTH: 21
<212> TYPE: DNA
<213> ORGANISM: Homo sapiens

<400> SEQUENCE: 262
aaagcagatg ggtttgtttt g                                            21

<210> SEQ ID NO 263
<211> LENGTH: 18
<212> TYPE: DNA
<213> ORGANISM: Homo sapiens

<400> SEQUENCE: 263
ggccacgctg gtagagag                                                18

<210> SEQ ID NO 264
<211> LENGTH: 10
<212> TYPE: DNA
<213> ORGANISM: Unknown
<220> FEATURE:
<223> OTHER INFORMATION: Synthetic microbiome 16s primer sequence

<400> SEQUENCE: 264 gtgccagcmg                                                         10

<210> SEQ ID NO 265
<211> LENGTH: 10
<212> TYPE: DNA
<213> ORGANISM: Unknown
<220> FEATURE:

-continued

```
<223> OTHER INFORMATION: Synthetic microbiome 16s primer sequence

<400> SEQUENCE: 265 ggactachvg                                                          10

<210> SEQ ID NO 266
<211> LENGTH: 17
<212> TYPE: DNA
<213> ORGANISM: Unknown
<220> FEATURE:
<223> OTHER INFORMATION: Synthetic microbiome transposase sequence

<400> SEQUENCE: 266
tcgtcggcag cgtcaga                                                  17

<210> SEQ ID NO 267
<211> LENGTH: 17
<212> TYPE: DNA
<213> ORGANISM: Unknown
<220> FEATURE:
<223> OTHER INFORMATION: Synthetic microbiome transposase sequence

<400> SEQUENCE: 267
gtctcgtggg ctcggag                                                  17

<210> SEQ ID NO 268
<211> LENGTH: 14
<212> TYPE: DNA
<213> ORGANISM: Unknown
<220> FEATURE:
<223> OTHER INFORMATION: Synthetic microbiome forward index sequence

<400> SEQUENCE: 268
aatgatacgg cgac                                                     14

<210> SEQ ID NO 269
<211> LENGTH: 14
<212> TYPE: DNA
<213> ORGANISM: Unknown
<220> FEATURE:
<223> OTHER INFORMATION: Synthetic microbiome forward index sequence

<400> SEQUENCE: 269
caagcagaag acgg                                                     14
```